United States Patent
Templin et al.

(10) Patent No.: US 9,340,789 B2
(45) Date of Patent: *May 17, 2016

(54) UNA OLIGOMER STRUCTURES FOR THERAPEUTIC AGENTS

(75) Inventors: Michael V. Templin, Bothell, WA (US); Narendra K. Vaish, Kirkland, WA (US); Barry A. Polisky, Boulder, CO (US); Michael E. Houston, Jr., Sammamish, WA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 247 days.

This patent is subject to a terminal disclaimer.

(21) Appl. No.: 13/130,032

(22) PCT Filed: Dec. 3, 2009

(86) PCT No.: PCT/US2009/066610
§ 371 (c)(1),
(2), (4) Date: Sep. 7, 2011

(87) PCT Pub. No.: WO2010/065756
PCT Pub. Date: Jun. 10, 2010

(65) Prior Publication Data
US 2011/0313020 A1    Dec. 22, 2011

Related U.S. Application Data

(60) Provisional application No. 61/119,624, filed on Dec. 3, 2008, provisional application No. 61/252,085, filed on Oct. 15, 2009.

(51) Int. Cl.
*C07H 21/04* (2006.01)
*C12N 15/113* (2010.01)
*C07H 21/00* (2006.01)
*C12N 15/11* (2006.01)

(52) U.S. Cl.
CPC .......... *C12N 15/1138* (2013.01); *C12N 15/113* (2013.01); *C12N 15/1131* (2013.01); *C12N 2310/14* (2013.01); *C12N 2310/32* (2013.01)

(58) Field of Classification Search
None
See application file for complete search history.

(56) References Cited

U.S. PATENT DOCUMENTS

| | | | |
|---|---|---|---|
| 4,199,574 A | 4/1980 | Schaeffer | |
| 4,968,686 A | 11/1990 | Townsend | |
| 5,786,359 A | 7/1998 | Reitz | |
| 5,898,031 A | 4/1999 | Crooke | |
| 6,037,176 A | 3/2000 | Bennett | |
| 6,069,132 A | 5/2000 | Revanker | |
| 6,506,559 B1 | 1/2003 | Fire | |
| 6,608,035 B1 | 8/2003 | Agrawal | |
| 7,056,704 B2 | 6/2006 | Tuschl | |
| 7,078,196 B2 | 7/2006 | Tuschl | |
| 7,432,250 B2 | 10/2008 | Crooke | |
| 7,459,547 B2 | 12/2008 | Zamore | |
| 7,560,438 B2 | 7/2009 | Fire | |
| 7,579,451 B2 | 8/2009 | Manoharan | |
| 7,595,387 B2 | 9/2009 | Leake | |
| 7,674,778 B2 | 3/2010 | Manoharan | |
| 7,691,995 B2 | 4/2010 | Zamore | |
| 7,723,512 B2 | 5/2010 | Manoharan | |
| 7,732,593 B2 | 6/2010 | Zamore | |
| 7,745,608 B2 | 6/2010 | Manoharan | |
| 7,750,144 B2 | 7/2010 | Zamore | |
| 7,772,203 B2 | 8/2010 | Zamore | |
| 7,786,290 B2 | 8/2010 | Woppmann | |
| 7,834,171 B2 | 11/2010 | Khvorova | |
| 7,915,399 B2 | 3/2011 | MacLachlan | |
| 7,956,176 B2 | 6/2011 | McSwiggen | |
| 8,084,599 B2 | 12/2011 | Rossi | |
| 8,088,904 B2 | 1/2012 | Swayze | |
| 8,101,584 B2 | 1/2012 | Kreutzer | |
| 8,101,742 B2 | 1/2012 | Kreutzer | |
| 8,124,745 B2 | 2/2012 | Allerson | |
| 8,183,362 B2 | 5/2012 | Kreutzer | |
| 8,202,980 B2 | 6/2012 | Kreutzer | |
| 8,247,540 B2 | 8/2012 | Deiters | |
| 8,258,285 B2 | 9/2012 | Baulcombe | |
| 8,273,866 B2 | 9/2012 | McSwiggen | |

(Continued)

FOREIGN PATENT DOCUMENTS

| CA | WO/03/037909 A1 | 5/2003 |
|---|---|---|
| GB | WO/96/29336 A1 | 9/1996 |

(Continued)

OTHER PUBLICATIONS

Jensen, Nucleic Acids Symposium Series No. 52, Oxford University Press 2008, pp. 133-134, Unlocked Nucleic Acid (UNA) and UNA Derivatives: Thermal Denaturation Studies.

(Continued)

Primary Examiner — Jennifer McDonald
(74) Attorney, Agent, or Firm — Eckman Basu LLP

(57) ABSTRACT

This disclosure provides double-stranded RNA complexes having one or more hydroxymethyl substituted nucleomonomer(s) in the passenger strand (or sense strand) of an RNA complex. RNA complexes of the disclosure may be useful for therapeutic applications, diagnostic applications or research applications. RNA complexes include short interfering RNA complexes (siRNA) capable of modulating gene expression comprising an antisense strand and a continuous or a discontinuous passenger strand ("sense strand"). Further, one or more hydroxymethyl substituted nucleomonomer(s) of this disclosure may be positioned at the 3'-end, at the 5'-end, at both the 3'-end and 5'end.

9 Claims, 3 Drawing Sheets

(56) References Cited

U.S. PATENT DOCUMENTS

| | | | |
|---|---|---|---|
| 8,278,425 | B2 | 10/2012 | Prakash |
| 8,299,235 | B2 | 10/2012 | Baulcombe |
| 8,314,227 | B2 | 11/2012 | Wengel |
| 8,362,231 | B2 | 1/2013 | Tuschl |
| 8,372,968 | B2 | 2/2013 | Tuschl |
| 8,415,466 | B2 | 4/2013 | Khvorova |
| 8,420,391 | B2 | 4/2013 | Tuschl |
| 8,507,661 | B2 | 8/2013 | Manoharan |
| 8,524,681 | B2 | 9/2013 | Puri |
| 8,546,143 | B2 | 10/2013 | Kreutzer |
| 8,552,171 | B2 | 10/2013 | Tuschl |
| 8,790,919 | B2 | 7/2014 | Migawa |
| 8,853,384 | B2 | 10/2014 | Tuschl |
| 8,895,721 | B2 | 11/2014 | Tuschl |
| 2003/0143732 | A1* | 7/2003 | Fosnaugh et al. ............ 435/325 |
| 2006/0122391 | A1 | 6/2006 | Babu |
| 2007/0275914 | A1* | 11/2007 | Manoharan et al. ............ 514/44 |
| 2009/0093438 | A1 | 4/2009 | McSwiggen |
| 2010/0168205 | A1 | 7/2010 | Meyers |
| 2011/0130440 | A1 | 6/2011 | Manoharan |
| 2011/0223665 | A1 | 9/2011 | Maier |
| 2013/0211063 | A1 | 8/2013 | Manoharan |
| 2014/0323541 | A1 | 10/2014 | Meyers |

FOREIGN PATENT DOCUMENTS

| | | |
|---|---|---|
| WO | WO/99/08688 A1 | 2/1999 |
| WO | WO/03/004602 A2 | 1/2003 |
| WO | WO03037909 A1 | 5/2003 |
| WO | WO03070918 A2 | 8/2003 |
| WO | WO03106477 A1 | 12/2003 |
| WO | 2004090108 A2 | 10/2004 |
| WO | WO/2004/090105 A2 | 10/2004 |
| WO | WO/2004/094595 A2 | 11/2004 |
| WO | WO/2005/089268 A2 | 9/2005 |
| WO | WO2005089287 A2 | 9/2005 |
| WO | 2005121372 A2 | 12/2005 |
| WO | WO2006085987 A2 | 8/2006 |
| WO | WO/2006/112872 A2 | 10/2006 |
| WO | 2007022369 A2 | 2/2007 |
| WO | 2007051303 A1 | 5/2007 |
| WO | WO2008147824 A2 | 12/2008 |
| WO | WO/2012/177639 A2 | 12/2012 |

OTHER PUBLICATIONS

IUPAC-IUB Joint Commission on Biochemical Nomenclature Abbreviations and Symbols for the Description of Conformations of Polynucleotide Chains, Current Protocols in Nucleic Acid Chemistry 2000, pp. A.1C.1-A.1D.3.
Mangos, Journal of the American Chemical Society, 2003, vol. 125, pp. 654-661, Efficient RNase H-Directed Cleavage of RNA Promoted by Antisense DNA or 2'F-ANA Constructs Containing Acyclic Nucleotide Inserts.
Nielsen, Bioorganic & Medicinal Chemistry,1995, vol. 3 (1), pp. 19-28, Synthesis and Evaluation of Oligodeoxynucleotides Containing Acyclic Nucleosides: Introduction of Three Novel Analogues and a Summary.
Thrane, Tetrahedron,1995, vol. 51 (37), pp. 10389-10402, Novel Linear and Branched Oligodeoxynucleotide Analogues Containing 4'-C-(Hydroxymethyl Thymidine.
Pandolfi, Nucleosides & Nucleotides, 1999, vol. 18 (9), 2051-2069.
Habus, Nucleosides & Nucleotides, 1995, vol. 14 (9&10), 1853-1859.
Elbashir, EMBO Journal, 2001, vol. 20 (23), 6877-6888.
Czauderna, Nucleic Acids Research, 2003, vol. 31 (11), 2705-2716.
Werk, FEBS Letters, 2010, vol. 584, pp. 591-598.
Kenski, Nucleic Acids Research, 2009, Advance Access, pp. 1-12.
Langkjaer, Bioorganic & Medicinal Chemistry, 2009, vol. 17, pp. 5420-5425.
Bramsen, Nucleic Acids Research, 2009, Advance Access, pp. 1-15.
Nielsen, Oligonucleotide Analogues Containing 4'-C-(Hydroxymethyl)uridine: Synthesis, Evaluation and Mass Spectrometric Analysis, Bioorganic & Medicinal Chemistry, vol. 3, No. 1 I, pp. 1493-1502, 1995.
Petersen, LNA: a versatile tool for therapeutics and genomics, TRENDS in Biotechnology vol. 21 No. 2 Feb. 2003.
Pfundheller, Locked Nucleic Acid Synthesis, Chapter 8 in Methods in Molecular Biology, vol. 288: Oligonucleotide Synthesis: Methods and Applications, Edited by: P. Herdewijn, Humana Press.
Xiaojuan Pei et a;., Arch Pharm Res 2009, vol. 31, No. 7, pp. 843-849, Synthesis of 3'-C-Hydroxymethyl-substituted Pyrimidine and Purine Nucleosides as Potential Anti-Hepatitis C Virus (HCV) Agents.
Bramsen et al., Nucleic Acids Research 2009, vol. 37, No. 9, pp. 2867-2881, A large-scale chemical modification screen identifies design rules to generate siRNAs with high activity, high stability and low toxicity.

* cited by examiner

Monomer F

Monomer G

Monomer H

Monomer I

Monomer J

R = hydrogen, alkyl, cholesteryl derivative, fluorodphore, polyamine, fatty acid, amino acid, saccharide, or polypeptide

SEQUENCE LISTING

<160> NUMBER OF SEQ ID NOS: 240

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1
cgggacucua gcauacuuat t                                             21

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (18)..(18)
<223> OTHER INFORMATION: Hydroxymethyl substituted-uracil

<400> SEQUENCE: 2
cgggacucua gcauacuuat t                                             21

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-guanine

<400> SEQUENCE: 3
cgggacucua gcauacuuat t                                             21

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base

```
<222> LOCATION: (9)..(9)
<223> OTHER INFORMATION: Hydroxymethyl substituted-uracil
<220> FEATURE:
<221> NAME/KEY: modified_base
<222> LOCATION: (10)..(10)
<223> OTHER INFORMATION: Hydroxymethyl substituted-adenine

<400> SEQUENCE: 4
cgggacucua gcauacuuat t                                              21

<210> SEQ ID NO 5
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 5
cgggacucua gcauacuuat t                                              21

<210> SEQ ID NO 6
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 6
cgggacucua gcauacuuau u                                              21

<210> SEQ ID NO 7
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (14)..(14)
<223> OTHER INFORMATION: Hydroxymethyl substituted-uracil
<220> FEATURE:
<221> NAME/KEY: modified_base
<222> LOCATION: (18)..(18)
<223> OTHER INFORMATION: Hydroxymethyl substituted-uracil

<400> SEQUENCE: 7
cgggacucua gcauacuuat t                                              21

<210> SEQ ID NO 8
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-guanine
<220> FEATURE:
<221> NAME/KEY: modified_base
<222> LOCATION: (6)..(6)
<223> OTHER INFORMATION: Hydroxymethyl substituted-cytosine

<400> SEQUENCE: 8
cgggacucua gcauacuuat t                                              21

<210> SEQ ID NO 9
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 9
cgggacucua gcauacuuat t                                              21

<210> SEQ ID NO 10
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10
cgggacucua gcauacuuat t                                              21

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11
cgggacucua gcauacuuat t                                              21

<210> SEQ ID NO 12
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12
uaaguaugcu agagucccgt t                                              21

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 13
uaaguaugcu agagucccgt t                                              21

<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14
uaaguaugcu agagucccgt t                                              21

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 15
uaaguaugcu agagucccgt t                                              21

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"
<220> FEATURE:
<221> NAME/KEY: modified_base
<222> LOCATION: (2)..(2)
<223> OTHER INFORMATION: Hydroxymethyl substituted-adenine

<400> SEQUENCE: 16
uaaguaugcu agagucccgt t                                              21

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 17
uaaguaugcu agagucccgu u                                              21

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 18
uaaguaugcu agagucccgt t                                              21

<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 19
uaaguaugcu agagucccgt t                                              21

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base

```
<222> LOCATION: (2)..(2)
<223> OTHER INFORMATION: Hydroxymethyl substituted-adenine
<220> FEATURE:
<221> NAME/KEY: modified_base
<222> LOCATION: (6)..(6)
<223> OTHER INFORMATION: Hydroxymethyl substituted-adenine

<400> SEQUENCE: 20
uaaguaugcu agagucccgt t                                              21

<210> SEQ ID NO 21
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(6)
<223> OTHER INFORMATION: Hydroxymethyl substituted-adenine

<400> SEQUENCE: 21
uaaguaugcu agagucccgt t                                              21

<210> SEQ ID NO 22
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (7)..(7)
<223> OTHER INFORMATION: Hydroxymethyl substituted-uracil

<400> SEQUENCE: 22
uaaguaugcu agagucccgt t                                              21

<210> SEQ ID NO 23
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 23
gcaauugagg agugccugat t                                              21

<210> SEQ ID NO 24
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (18)..(18)
<223> OTHER INFORMATION: Hydroxymethyl substituted-guanine

<400> SEQUENCE: 24
gcaauugagg agugccugat t                                              21

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-cytosine

<400> SEQUENCE: 25
gcaauugagg agugccugat t                                              21

<210> SEQ ID NO 26
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (9)..(10)
<223> OTHER INFORMATION: Hydroxymethyl substituted-guanine

<400> SEQUENCE: 26
gcaauugagg agugccugat t                                              21

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 27
gcaauugagg agugccugat t                                              21
```

```
<210> SEQ ID NO 28
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 28
gcaauugagg agugccugau u                                              21

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (14)..(14)
<223> OTHER INFORMATION: Hydroxymethyl substituted-guanine
<220> FEATURE:
<221> NAME/KEY: modified_base
<222> LOCATION: (18)..(18)
<223> OTHER INFORMATION: Hydroxymethyl substituted-guanine

<400> SEQUENCE: 29
gcaauugagg agugccugat t                                              21

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-cytosine
<220> FEATURE:
<221> NAME/KEY: modified_base
<222> LOCATION: (6)..(6)
<223> OTHER INFORMATION: Hydroxymethyl substituted-uracil

<400> SEQUENCE: 30
gcaauugagg agugccugat t                                              21

<210> SEQ ID NO 31
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 31
gcaauugagg agugccugat t                                              21

<210> SEQ ID NO 32
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 32
gcaauugagg agugccugat t                                              21

<210> SEQ ID NO 33
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 33
gcaauugagg agugccugat t                                              21

<210> SEQ ID NO 34
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 34
ucaggcacuc cucaauugct t                                              21

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 35
ucaggcacuc cucaauugct t                                              21
```

```
<210> SEQ ID NO 36
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 36
ucaggcacuc cucaauugct t                                              21

<210> SEQ ID NO 37
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 37
ucaggcacuc cucaauugct t                                              21

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-cytosine

<400> SEQUENCE: 38
ucaggcacuc cucaauugct t                                              21

<210> SEQ ID NO 39
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 39
ucaggcacuc cucaauugcu u                                              21

<210> SEQ ID NO 40
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 40
ucaggcacuc cucaauugct t                                              21

<210> SEQ ID NO 41
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 41
ucaggcacuc cucaauugct t                                              21

<210> SEQ ID NO 42
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-cytosine
<220> FEATURE:
<221> NAME/KEY: modified_base
<222> LOCATION: (6)..(6)
<223> OTHER INFORMATION: Hydroxymethyl substituted-cytosine

<400> SEQUENCE: 42
ucaggcacuc cucaauugct t                                              21

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(6)
<223> OTHER INFORMATION: Hydroxymethyl substituted-cytosine

<400> SEQUENCE: 43
```
ucaggcacuc cucaauugct t                                             21

<210> SEQ ID NO 44
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (7)..(7)
<223> OTHER INFORMATION: Hydroxymethyl substituted-adenine

<400> SEQUENCE: 44
ucaggcacuc cucaauugct t                                             21

<210> SEQ ID NO 45
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 45
ggaucuuauu ucuucggagt t                                             21

<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (18)..(18)
<223> OTHER INFORMATION: Hydroxymethyl substituted-adenine

<400> SEQUENCE: 46
ggaucuuauu ucuucggagt t                                             21

<210> SEQ ID NO 47
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:

```
<221> NAME/KEY: modified_base
<222> LOCATION: (2)..(2)
<223> OTHER INFORMATION: Hydroxymethyl substituted-guanine

<400> SEQUENCE: 47
ggaucuuauu ucuucggagt t                                              21

<210> SEQ ID NO 48
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (9)..(10)
<223> OTHER INFORMATION: Hydroxymethyl substituted-uracil

<400> SEQUENCE: 48
ggaucuuauu ucuucggagt t                                              21

<210> SEQ ID NO 49
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 49
ggaucuuauu ucuucggagt t                                              21

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 50
ggaucuuauu ucuucggagu u                                              21

<210> SEQ ID NO 51
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<220> FEATURE:
<221> NAME/KEY: modified_base
<222> LOCATION: (14)..(14)
<223> OTHER INFORMATION: Hydroxymethyl substituted-uracil
<220> FEATURE:
<221> NAME/KEY: modified_base
<222> LOCATION: (18)..(18)
<223> OTHER INFORMATION: Hydroxymethyl substituted-adenine

<400> SEQUENCE: 51
ggaucuuauu ucuucggagt t                                              21

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-guanine
<220> FEATURE:
<221> NAME/KEY: modified_base
<222> LOCATION: (6)..(6)
<223> OTHER INFORMATION: Hydroxymethyl substituted-uracil

<400> SEQUENCE: 52
ggaucuuauu ucuucggagt t                                              21

<210> SEQ ID NO 53
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 53
ggaucuuauu ucuucggagt t                                              21

<210> SEQ ID NO 54
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 54
ggaucuuauu ucuucggagt t                                              21

<210> SEQ ID NO 55
<211> LENGTH: 21
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 55
ggaucuuauu ucuucggagt t                                              21

<210> SEQ ID NO 56
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 56
cuccgaagaa auaagaucct t                                              21

<210> SEQ ID NO 57
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 57
cuccgaagaa auaagaucct t                                              21

<210> SEQ ID NO 58
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 58
cuccgaagaa auaagaucct t                                              21

<210> SEQ ID NO 59
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 59
cuccgaagaa auaagaucct t                                                 21

<210> SEQ ID NO 60
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-uracil

<400> SEQUENCE: 60
cuccgaagaa auaagaucct t                                                 21

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 61
cuccgaagaa auaagauccu u                                                 21

<210> SEQ ID NO 62
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 62
cuccgaagaa auaagaucct t                                                 21

<210> SEQ ID NO 63
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 63
cuccgaagaa auaagaucct t                                              21

<210> SEQ ID NO 64
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-uracil
<220> FEATURE:
<221> NAME/KEY: modified_base
<222> LOCATION: (6)..(6)
<223> OTHER INFORMATION: Hydroxymethyl substituted-adenine

<400> SEQUENCE: 64
cuccgaagaa auaagaucct t                                              21

<210> SEQ ID NO 65
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(6)
<223> OTHER INFORMATION: Hydroxymethyl substituted-adenine

<400> SEQUENCE: 65
cuccgaagaa auaagaucct t                                              21

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (7)..(7)
<223> OTHER INFORMATION: Hydroxymethyl substituted-adenine

<400> SEQUENCE: 66
cuccgaagaa auaagaucct t                                              21

<210> SEQ ID NO 67
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 67
auugaccacc agguuucugt t                                             21

<210> SEQ ID NO 68
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (18)..(18)
<223> OTHER INFORMATION: Hydroxymethyl substituted-uracil

<400> SEQUENCE: 68
auugaccacc agguuucugt t                                             21

<210> SEQ ID NO 69
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-uracil

<400> SEQUENCE: 69
auugaccacc agguuucugt t                                             21

<210> SEQ ID NO 70
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (9)..(10)
<223> OTHER INFORMATION: Hydroxymethyl substituted-cytosine

<400> SEQUENCE: 70
auugaccacc agguuucugt t                                             21
```

```
<210> SEQ ID NO 71
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 71
auugaccacc agguuucugt t                                              21

<210> SEQ ID NO 72
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 72
auugaccacc agguuucugu u                                              21

<210> SEQ ID NO 73
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (14)..(14)
<223> OTHER INFORMATION: Hydroxymethyl substituted-uracil
<220> FEATURE:
<221> NAME/KEY: modified_base
<222> LOCATION: (18)..(18)
<223> OTHER INFORMATION: Hydroxymethyl substituted-uracil

<400> SEQUENCE: 73
auugaccacc agguuucugt t                                              21

<210> SEQ ID NO 74
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-uracil
```

```
<220> FEATURE:
<221> NAME/KEY: modified_base
<222> LOCATION: (6)..(6)
<223> OTHER INFORMATION: Hydroxymethyl substituted-cytosine

<400> SEQUENCE: 74
auugaccacc agguuucugt t                                              21

<210> SEQ ID NO 75
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 75
auugaccacc agguuucugt t                                              21

<210> SEQ ID NO 76
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 76
auugaccacc agguuucugt t                                              21

<210> SEQ ID NO 77
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 77
auugaccacc agguuucugt t                                              21

<210> SEQ ID NO 78
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 78
```
cagaaaccug guggucaaut t                                                  21

<210> SEQ ID NO 79
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 79
cagaaaccug guggucaaut t                                                  21

<210> SEQ ID NO 80
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 80
cagaaaccug guggucaaut t                                                  21

<210> SEQ ID NO 81
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 81
cagaaaccug guggucaaut t                                                  21

<210> SEQ ID NO 82
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-adenine

<400> SEQUENCE: 82
cagaaaccug guggucaaut t                                                  21

```
<210> SEQ ID NO 83
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 83
cagaaaccug guggucaauu u                                             21

<210> SEQ ID NO 84
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 84
cagaaaccug guggucaaut t                                             21

<210> SEQ ID NO 85
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 85
cagaaaccug guggucaaut t                                             21

<210> SEQ ID NO 86
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-adenine
<220> FEATURE:
<221> NAME/KEY: modified_base
<222> LOCATION: (6)..(6)
<223> OTHER INFORMATION: Hydroxymethyl substituted-adenine

<400> SEQUENCE: 86
cagaaaccug guggucaaut t                                             21
```

-continued

<210> SEQ ID NO 87
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(6)
<223> OTHER INFORMATION: Hydroxymethyl substituted-adenine

<400> SEQUENCE: 87
cagaaaccug guggucaaut t                                              21

<210> SEQ ID NO 88
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (7)..(7)
<223> OTHER INFORMATION: Hydroxymethyl substituted-cytosine

<400> SEQUENCE: 88
cagaaaccug guggucaaut t                                              21

<210> SEQ ID NO 89
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 89
caucacacug aauaccaaut t                                              21

<210> SEQ ID NO 90
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (18)..(18)
<223> OTHER INFORMATION: Hydroxymethyl substituted-adenine

<400> SEQUENCE: 90
caucacacug aauaccaaut t                                               21

<210> SEQ ID NO 91
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-adenine

<400> SEQUENCE: 91
caucacacug aauaccaaut t                                               21

<210> SEQ ID NO 92
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (9)..(9)
<223> OTHER INFORMATION: Hydroxymethyl substituted-uracil
<220> FEATURE:
<221> NAME/KEY: modified_base
<222> LOCATION: (10)..(10)
<223> OTHER INFORMATION: Hydroxymethyl substituted-guanine

<400> SEQUENCE: 92
caucacacug aauaccaaut t                                               21

<210> SEQ ID NO 93
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 93
caucacacug aauaccaaut t                                               21

<210> SEQ ID NO 94
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 94
caucacacug aauaccaauu u                                              21

<210> SEQ ID NO 95
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (14)..(14)
<223> OTHER INFORMATION: Hydroxymethyl substituted-adenine
<220> FEATURE:
<221> NAME/KEY: modified_base
<222> LOCATION: (18)..(18)
<223> OTHER INFORMATION: Hydroxymethyl substituted-adenine

<400> SEQUENCE: 95
caucacacug aauaccaaut t                                              21

<210> SEQ ID NO 96
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-adenine
<220> FEATURE:
<221> NAME/KEY: modified_base
<222> LOCATION: (6)..(6)
<223> OTHER INFORMATION: Hydroxymethyl substituted-cytosine

<400> SEQUENCE: 96
caucacacug aauaccaaut t                                              21

<210> SEQ ID NO 97
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 97
caucacacug aauaccaaut t                                              21

<210> SEQ ID NO 98
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 98
caucacacug aauaccaaut t                                              21

<210> SEQ ID NO 99
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 99
caucacacug aauaccaaut t                                              21

<210> SEQ ID NO 100
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 100
auugguauuc agugugaugt t                                              21

<210> SEQ ID NO 101
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 101
auugguauuc agugugaugt t                                              21

<210> SEQ ID NO 102

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 102
auugguauuc agugugaugt t                                              21

<210> SEQ ID NO 103
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 103
auugguauuc agugugaugt t                                              21

<210> SEQ ID NO 104
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-uracil

<400> SEQUENCE: 104
auugguauuc agugugaugt t                                              21

<210> SEQ ID NO 105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 105
auugguauuc agugugaugu u                                              21

<210> SEQ ID NO 106
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 106
auugguauuc agugugaugt t                                              21

<210> SEQ ID NO 107
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 107
auugguauuc agugugaugt t                                              21

<210> SEQ ID NO 108
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-uracil
<220> FEATURE:
<221> NAME/KEY: modified_base
<222> LOCATION: (6)..(6)
<223> OTHER INFORMATION: Hydroxymethyl substituted-uracil

<400> SEQUENCE: 108
auugguauuc agugugaugt t                                              21

<210> SEQ ID NO 109
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(6)
<223> OTHER INFORMATION: Hydroxymethyl substituted-uracil

<400> SEQUENCE: 109
auugguauuc agugugaugt t                                              21
```

```
<210> SEQ ID NO 110
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (7)..(7)
<223> OTHER INFORMATION: Hydroxymethyl substituted-adenine

<400> SEQUENCE: 110
auugguauuc agugugaugt t                                              21

<210> SEQ ID NO 111
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 111
ggacauucag aacaagaaat t                                              21

<210> SEQ ID NO 112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 112
ggacauucag aacaagaaau u                                              21

<210> SEQ ID NO 113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 113
ggacauucag aacaagaaau u                                              21

<210> SEQ ID NO 114
<211> LENGTH: 21
```

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 114
ggacauucag aacaagaaau u                                              21

<210> SEQ ID NO 115
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 115
ggacauucag aacaagaaau u                                              21

<210> SEQ ID NO 116
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 116
ggacauucag aacaagaaau u                                              21

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 117
ggacauucag aacaagaaau u                                              21

<210> SEQ ID NO 118
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: modified_base
<222> LOCATION: (20)..(21)
<223> OTHER INFORMATION: Hydroxymethyl substituted-uracil

<400> SEQUENCE: 118
ggacauucag aacaagaaau u                                              21

<210> SEQ ID NO 119
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 119
ggacauucag aacaagaaau u                                              21

<210> SEQ ID NO 120
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 120
ggacauucag aacaagaaau u                                              21

<210> SEQ ID NO 121
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 121
ggacauucag aacaagaaau u                                              21

<210> SEQ ID NO 122
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Hydroxymethyl substituted-uracil
<220> FEATURE:
<221> NAME/KEY: modified_base
<222> LOCATION: (21)..(22)
<223> OTHER INFORMATION: Hydroxymethyl substituted-uracil
```

<400> SEQUENCE: 122
uggacauuca gaacaagaaa uu                                                  22

<210> SEQ ID NO 123
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Hydroxymethyl substituted-uracil
<220> FEATURE:
<221> NAME/KEY: modified_base
<222> LOCATION: (21)..(22)
<223> OTHER INFORMATION: Hydroxymethyl substituted-uracil

<400> SEQUENCE: 123
uggacauuca gaacaagaaa uu                                                  22

<210> SEQ ID NO 124
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 124
uuucuuguuc ugaaugucct t                                                   21

<210> SEQ ID NO 125
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 125
uuucuuguuc ugaauguccu u                                                   21

<210> SEQ ID NO 126
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Hydroxymethyl substituted-uracil
<220> FEATURE:
<221> NAME/KEY: modified_base
<222> LOCATION: (20)..(21)

```
<223> OTHER INFORMATION: Hydroxymethyl substituted-uracil

<400> SEQUENCE: 126
uuucuuguuc ugaauguccu u                                              21

<210> SEQ ID NO 127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 127
uuucuuguuc ugaauguccu u                                              21

<210> SEQ ID NO 128
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 128
uuucuuguuc ugaauguccu u                                              21

<210> SEQ ID NO 129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(5)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 129
uuucuuguuc ugaauguccu u                                              21

<210> SEQ ID NO 130
<211> LENGTH: 21
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 130
uuucuuguuc ugaauguccu u                                               21

<210> SEQ ID NO 131
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(7)
<223> OTHER INFORMATION: Hydroxymethyl substituted-guanine
<220> FEATURE:
<221> NAME/KEY: modified_base
<222> LOCATION: (20)..(21)
<223> OTHER INFORMATION: Hydroxymethyl substituted-uracil

<400> SEQUENCE: 131
uuucuuguuc ugaauguccu u                                               21

<210> SEQ ID NO 132
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 132
uuucuuguuc ugaauguccu u                                               21

<210> SEQ ID NO 133
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (10)..(10)
<223> OTHER INFORMATION: Hydroxymethyl substituted-cytosine
<220> FEATURE:
<221> NAME/KEY: modified_base
<222> LOCATION: (20)..(21)
<223> OTHER INFORMATION: Hydroxymethyl substituted-uracil

<400> SEQUENCE: 133
```
uuucuuguuc ugaauguccu u                                           21

<210> SEQ ID NO 134
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (15)..(15)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 134
uuucuuguuc ugaauguccu u                                           21

<210> SEQ ID NO 135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 135
uuucuuguuc ugaauguccu u                                           21

<210> SEQ ID NO 136
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(7)
<223> OTHER INFORMATION: Hydroxymethyl substituted-guanine
<220> FEATURE:
<221> NAME/KEY: modified_base
<222> LOCATION: (20)..(21)
<223> OTHER INFORMATION: Hydroxymethyl substituted-uracil

<400> SEQUENCE: 136
uuucuuguuc ugaauguccu u                                           21

<210> SEQ ID NO 137
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 137

```
agcuccugcu gaaggccact t                                              21
```

<210> SEQ ID NO 138
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 138

```
agcuccugcu gaaggccacu u                                              21
```

<210> SEQ ID NO 139
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Hydroxymethyl substituted-uracil
<220> FEATURE:
<221> NAME/KEY: modified_base
<222> LOCATION: (21)..(22)
<223> OTHER INFORMATION: Hydroxymethyl substituted-uracil

<400> SEQUENCE: 139

```
uagcuccugc ugaaggccac uu                                             22
```

<210> SEQ ID NO 140
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Hydroxymethyl substituted-adenine
<220> FEATURE:
<221> NAME/KEY: modified_base
<222> LOCATION: (20)..(21)
<223> OTHER INFORMATION: Hydroxymethyl substituted-uracil

<400> SEQUENCE: 140

```
agcuccugcu gaaggccacu u                                              21
```

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: Hydroxymethyl substituted-guanine
<220> FEATURE:

-continued

```
<221> NAME/KEY: modified_base
<222> LOCATION: (20)..(21)
<223> OTHER INFORMATION: Hydroxymethyl substituted-uracil

<400> SEQUENCE: 141
agcuccugcu gaaggccacu u                                              21

<210> SEQ ID NO 142
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: Hydroxymethyl substituted-cytosine
<220> FEATURE:
<221> NAME/KEY: modified_base
<222> LOCATION: (20)..(21)
<223> OTHER INFORMATION: Hydroxymethyl substituted-uracil

<400> SEQUENCE: 142
agcuccugcu gaaggccacu u                                              21

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 143
agcuccugcu gaaggccacu u                                              21

<210> SEQ ID NO 144
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 144
agcuccugcu gaaggccacu u                                              21

<210> SEQ ID NO 145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: Hydroxymethyl substituted-guanine
```

```
<220> FEATURE:
<221> NAME/KEY: modified_base
<222> LOCATION: (20)..(21)
<223> OTHER INFORMATION: Hydroxymethyl substituted-uracil

<400> SEQUENCE: 145
agcuccugcu gaaggccacu u                                              21

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: Hydroxymethyl substituted-guanine
<220> FEATURE:
<221> NAME/KEY: modified_base
<222> LOCATION: (20)..(21)
<223> OTHER INFORMATION: Hydroxymethyl substituted-uracil

<400> SEQUENCE: 146
agcuccugcu gaaggccacu u                                              21

<210> SEQ ID NO 147
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 147
guggccuuca gcaggagcut t                                              21

<210> SEQ ID NO 148
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 148
guggccuuca gcaggagcuu u                                              21

<210> SEQ ID NO 149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
```

<223> OTHER INFORMATION: Hydroxymethyl substituted-uracil

<400> SEQUENCE: 149
guggccuuca gcaggagcuu u                                              21

<210> SEQ ID NO 150
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 150
guggccuuca gcaggagcuu u                                              21

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 151
guggccuuca gcaggagcuu u                                              21

<210> SEQ ID NO 152
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(21)
<223> OTHER INFORMATION: Hydroxymethyl substituted-uracil

<400> SEQUENCE: 152
guggccuuca gcaggagcuu u                                              21

<210> SEQ ID NO 153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 153
guggccuuca gcaggagcuu u                                    21

<210> SEQ ID NO 154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(7)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 154
guggccuuca gcaggagcuu u                                    21

<210> SEQ ID NO 155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 155
guggccuuca gcaggagcuu u                                    21

<210> SEQ ID NO 156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: Hydroxymethyl substituted-uracil
<220> FEATURE:
<221> NAME/KEY: modified_base
<222> LOCATION: (20)..(21)
<223> OTHER INFORMATION: Hydroxymethyl substituted-uracil

<400> SEQUENCE: 156
guggccuuca gcaggagcuu u                                    21

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:

```
<221> NAME/KEY: modified_base
<222> LOCATION: (7)..(8)
<223> OTHER INFORMATION: 2'-O-methyl-uracil
<220> FEATURE:
<221> NAME/KEY: modified_base
<222> LOCATION: (10)..(10)
<223> OTHER INFORMATION: 2'-O-methyl-uracil
<220> FEATURE:
<221> NAME/KEY: modified_base
<222> LOCATION: (12)..(14)
<223> OTHER INFORMATION: 2'-O-methyl-uracil
<220> FEATURE:
<221> NAME/KEY: modified_base
<222> LOCATION: (19)..(19)
<223> OTHER INFORMATION: 2'-O-methyl-cytosine
<220> FEATURE:
<221> NAME/KEY: misc_feature
<222> LOCATION: (20)..(21)
<223> OTHER INFORMATION: Phosphorothioate linkage

<400> SEQUENCE: 157
ggaaucuuau auuugaucca a                                              21

<210> SEQ ID NO 158
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: 2'-O-methyl-uracil
<220> FEATURE:
<221> NAME/KEY: modified_base
<222> LOCATION: (7)..(7)
<223> OTHER INFORMATION: 2'-O-methyl-cytosine
<220> FEATURE:
<221> NAME/KEY: modified_base
<222> LOCATION: (11)..(11)
<223> OTHER INFORMATION: 2'-O-methyl-uracil
<220> FEATURE:
<221> NAME/KEY: modified_base
<222> LOCATION: (13)..(13)
<223> OTHER INFORMATION: 2'-O-methyl-uracil
<220> FEATURE:
<221> NAME/KEY: modified_base
<222> LOCATION: (18)..(18)
<223> OTHER INFORMATION: 2'-O-methyl-uracil
<220> FEATURE:
<221> NAME/KEY: modified_base
<222> LOCATION: (21)..(21)
<223> OTHER INFORMATION: 2'-O-methyl-cytosine
<220> FEATURE:
<221> NAME/KEY: misc_feature
<222> LOCATION: (21)..(22)
<223> OTHER INFORMATION: Phosphorothioate linkage
<220> FEATURE:
<221> NAME/KEY: modified_base
<222> LOCATION: (22)..(22)
<223> OTHER INFORMATION: 2'-O-methyl-cytosine
<220> FEATURE:
<221> NAME/KEY: misc_feature
<222> LOCATION: (22)..(23)
<223> OTHER INFORMATION: Phosphorothioate linkage

<400> SEQUENCE: 158
uuggaucaaa uauaagauuc ccu                                            23

<210> SEQ ID NO 159
<211> LENGTH: 25
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(2)
<223> OTHER INFORMATION: 2'-O-methyl-guanine

<400> SEQUENCE: 159
ggaucuuauu ucuucggaga caatg                                          25

<210> SEQ ID NO 160
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2'-O-methyl-cytosine
<220> FEATURE:
<221> NAME/KEY: modified_base
<222> LOCATION: (2)..(2)
<223> OTHER INFORMATION: 2'-O-methyl-adenine

<400> SEQUENCE: 160
cauugucucc gaagaaauaa gauccuu                                        27

<210> SEQ ID NO 161
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 161
cgggacucua gcauacuuac ugaca                                          25

<210> SEQ ID NO 162
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(21)
<223> OTHER INFORMATION: Hydroxymethyl substituted-uracil
<220> FEATURE:
<221> NAME/KEY: modified_base
<222> LOCATION: (22)..(22)
<223> OTHER INFORMATION: Hydroxymethyl substituted-guanine
```

```
<400> SEQUENCE: 162
cgggacucua gcauacuuac ugaca                                          25

<210> SEQ ID NO 163
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(21)
<223> OTHER INFORMATION: Hydroxymethyl substituted-uracil
<220> FEATURE:
<221> NAME/KEY: modified_base
<222> LOCATION: (22)..(22)
<223> OTHER INFORMATION: Hydroxymethyl substituted-guanine

<400> SEQUENCE: 163
cgggacucua gcauacuuac ugaca                                          25

<210> SEQ ID NO 164
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 164
cgggacucua gcauacuuac ugaca                                          25

<210> SEQ ID NO 165
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-guanine
<220> FEATURE:
<221> NAME/KEY: modified_base
<222> LOCATION: (6)..(6)
<223> OTHER INFORMATION: Hydroxymethyl substituted-cytosine

<400> SEQUENCE: 165
cgggacucua gcauacuuac ugaca                                          25

<210> SEQ ID NO 166
<211> LENGTH: 25
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 166
cgggacucua gcauacuuac ugaca                                           25

<210> SEQ ID NO 167
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 167
cgggacucua gcauacuuac ugaca                                           25

<210> SEQ ID NO 168
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (25)..(25)
<223> OTHER INFORMATION: Hydroxymethyl substituted-adenine

<400> SEQUENCE: 168
cgggacucua gcauacuuac ugaca                                           25

<210> SEQ ID NO 169
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
ugucaguaag uaugcuagag ucccguu                                         27

<210> SEQ ID NO 170
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
```

```
<223> OTHER INFORMATION: Hydroxymethyl substituted-guanine
<220> FEATURE:
<221> NAME/KEY: modified_base
<222> LOCATION: (7)..(7)
<223> OTHER INFORMATION: Hydroxymethyl substituted-uracil

<400> SEQUENCE: 170
ugucaguaag uaugcuagag ucccguu                                          27

<210> SEQ ID NO 171
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
ugucaguaag uaugcuagag ucccguu                                          27

<210> SEQ ID NO 172
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: Hydroxymethyl substituted-guanine
<220> FEATURE:
<221> NAME/KEY: modified_base
<222> LOCATION: (7)..(7)
<223> OTHER INFORMATION: Hydroxymethyl substituted-uracil

<400> SEQUENCE: 172
ugucaguaag uaugcuagag ucccguu                                          27

<210> SEQ ID NO 173
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
ugucaguaag uaugcuagag ucccguu                                          27

<210> SEQ ID NO 174
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: Hydroxymethyl substituted-adenine
<220> FEATURE:
<221> NAME/KEY: modified_base
<222> LOCATION: (12)..(12)
<223> OTHER INFORMATION: Hydroxymethyl substituted-adenine

<400> SEQUENCE: 174
```
ugucaguaag uaugcuagag ucccguu                                    27

<210> SEQ ID NO 175
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (12)..(12)
<223> OTHER INFORMATION: Hydroxymethyl substituted-adenine

<400> SEQUENCE: 175
ugucaguaag uaugcuagag ucccguu                                    27

<210> SEQ ID NO 176
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (26)..(27)
<223> OTHER INFORMATION: Hydroxymethyl substituted-uracil

<400> SEQUENCE: 176
ugucaguaag uaugcuagag ucccguu                                    27

<210> SEQ ID NO 177
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 177
gcaauugagg agugccugau uaatg                                      25

<210> SEQ ID NO 178
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(21)
<223> OTHER INFORMATION: Hydroxymethyl substituted-uracil
<220> FEATURE:
<221> NAME/KEY: modified_base
<222> LOCATION: (22)..(22)
<223> OTHER INFORMATION: Hydroxymethyl substituted-adenine -continued

<400> SEQUENCE: 178
gcaauugagg agugccugau uaatg                                              25

<210> SEQ ID NO 179
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(21)
<223> OTHER INFORMATION: Hydroxymethyl substituted-uracil
<220> FEATURE:
<221> NAME/KEY: modified_base
<222> LOCATION: (22)..(22)
<223> OTHER INFORMATION: Hydroxymethyl substituted-adenine

<400> SEQUENCE: 179
gcaauugagg agugccugau uaatg                                              25

<210> SEQ ID NO 180
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 180
gcaauugagg agugccugau uaatg                                              25

<210> SEQ ID NO 181
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-cytosine
<220> FEATURE:
<221> NAME/KEY: modified_base
<222> LOCATION: (6)..(6)
<223> OTHER INFORMATION: Hydroxymethyl substituted-uracil

<400> SEQUENCE: 181
gcaauugagg agugccugau uaatg                                              25

<210> SEQ ID NO 182
<211> LENGTH: 25
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 182
gcaauugagg agugccugau uaatg                                              25

<210> SEQ ID NO 183
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 183
gcaauugagg agugccugau uaatg                                              25

<210> SEQ ID NO 184
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (25)..(25)
<223> OTHER INFORMATION: Hydroxymethyl substituted-guanine

<400> SEQUENCE: 184
gcaauugagg agugccugau uaaug                                              25

<210> SEQ ID NO 185
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
cauuaaucag gcacuccuca auugcuu                                            27

<210> SEQ ID NO 186
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
```

```
<223> OTHER INFORMATION: Hydroxymethyl substituted-adenine
<220> FEATURE:
<221> NAME/KEY: modified_base
<222> LOCATION: (7)..(7)
<223> OTHER INFORMATION: Hydroxymethyl substituted-uracil

<400> SEQUENCE: 186
cauuaaucag gcacuccuca auugcuu                                              27

<210> SEQ ID NO 187
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
cauuaaucag gcacuccuca auugcuu                                              27

<210> SEQ ID NO 188
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: Hydroxymethyl substituted-adenine
<220> FEATURE:
<221> NAME/KEY: modified_base
<222> LOCATION: (7)..(7)
<223> OTHER INFORMATION: Hydroxymethyl substituted-uracil

<400> SEQUENCE: 188
cauuaaucag gcacuccuca auugcuu                                              27

<210> SEQ ID NO 189
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
cauuaaucag gcacuccuca auugcuu                                              27

<210> SEQ ID NO 190
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: Hydroxymethyl substituted-cytosine
<220> FEATURE:
<221> NAME/KEY: modified_base
<222> LOCATION: (12)..(12)
<223> OTHER INFORMATION: Hydroxymethyl substituted-cytosine

<400> SEQUENCE: 190
```

```
cauuaaucag gcacuccuca auugcuu                                              27
```

<210> SEQ ID NO 191
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (12)..(12)
<223> OTHER INFORMATION: Hydroxymethyl substituted-cytosine

<400> SEQUENCE: 191

```
cauuaaucag gcacuccuca auugcuu                                              27
```

<210> SEQ ID NO 192
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (26)..(27)
<223> OTHER INFORMATION: Hydroxymethyl substituted-uracil

<400> SEQUENCE: 192

```
cauuaaucag gcacuccuca auugcuu                                              27
```

<210> SEQ ID NO 193
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 193

```
ggaucuuauu ucuucggaga caatg                                                25
```

<210> SEQ ID NO 194
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(21)
<223> OTHER INFORMATION: Hydroxymethyl substituted-cytosine
<220> FEATURE:
<221> NAME/KEY: modified_base
<222> LOCATION: (22)..(22)
<223> OTHER INFORMATION: Hydroxymethyl substituted-adenine

```
<400> SEQUENCE: 194
ggaucuuauu ucuucggaga caatg                                              25

<210> SEQ ID NO 195
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(21)
<223> OTHER INFORMATION: Hydroxymethyl substituted-cytosine
<220> FEATURE:
<221> NAME/KEY: modified_base
<222> LOCATION: (22)..(22)
<223> OTHER INFORMATION: Hydroxymethyl substituted-adenine

<400> SEQUENCE: 195
ggaucuuauu ucuucggaga caatg                                              25

<210> SEQ ID NO 196
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 196
ggaucuuauu ucuucggaga caatg                                              25

<210> SEQ ID NO 197
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-guanine
<220> FEATURE:
<221> NAME/KEY: modified_base
<222> LOCATION: (6)..(6)
<223> OTHER INFORMATION: Hydroxymethyl substituted-uracil

<400> SEQUENCE: 197
ggaucuuauu ucuucggaga caatg                                              25

<210> SEQ ID NO 198
<211> LENGTH: 25
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 198
ggaucuuauu ucuucggaga caatg                                           25

<210> SEQ ID NO 199
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 199
ggaucuuauu ucuucggaga caatg                                           25

<210> SEQ ID NO 200
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (25)..(25)
<223> OTHER INFORMATION: Hydroxymethyl substituted-guanine

<400> SEQUENCE: 200
ggaucuuauu ucuucggaga caaug                                           25

<210> SEQ ID NO 201
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
cauugucucc gaagaaauaa gauccuu                                         27

<210> SEQ ID NO 202
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
```

-continued

<223> OTHER INFORMATION: Hydroxymethyl substituted-uracil
<220> FEATURE:
<221> NAME/KEY: modified_base
<222> LOCATION: (7)..(7)
<223> OTHER INFORMATION: Hydroxymethyl substituted-cytosine

<400> SEQUENCE: 202
cauugucucc gaagaaauaa gauccuu                                        27

<210> SEQ ID NO 203
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
cauugucucc gaagaaauaa gauccuu                                        27

<210> SEQ ID NO 204
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: Hydroxymethyl substituted-uracil
<220> FEATURE:
<221> NAME/KEY: modified_base
<222> LOCATION: (7)..(7)
<223> OTHER INFORMATION: Hydroxymethyl substituted-cytosine

<400> SEQUENCE: 204
cauugucucc gaagaaauaa gauccuu                                        27

<210> SEQ ID NO 205
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
cauugucucc gaagaaauaa gauccuu                                        27

<210> SEQ ID NO 206
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: Hydroxymethyl substituted-uracil
<220> FEATURE:
<221> NAME/KEY: modified_base
<222> LOCATION: (12)..(12)
<223> OTHER INFORMATION: Hydroxymethyl substituted-adenine

<400> SEQUENCE: 206
cauugucucc gaagaaauaa gauccuu                                27

<210> SEQ ID NO 207
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (12)..(12)
<223> OTHER INFORMATION: Hydroxymethyl substituted-adenine

<400> SEQUENCE: 207
cauugucucc gaagaaauaa gauccuu                                27

<210> SEQ ID NO 208
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (26)..(27)
<223> OTHER INFORMATION: Hydroxymethyl substituted-uracil

<400> SEQUENCE: 208
cauugucucc gaagaaauaa gauccuu                                27

<210> SEQ ID NO 209
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 209
auugaccacc agguuucugu uuaca                                  25

<210> SEQ ID NO 210
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(22)
<223> OTHER INFORMATION: Hydroxymethyl substituted-uracil

<400> SEQUENCE: 210
auugaccacc agguuucugu uuaca                                  25

```
<210> SEQ ID NO 211
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(22)
<223> OTHER INFORMATION: Hydroxymethyl substituted-uracil

<400> SEQUENCE: 211
auugaccacc agguuucugu uuaca                                         25

<210> SEQ ID NO 212
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 212
auugaccacc agguuucugu uuaca                                         25

<210> SEQ ID NO 213
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-uracil
<220> FEATURE:
<221> NAME/KEY: modified_base
<222> LOCATION: (6)..(6)
<223> OTHER INFORMATION: Hydroxymethyl substituted-cytosine

<400> SEQUENCE: 213
auugaccacc agguuucugu uuaca                                         25

<210> SEQ ID NO 214
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

<400> SEQUENCE: 214
auugaccacc agguuucugu uuaca                                              25

<210> SEQ ID NO 215
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 215
auugaccacc agguuucugu uuaca                                              25

<210> SEQ ID NO 216
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (25)..(25)
<223> OTHER INFORMATION: Hydroxymethyl substituted-adenine

<400> SEQUENCE: 216
auugaccacc agguuucugu uuaca                                              25

<210> SEQ ID NO 217
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
uguaaacaga aaccuggugg ucaauuu                                            27

<210> SEQ ID NO 218
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: Hydroxymethyl substituted-adenine
<220> FEATURE:
<221> NAME/KEY: modified_base
<222> LOCATION: (7)..(7)
<223> OTHER INFORMATION: Hydroxymethyl substituted-cytosine

<400> SEQUENCE: 218
uguaaacaga aaccuggugg ucaauuu                                            27

<210> SEQ ID NO 219
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
uguaaacaga aaccuggugg ucaauuu                                            27

<210> SEQ ID NO 220
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: Hydroxymethyl substituted-adenine
<220> FEATURE:
<221> NAME/KEY: modified_base
<222> LOCATION: (7)..(7)
<223> OTHER INFORMATION: Hydroxymethyl substituted-cytosine

<400> SEQUENCE: 220
uguaaacaga aaccuggugg ucaauuu                                            27

<210> SEQ ID NO 221
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
uguaaacaga aaccuggugg ucaauuu                                            27

<210> SEQ ID NO 222
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: Hydroxymethyl substituted-adenine
<220> FEATURE:
<221> NAME/KEY: modified_base
<222> LOCATION: (12)..(12)
<223> OTHER INFORMATION: Hydroxymethyl substituted-adenine

<400> SEQUENCE: 222
uguaaacaga aaccuggugg ucaauuu                                            27

<210> SEQ ID NO 223
<211> LENGTH: 27
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (12)..(12)
<223> OTHER INFORMATION: Hydroxymethyl substituted-adenine

<400> SEQUENCE: 223
uguaaacaga aaccuggugg ucaauuu                                          27

<210> SEQ ID NO 224
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (26)..(27)
<223> OTHER INFORMATION: Hydroxymethyl substituted-uracil

<400> SEQUENCE: 224
uguaaacaga aaccuggugg ucaauuu                                          27

<210> SEQ ID NO 225
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 225
gucaucacac ugaauaccaa ugctg                                            25

<210> SEQ ID NO 226
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(21)
<223> OTHER INFORMATION: Hydroxymethyl substituted-uracil
<220> FEATURE:
<221> NAME/KEY: modified_base
<222> LOCATION: (22)..(22)
<223> OTHER INFORMATION: Hydroxymethyl substituted-guanine

<400> SEQUENCE: 226
gucaucacac ugaauaccaa ugctg                                            25

<210> SEQ ID NO 227
<211> LENGTH: 25
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (21)..(21)
<223> OTHER INFORMATION: Hydroxymethyl substituted-uracil
<220> FEATURE:
<221> NAME/KEY: modified_base
<222> LOCATION: (22)..(22)
<223> OTHER INFORMATION: Hydroxymethyl substituted-guanine

<400> SEQUENCE: 227
gucaucacac ugaauaccaa ugctg                                           25

<210> SEQ ID NO 228
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 228
gucaucacac ugaauaccaa ugctg                                           25

<210> SEQ ID NO 229
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Hydroxymethyl substituted-uracil
<220> FEATURE:
<221> NAME/KEY: modified_base
<222> LOCATION: (6)..(6)
<223> OTHER INFORMATION: Hydroxymethyl substituted-cytosine

<400> SEQUENCE: 229
gucaucacac ugaauaccaa ugctg                                           25

<210> SEQ ID NO 230
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 230
gucaucacac ugaauaccaa ugctg                                         25

<210> SEQ ID NO 231
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 231
gucaucacac ugaauaccaa ugctg                                         25

<210> SEQ ID NO 232
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (25)..(25)
<223> OTHER INFORMATION: Hydroxymethyl substituted-guanine

<400> SEQUENCE: 232
gucaucacac ugaauaccaa ugcug                                         25

<210> SEQ ID NO 233
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
cagcauuggu auucagugug augacac                                       27

<210> SEQ ID NO 234
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(7)
<223> OTHER INFORMATION: Hydroxymethyl substituted-uracil

<400> SEQUENCE: 234
cagcauuggu auucagugug augacac                                       27

<210> SEQ ID NO 235
```

```
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
cagcauuggu auucagugug augacac                                               27

<210> SEQ ID NO 236
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(7)
<223> OTHER INFORMATION: Hydroxymethyl substituted-uracil

<400> SEQUENCE: 236
cagcauuggu auucagugug augacac                                               27

<210> SEQ ID NO 237
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
cagcauuggu auucagugug augacac                                               27

<210> SEQ ID NO 238
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: Hydroxymethyl substituted-guanine
<220> FEATURE:
<221> NAME/KEY: modified_base
<222> LOCATION: (12)..(12)
<223> OTHER INFORMATION: Hydroxymethyl substituted-uracil

<400> SEQUENCE: 238
cagcauuggu auucagugug augacac                                               27

<210> SEQ ID NO 239
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (12)..(12)
<223> OTHER INFORMATION: Hydroxymethyl substituted-uracil
```

```
<400> SEQUENCE: 239
cagcauuggu auucagugug augacac                                                27

<210> SEQ ID NO 240
<211> LENGTH: 27
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (26)..(26)
<223> OTHER INFORMATION: Hydroxymethyl substituted-adenine
<220> FEATURE:
<221> NAME/KEY: modified_base
<222> LOCATION: (27)..(27)
<223> OTHER INFORMATION: Hydroxymethyl substituted-cytosine

<400> SEQUENCE: 240
cagcauuggu auucagugug augacac                                                27
```

UNA OLIGOMER STRUCTURES FOR THERAPEUTIC AGENTS

CROSS REFERENCE TO RELATED APPLICATIONS

This application is the National Stage application of PCT International Application PCT/US2009/066610, filed Dec. 3, 2009, which claimed the benefit of U.S. Provisional Application No. 61/252,085, filed Oct. 15, 2009, and U.S. Provisional Application No. 61/119,624, filed Dec. 3, 2008, each of which is hereby incorporated by reference in its entirety.

FIELD OF THE DISCLOSURE

The present disclosure is directed to double-stranded RNA complexes having one or more hydroxymethyl substituted nucleomonomer(s) in the passenger strand of the RNA complex. The RNA complexes of the disclosure may be useful for therapeutic applications, diagnostic applications or research applications. The complexes include short interfering RNA complexes (siRNA duplexes) capable of down-regulating gene expression comprising an antisense strand and a continuous or a discontinuous passenger strand ("sense strand"). At least one of these strands have one or more hydroxymethyl substituted nucleomonomer(s) of this disclosure, that can be positioned at the 3'-end, at the 5'-end, at both the 3'-end and 5' end, and/or internally.

SEQUENCE LISTING

This application includes a sequence listing submitted herewith via EFS as an ASCII file created on Dec. 3, 2009, named 08-19PCT_Sequence_Listing.txt, which is 98,574 bytes in size, and is hereby incorporated by reference in its entirety.

BACKGROUND

RNA interference (RNAi) provides a means to silence the expression of a target gene. It provides basic research with a method for studying genetic and biochemical pathways, and the function of individual genes and gene products. Consequently, RNAi has become a critical tool for target validation in the pharmaceutical industry, and substantial investments have been made with the goal of developing drugs based on RNA complexes capable of mediating RNA interference against genes whose aberrant expression is linked to a disease state or condition.

However, the ability of RNA complexes to function as an RNAi therapeutic is limited by such problems as sequence specificity or "off-target" effect, potency, nuclease stability, and non-specific cytokine induction.

This disclosure provides compounds, compositions, methods and uses for improving RNAi activity of RNA complexes while at the same time minimizing or eliminating the adverse problems associated with RNA complexes in RNAi. Among other things, this application provides novel compounds and compositions for making and using RNA complexes that have improved potency and nuclease stability, and have reduced or eliminated "off-target" effect and/or cytokine induction.

BRIEF SUMMARY

The present disclosure provides RNA complexes with one or more hydroxymethyl substituted monomers incorporated into an RNA strand to be used in relation to RNA-guided gene regulation or gene analysis, in particular RNA interference. Thus, it is an object of the present disclosure to provide RNA complexes, which have reduced off target effects as compared to the RNA complexes typically used. Another object is to provide RNA complexes with reduced interferon response. Still another object is to provide RNA complexes with improved properties with regard to stability towards enzymatic degradation in cell cultures or in vivo. Still another object is to provide RNA complexes that display enhanced gene regulatory function, e.g. gene silencing effect, in cell cultures or in vivo, relative to the unmodified RNA complexes. Yet further objects are to provide RNA complexes that are targeted towards specific organs or tissue, and that are capable of penetrating the cell membrane. The present disclosure also provides monomers suitable for incorporation of hydroxymethyl substituted monomers into oligonucleotides and methods for their synthesis.

In one aspect, the disclosure provide for a nucleic acid comprising a sense strand and an antisense strand, and a double-stranded region having from 15 to 24 base pairs, wherein any one or more of the last three positions at the 5'-end of the sense strand is occupied by the same or different hydroxymethyl substituted nucleomonomer.

In another aspect, the nucleic acid further comprises that one or both of the last two positions of the 3'-end of the sense strand are occupied by the same or different hydroxymethyl substituted nucleomonomer.

In yet another aspect, the nucleic acid further comprises that one or both of the last two positions of the 3'-end of the antisense strand is occupied by the same or different hydroxymethyl substituted nucleomonomer.

In another aspect, the disclosure provide for a nucleic acid comprising a sense strand and an antisense strand, and a double-stranded region having from 15 to 24 base pairs, wherein one or more of positions 5, 6, 7 and 8 of the antisense strand are occupied by the same or different hydroxymethyl substituted nucleomonomer, wherein the positions of the antisense strand are numbered beginning with position 1 at the 5' end of the antisense strand.

In another aspect, the nucleic acid further comprises that one or both of the last two positions of the 3'-end of the sense strand are occupied by the same or different hydroxymethyl substituted nucleomonomer.

In yet another aspect, the nucleic acid further comprises that one or both of the last two positions of the 3'-end of the antisense strand is occupied by the same or different hydroxymethyl substituted nucleomonomer.

In another aspect, the nucleic acid has a double-stranded region of 19 or 20 base pairs.

In another aspect, the sense strand and the antisense strand are each 21 or 22 nucleomonomers in length.

In another aspect, the nucleic acid has a blunt end or a 3'-end overhang.

In another aspect, the antisense strand has a region of at least 15 contiguous nucleomonomers corresponding to any 15 contiguous nucleomonomers of SEQ ID NOs: 12, 34, 56, 78, 100, 124, or 147. In a related aspect, the antisense strand has a region of at least 15, 16, 17, 18, 19, 20, 21, 22, 23, or 24 contiguous nucleomonomers corresponding to any 15, 16, 17, 18, 19, 20, 21, 22, 23, or 24 contiguous nucleomonomers of SEQ ID NOs: 12, 34, 56, 78, 100, 124, or 147.

In one aspect, this disclosure provides for a nucleic acid comprising a sense strand and an antisense strand, and a double-stranded region having from 25 to 40 base pairs, wherein the last position of the 3'-end of the antisense strand and the last position of the 3'-end of the sense strand are occupied by the same or different hydroxymethyl substituted nucleomonomer.

In another aspect, the last two positions of the 3'-end of the antisense strand are occupied by the same or different hydroxymethyl substituted nucleomonomer.

In one aspect, this disclosure provide for a nucleic acid comprising a sense strand and an antisense strand, and a double-stranded region having from 25 to 40 base pairs, wherein one or more of positions 21, 22 and 23 of the sense strand is occupied by the same or different hydroxymethyl substituted nucleomonomer, wherein the positions of the sense strand are numbered beginning with position 1 at the 5'-end of the sense strand.

In one aspect, this disclosure provide for a nucleic acid comprising a sense strand and an antisense strand, and a double-stranded region having from 25 to 40 base pairs, wherein one or more of positions 18, 19, 20, 21, and 22 of the antisense strand are occupied by the same or different hydroxymethyl substituted nucleomonomer, wherein the positions of the sense strand are numbered beginning with position 1 at the 3'-end of the antisense strand.

In another aspect, the nucleic acid further comprises that one or both of the last two positions of the 3'-end of the antisense strand are occupied by the same or different hydroxymethyl substituted nucleomonomer.

In another aspect, the nuclei acid further comprises that one or both of the last two positions of the 3'-end of the sense strand are occupied by the same or different hydroxymethyl substituted nucleomonomer.

In another aspect, the antisense strand has a region of at least 15 contiguous nucleomonomers corresponding to any 15 contiguous nucleomonomers of SEQ ID NOs: 169, 185, 201, 217, or 233.

In a related aspect, the antisense strand has a region of at least 15, 16, 17, 18, 19, 20, 21, 22, 23, 24, 25, 26, 27, 28, 29, 30, 31, 32, 33, 34, 35, 36, 37, 38, 39 or 40 contiguous nucleomonomers corresponding to any 15, 16, 17, 18, 19, 20, 21, 22, 23, 24, 25, 26, 27, 28, 29, 30, 31, 32, 33, 34, 35, 36, 37, 38, 39 or 40 contiguous nucleomonomers of SEQ ID NOs: 169, 185, 201, 217, or 233.

In another aspect, the hydroxymethyl substituted nucleomonomer is a 2'-3'-seco-nucleomonomer.

In another aspect, the hydroxymethyl substituted nucleomonomer is selected from monomers D, F, G, H, I, or J:

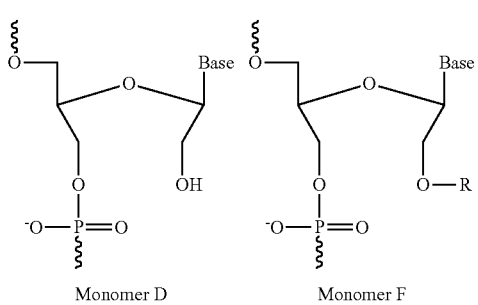

Monomer D         Monomer F

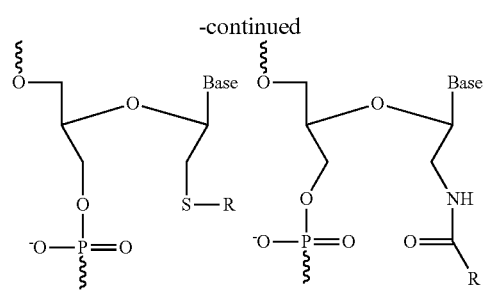

Monomer G         Monomer H

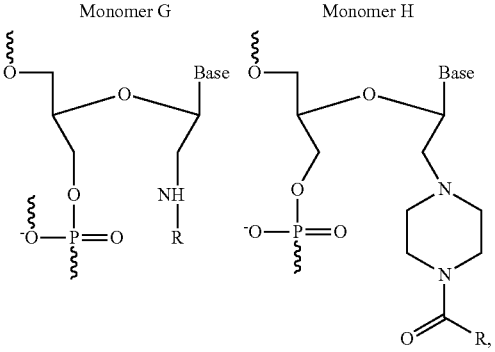

Monomer I         Monomer J wherein R is selected from the group consisting of a hydrogen, an alkyl group, a cholesterol derivative, a fluorophore, a polyamine, a fatty acid, an amino acid, a saccharide and a polypeptide, wherein Base is any purine, pyrimidine, or derivative or analogue thereof.

In another aspect, the nucleic acid further comprises a nucleotide analogue selected from the group consisting of 2'-O-alkyl-RNA monomers, 2'-amino-DNA monomers, 2'-fluoro-DNA monomers, LNA monomers, PNA monomers, HNA monomers, ANA monomers, FANA monomers, CeNA monomers, ENA monomers, DNA monomers, and INA monomers.

In one aspect, the disclosure provide for a method of reducing expression of a gene in a cell comprising preparing a nucleic acid as described herein and treating the cell with the nucleic acid.

In one aspect, the disclosure provides for a method for treating a disease in a human, the disease being selected from inflammatory diseases including rheumatoid arthritis, metabolic diseases including hypercholesterolemia, liver disease, encephalitis, bone fracture, heart disease, viral disease including hepatitis and influenza, and cancer, comprising preparing a nucleic acid described herein and administering the nucleic acid to the human.

In one aspect, the disclosure provide for a use of a nucleic acid according as described herein in the preparation of a medicament for treating a disease including inflammatory diseases including rheumatoid arthritis, metabolic diseases including hypercholesterolemia, liver disease, encephalitis, bone fracture, heart disease, viral disease including hepatitis and influenza, and cancer.

DETAILS DESCRIPTION

Specific features described in one aspect of the disclosure also apply to other aspects of the disclosure. For example, features described with regards to RNA complexes may also apply to the oligonucleotides, and RNA duplexes where appropriate.

RNA complexes in the form of siRNA duplexes or single stranded RNA can mediate various modifications of target nucleic acids in the cell. In this process, the antisense strand of the complex acts as a guide, as the antisense strand can hybridise to target nucleic acids that have stretches of sequence complementary to the antisense strand.

Before targeting of a target nucleic acid, the antisense strand is often incorporated into an RNA guided protein complex (RGPC), which can act upon the target nucleic acid. One example of a RNA guided protein complex is the RNA Induced Silencing Complex (RISC). It is believed that other such RGPCs exist and that the RNA complexes of the present disclosure will also be of advantage, when used with these other RGPCs or even without interacting with any RGPCs.

One object of the present disclosure is to stabilize the RNA complexes towards nucleolytic degradation in biological media (serum, in vivo, in cell cultures).

Another object of the present disclosure is to improve the gene silencing effect of a double stranded RNA complex. This improvement can, e.g. relate to increased potency, reduced off-target effects, reduced immune stimulation, increased stability for storage, increased stability in biological media like serum etc., increased duration of action and improved pharmacokinetic properties, all relative to the native unmodified RNA complex.

Yet another object of the present disclosure is to improve the gene silencing effect of a single stranded RNA oligonucleotide. This improvement can, e.g., relate to increased potency, reduced off-target effects, reduced immune stimulation, increased stability for storage, increased stability in biological media like serum etc., increased duration of action and improved pharmacokinetic properties, all relative to the native unmodified RNA complex.

Another object of the disclosure is to ensure sufficient stability of an RNA complex in biological media. Thus it is an object to provide RNA complexes that display enhanced gene regulatory function, e.g. gene silencing effect, in cell cultures or in vivo, relative to unmodified RNA complexes.

Figure 1:
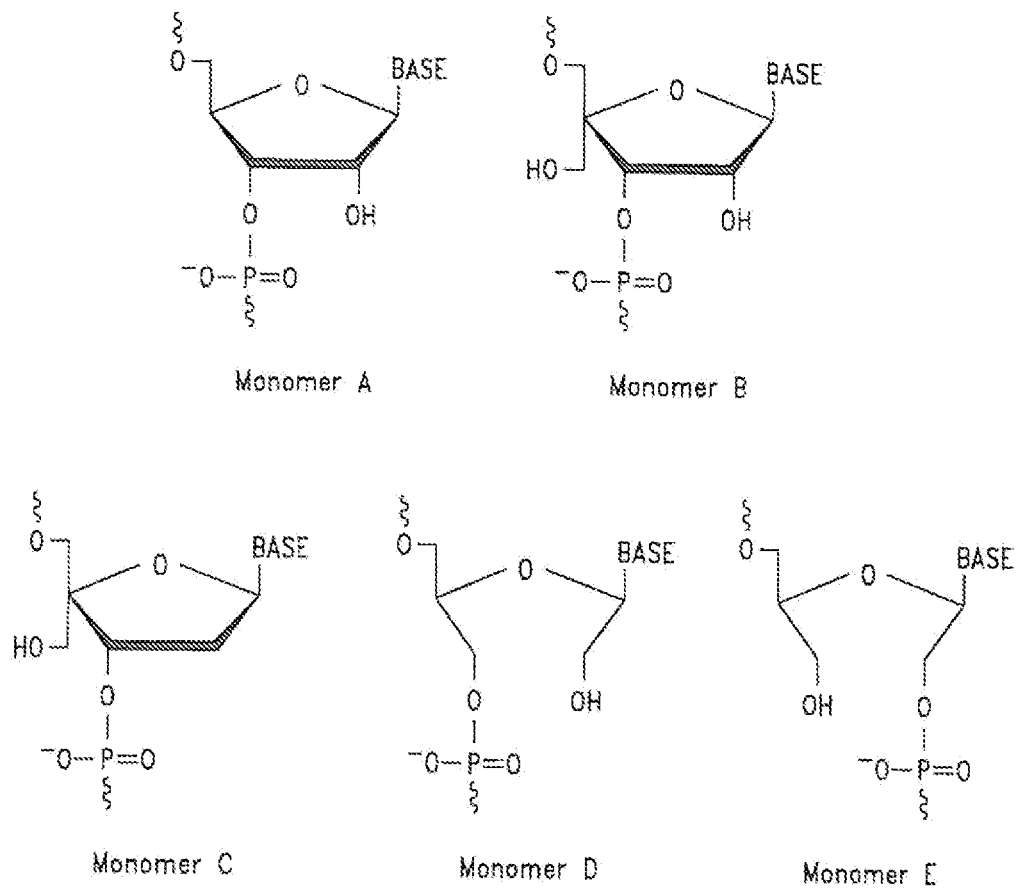
FIG. 1: Examples of the different architectures of the hydroxymethyl substituted nucleomonomers that are incorporated in the RNA complexes are shown. Monomer A is shown for comparison and is a natural RNA monomer with its ribose scaffold. The characteristic of Monomers B-E that are comprised in the RNA complexes of the disclosure is that they contain a substituent that is a hydroxymethyl group ("the free hydroxymethyl group"). The free hydroxymethyl group is for example attached at the C4' atom of a cyclic ribose scaffold or the C1' atom of an acyclic ribose-based scaffold. The hydroxymethyl substituted nucleomonomers of the disclosure contain other oxygen atoms that are each attached to a phosphorus atom and thus partake in the formation of internucleotide linkages (see FIG. 1). One or more of these other oxygen atoms can be part of a hydroxy group which is the case when one or more of the hydroxymethyl substituted nucleomonomers of the RNA complexes of the disclosure is (are) positioned at the 3'- or 5'-end of an RNA strand. When one of the hydroxymethyl substituted nucleomonomers of the RNA complexes of the disclosure is positioned at the 3'-end and/or the 5'-end of the RNA strands, a hydroxyl group of this monomer can be phosphorylated, as can be the case for any terminally positioned natural RNA monomer. To the hydroxymethyl substituted nucleomonomers of the disclosure is attached a nucleobase like uracil, thymine, cytosine, 5-methylcytosine, adenine, guanine or any other known natural or synthetic nucleobase or nucleobase analogue (designated as "Base" in FIG. 1).

An RNA strand of an RNA complex of the disclosure may comprise natural RNA nucleotides, RNA modifications known to be compatible with gene silencing activity [Nawrot and Sipa, Curr. Topics Med. Chem. 2006, 6, 913-925], and the hydroxymethyl substituted monomers (FIG. 1). Phosphodiester linkages may connect the individual monomers, but modified linkages like phosphorothioate linkages and other linkages known to a person skilled in the field [Nawrot and Sipa, Curr. Topics Med. Chem. 2006, 6, 913-925] may be used instead.

The RNA complexes disclosed herein may comprise two strands that together constitute an siRNA duplex composed of an antisense strand (the antisense strand is also herein referred to as the guide strand) and a passenger strand (the passenger strand is also herein referred to as the sense strand), a single stranded RNA molecule (e.g. antisense RNA), a functional RNA (fRNA), or non-coding RNA (ncRNA), such as small temporal RNA (stRNA), microRNA (miRNA), small nuclear RNA (snRNA), short interfering RNA (siRNA), small nucleolar RNA (snRNA), ribosomal RNA (rRNA), transfer RNA (tRNA) and precursor RNAs thereof, an RNAa molecule, a microRNA mimicking molecule is also considered herein as an RNA complex of the disclosure, as is a single stranded antisense molecule that for example is useful for targeting microRNAs.

In the embodiments of the disclosure, the RNA complex comprises one or more hydroxymethyl substituted nucleomonomer(s) (see FIG. 1). Hereunder as one such example is a hydroxymethyl substituted nucleomonomer, more preferably an acyclic monomer selected from the group consisting of monomers D-J. Thus, the embodiments described in the first aspect with regards to hydroxymethyl substituted nucleomonomers will apply for other embodiments relating to hydroxymethyl substituted nucleomonomers.

In one preferred embodiment of the disclosure, the RNA complex comprising one or more hydroxymethyl substituted nucleomonomer(s) is a single stranded RNA construct.

In one preferred embodiment of the disclosure, the RNA complex comprising one or more hydroxymethyl substituted nucleomonomer(s) is a single stranded RNA construct that is able to inhibit gene expression by acting as a single stranded antisense molecule.

In one preferred embodiment of the disclosure, the RNA complex comprising one or more hydroxymethyl substituted nucleomonomer(s) is a single stranded RNA construct that functionally mimics a microRNA.

In one preferred embodiment of the disclosure, the RNA complex comprising one or more hydroxymethyl substituted nucleomonomer(s) is an siRNA construct.

Accordingly, in one embodiment, the antisense strand of an siRNA construct comprises one or more hydroxymethyl substituted nucleomonomer(s).

In another embodiment, the passenger strand of an siRNA construct comprises one or more hydroxymethyl substituted nucleomonomer(s).

In yet another embodiment, a first and second RNA molecule of a nicked passenger strand of an siRNA construct each contain one or more hydroxymethyl substituted nucleomonomer(s).

In one aspect, the disclosure provide for a nucleic acid comprising a sense strand and an antisense strand, and a double-stranded region having from 15 to 24 base pairs, wherein any one or more of the last three positions at the 5'-end of the sense strand is occupied by the same or different hydroxymethyl substituted nucleomonomer.

In another aspect, the nucleic acid further comprises that one or both of the last two positions of the 3'-end of the sense strand are occupied by the same or different hydroxymethyl substituted nucleomonomer.

In yet another aspect, the nucleic acid further comprises that one or both of the last two positions of the 3'-end of the antisense strand is occupied by the same or different hydroxymethyl substituted nucleomonomer.

In another aspect, the disclosure provide for a nucleic acid comprising a sense strand and an antisense strand, and a double-stranded region having from 15 to 24 base pairs, wherein one or more of positions 5, 6, 7 and 8 of the antisense strand are occupied by the same or different hydroxymethyl substituted nucleomonomer, wherein the positions of the antisense strand are numbered beginning with position 1 at the 5' end of the antisense strand.

In another aspect, the nucleic acid further comprises that one or both of the last two positions of the 3'-end of the sense strand are occupied by the same or different hydroxymethyl substituted nucleomonomer.

In yet another aspect, the nucleic acid further comprises that one or both of the last two positions of the 3'-end of the antisense strand is occupied by the same or different hydroxymethyl substituted nucleomonomer.

In another aspect, the nucleic acid has a double-stranded region of 19 or 20 base pairs.

In another aspect, the sense strand and the antisense strand are each 21 or 22 nucleomonomers in length.

In another aspect, the nucleic acid has a blunt end or a 3'-end overhang.

In another aspect, the antisense strand has a region of at least 15 contiguous nucleomonomers corresponding to any 15 contiguous nucleomonomers of SEQ ID NOs: 12, 34, 56, 78, 100, 124, or 147.

In a related aspect, the antisense strand has a region of at least 15, 16, 17, 18, 19, 20, 21, 22, 23, or 24 contiguous nucleomonomers corresponding to any 15, 16, 17, 18, 19, 20, 21, 22, 23, or 24 contiguous nucleomonomers of SEQ ID NOs: 12, 34, 56, 78, 100, 124, or 147.

In one aspect, this disclosure provides for a nucleic acid comprising a sense strand and an antisense strand, and a double-stranded region having from 25 to 40 base pairs, wherein the last position of the 3'-end of the antisense strand and the last position of the 3'-end of the sense strand are occupied by the same or different hydroxymethyl substituted nucleomonomer.

In another aspect, the last two positions of the 3'-end of the antisense strand are occupied by the same or different hydroxymethyl substituted nucleomonomer.

In one aspect, this disclosure provide for a nucleic acid comprising a sense strand and an antisense strand, and a double-stranded region having from 25 to 40 base pairs, wherein one or more of positions 21, 22 and 23 of the sense strand is occupied by the same or different hydroxymethyl substituted nucleomonomer, wherein the positions of the sense strand are numbered beginning with position 1 at the 5'-end of the sense strand.

In one aspect, this disclosure provide for a nucleic acid comprising a sense strand and an antisense strand, and a double-stranded region having from 25 to 40 base pairs, wherein one or more of positions 18, 19, 20, 21, and 22 of the antisense strand are occupied by the same or different hydroxymethyl substituted nucleomonomer, wherein the positions of the sense strand are numbered beginning with position 1 at the 3'-end of the antisense strand.

In another aspect, the nucleic acid further comprises that one or both of the last two positions of the 3'-end of the antisense strand are occupied by the same or different hydroxymethyl substituted nucleomonomer.

In another aspect, the nucleic acid further comprises that one or both of the last two positions of the 3'-end of the sense strand are occupied by the same or different hydroxymethyl substituted nucleomonomer.

In another aspect, the antisense strand has a region of at least 15 contiguous nucleomonomers corresponding to any 15 contiguous nucleomonomers of SEQ ID NOs: 169, 185, 201, 217, or 233.

In a related aspect, the antisense strand has a region of at least 15, 16, 17, 18, 19, 20, 21, 22, 23, 24, 25, 26, 27, 28, 29, 30, 31, 32, 33, 34, 35, 36, 37, 38, 39 or 40 contiguous nucleomonomers corresponding to any 15, 16, 17, 18, 19, 20, 21, 22, 23, 24, 25, 26, 27, 28, 29, 30, 31, 32, 33, 34, 35, 36, 37, 38, 39 or 40 contiguous nucleomonomers of SEQ ID NOs: 169, 185, 201, 217, or 233.

In another aspect, the hydroxymethyl substituted nucleomonomer is a 2'-3'-seco-nucleomonomer.

In another aspect, the hydroxymethyl substituted nucleomonomer is selected from monomers D, F, G, H, I, or J:

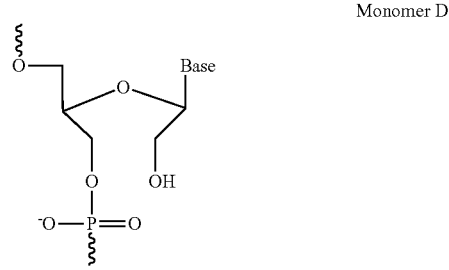

Monomer D

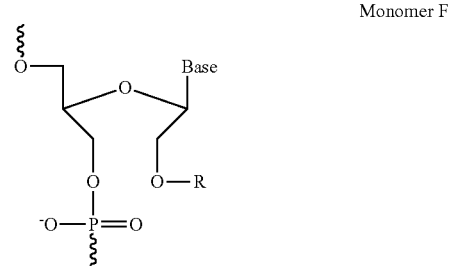

Monomer F

-continued

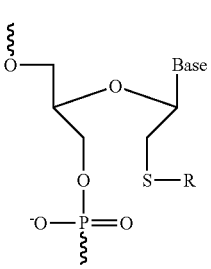

Monomer G

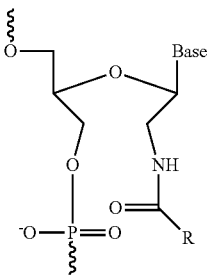

Monomer H

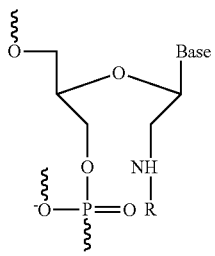

Monomer I

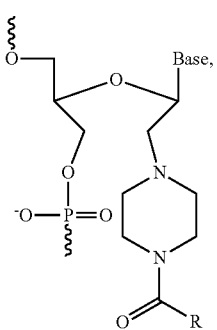

Monomer J wherein R is selected from the group consisting of a hydrogen, an alkyl group, a cholesterol derivative, a fluorophore, a polyamine, a fatty acid, an amino acid, a saccharide, and a polypeptide, wherein Base is any purine, pyrimidine, or derivative or analogue thereof.

In another aspect, the nucleic acid further comprises a nucleotide analogue selected from the group consisting of 2'-O-alkyl-RNA monomers, 2'-amino-DNA monomers, 2'-fluoro-DNA monomers, LNA monomers, PNA monomers, HNA monomers, ANA monomers, FANA monomers, CeNA monomers, ENA monomers, DNA monomers, and INA monomers.

In one aspect, the disclosure provide for a method of reducing expression of a gene in a cell comprising preparing a nucleic acid as described herein and treating the cell with the nucleic acid.

In one aspect, the disclosure provides for a method for treating a disease in a human, the disease being selected from inflammatory diseases including rheumatoid arthritis, metabolic diseases including hypercholesterolemia, liver disease, encephalitis, bone fracture, heart disease, viral disease including hepatitis and influenza, and cancer, comprising preparing a nucleic acid described herein and administering the nucleic acid to the human.

In one aspect, the disclosure provide for a use of a nucleic acid according as described herein in the preparation of a medicament for treating a disease including inflammatory diseases including rheumatoid arthritis, metabolic diseases including hypercholesterolemia, liver disease, encephalitis, bone fracture, heart disease, viral disease including hepatitis and influenza, and cancer.

In one aspect, the disclosure provides for a double-stranded RNA (dsRNA) that downregulates the expression of a gene, the dsRNA comprising a sense strand and an antisense strand, a double-stranded region having from 15 to 24 base pairs, and wherein one or more hydroxymethyl substituted nucleomonomer(s) are at one or more of positions 1 or 2 of the sense strand counting from the 5'-end of the sense strand.

For example purposes only, the positions of the sense strand may be described as follows where X represents a nucleomonomer (nucleoside or hydroxymethyl substituted nucleomonomer) and the number represents the position of that nucleomonomer in the strand. For a RISC length RNA complex, n may be from 5 to 14 (or 5, 6, 7, 8, 9, 10, 11, 12, 13 or 14), and for a Dicer length RNA complex, n may be from 15 to 30 (or 15, 16, 17, 18, 19, 20, 21, 22, 23, 24, 25, 26, 27, 28, 29 or 30). The same procedure for determining the position of a nucleomonomer in sense strand may be applied to the antisense strand.

5' X1-X2-X3-X4-X5-X6-X7-X8-X9-X10-$X_n$ 3'

In this example, nucleomonomer X1 occupies position 1, X2 occupies position 2.

In a related aspect, the last two nucleomonomers of the 3'-end of the antisense strand and the last two nucleomonomers of the 3'-end of the sense strand are hydroxymethyl substituted nucleomonomers.

For example purposes only, the position of the hydroxymethyl substituted nucleomonomers in each of the sense strand and the antisense strand may be represented as follows where X represents a nucleomonomer (nucleoside or hydroxymethyl substituted nucleomonomer) and n represents the position. For a RISC length RNA complex, n may be from 13 to 22 (or 13, 14, 15, 16, 17, 18, 19, 20, 21 or 22), and for a Dicer length RNA complex, n may be from 23 to 38 (or 23, 24, 25, 26, 27, 28, 29, 30, 31, 32, 33, 34, 36, 37 or 38).

5'$X_n$-$X_{(n+1)}$-$X_{(n+2)}$ 3'

In this example, the last nucleomonomer is represented by position $X_{(n+2)}$, the next to last nucleomonomer is represented by position $X_{(n+1)}$, and the last two nucleomonomers of the 3'-end of the strand (whether the sense strand or the antisense strand) are represented by $X_{(n+1)}$ and $X_{(n+2)}$.

In a related aspect, one or more hydroxymethyl substituted nucleomonomer(s) are at one or more of positions 5, 6, 7 or 8 counting from the 5'-end of the antisense strand.

In a related aspect, one or more hydroxymethyl substituted nucleomonomer(s) are at position 7 counting from the 5'-end of the antisense strand.

In a related aspect, the double-stranded region has 19 or 20 base pairs. In a related aspect, the sense strand and the antisense strand each have 21 or 22 nucleomonomers.

In a related aspect, the dsRNA has a 3'-end overhang.

In a related aspect, the dsRNA has a blunt end.

In another aspect, the disclosure provides a double-stranded RNA (dsRNA) that downregulates the expression of a gene, the dsRNA comprising a sense strand and an antisense strand, a double-stranded region having from 25 to 40 base pairs, and wherein the last two nucleomonomers of the 3'-end of the antisense strand and the last nucleomonomer of the 3'-end of the sense strand are hydroxymethyl substituted nucleomonomers.

In another aspect, the disclosure provides a double-stranded RNA (dsRNA) that downregulates the expression of a gene, the dsRNA comprising a sense strand and an antisense strand, a double-stranded region having from 25 to 40 base pairs, and wherein one or more hydroxymethyl substituted nucleomonomer(s) are at one or more of positions of the sense strand that inhibit processing of the dsRNA by a Dicer enzyme.

In a related aspect, one or more hydroxymethyl substituted nucleomonomer(s) are at one or more of positions 21, 22 or 23 of the sense strand counting from the 5'-end of the sense strand.

In a related aspect, one or more hydroxymethyl substituted nucleomonomer(s) are at one or more of positions 18, 19, 20 21 or 22 of the antisense strand counting from the 3'-end of the antisense strand.

In one aspect of the disclosure, the number of hydroxymethyl substituted nucleomonomers in the antisense strand is 10. In other embodiments of the disclosure, the number of hydroxymethyl substituted nucleomonomer(s) in the antisense strand is 9, 8, 7, 6, 5, 4, 3, 2 or 1, respectively.

In another aspect, all nucleotides of the antisense strand are hydroxymethyl substituted nucleomonomers.

In one aspect of the disclosure, all hydroxymethyl substituted nucleomonomers in the antisense strand are present in positions 1, 2, 3, 4, 5, 6, 7, and/or 8, wherein the positions are counted from the 5' end of the antisense strand. Even more preferably, the hydroxymethyl substituted nucleomonomers in the antisense strand are present in positions 2, 3, 4, 5, 6, and/or 7, counted from the 5' end of the antisense strand or in the corresponding to the so-called seed region of a microRNA. In another aspect, the hydroxymethyl substituted nucleomonomers in the antisense strand are present in positions 4, 5, 6, 7 and/or 8, counted from the 5' end of the antisense strand. In another aspect, the hydroxymethyl substituted nucleomonomers in the antisense strand are present in positions 6, 7 and/or 8, counted from the 5' end of the antisense strand. In another aspect, the hydroxymethyl substituted nucleomonomers in the antisense strand are present in positions in the antisense strand that reduce the microRNA activity of the RNA compared to the same RNA without hydroxymethyl substituted nucleomonomers. Thus, presence of hydroxymethyl substituted nucleomonomers in the aforementioned regions may prevent the antisense strand from acting as a microRNA, which reduces off target effects when the antisense strand is intended to function as siRNA.

In a preferred embodiment, at least one hydroxymethyl substituted nucleomonomer is present in any one of positions 9, 10, 11, 12, 13, 14, 15, and/or 16, wherein the positions are counted from the 5'-end of the antisense strand. Even more preferred is hydroxymethyl substituted nucleomonomers present in any one of positions 9, 10, 11, 12, 13, 14, 15, and/or 16, wherein the positions are counted from the 5' end of the antisense strand. In another embodiment, hydroxymethyl substituted nucleomonomers in the antisense strand is present in all of positions 9, 10, 11, 12, 13, 14, 15, and/or 16. In one embodiment, hydroxymethyl substituted nucleomonomer are only present in regions 9, 10, 11, 12, 13, 14, 15, and/or 16 and not in the rest of the antisense strand.

Even more preferably, the hydroxymethyl substituted nucleomonomers in the antisense strand is present in position 9, 10, and/or 11, counted from the 5' end of the antisense strand, and preferably, not in the rest of the oligonucleotide.

In another aspect, the hydroxymethyl substituted nucleomonomers in the antisense strand are present in positions in the antisense strand that enhance the microRNA activity of the RNA compared to the same RNA without hydroxymethyl substituted nucleomonomers. The presence of hydroxymethyl substituted nucleomonomers in the aforementioned regions may induce the antisense strand to act as a microRNA, i.e. ensure that the siRNA effect will be minimal and the microRNA effect much higher.

Likewise, in another embodiment of the disclosure, the number of hydroxymethyl substituted nucleomonomers in the passenger strand of an siRNA complex of the disclosure is 10. In other embodiments of the disclosure, the number of hydroxymethyl substituted nucleomonomers in the passenger strand of an siRNA complex of the disclosure is 9, 8, 7, 6, 5, 4, 3, 2 or 1, respectively.

In another embodiment, all nucleotides of the passenger strand of an siRNA complex of the disclosure are hydroxymethyl substituted nucleomonomers.

In certain aspects, the sense (passenger strand) of a dsRNA comprises one or more hydroxymethyl substituted nucleomonomer(s). In certain aspects, the sense (passenger strand) of a dsRNA comprises 1, 2, 3, 4, 5, 6, 7, 8, 9 or 10 hydroxymethyl substituted nucleomonomer(s). In certain aspects, the entire sense (passenger strand) of a dsRNA comprises hydroxymethyl substituted nucleomonomer(s).

In certain aspects, a hydroxymethyl substituted nucleomonomer in the sense strand is present in positions 1, 2, 3, 4, 5, 6, 7, and/or 8 wherein the positions are counted from the 5'-end of the sense strand. In certain aspects, a hydroxymethyl substituted nucleomonomer in the sense strand is present in positions 1, 2, 3, and/or 4 wherein the positions are counted from the 5'-end of the sense strand. In certain aspects, a hydroxymethyl substituted nucleomonomer in the sense strand is present in positions 1, 2 and/or 3 wherein the positions are counted from the 5'-end of the sense strand. In certain aspects, a hydroxymethyl substituted nucleomonomer in the sense strand is present in positions 5, 6, 7, and/or 8 wherein the positions are counted from the 5'-end of the sense strand. In certain aspects, a hydroxymethyl substituted nucleomonomer in the sense strand is present in positions 7 and/or 8 wherein the positions are counted from the 5'-end of the sense strand. In certain aspects, hydroxymethyl substituted nucleomonomers in the sense strand are present in positions in the sense strand of an RNA that reduce the RNAi activity of the sense strand of the RNA compared to the same RNA without hydroxymethyl substituted nucleomonomers.

In certain aspects, a hydroxymethyl substituted nucleomonomer in the sense strand is present in positions 9, 10, 11, 12, 13, 14, 15, and/or 16 wherein the positions are counted from the 5'-end of the sense strand. In certain aspects, a hydroxymethyl substituted nucleomonomer in the sense strand is present in positions 9, 10, and/or 11, wherein the positions are counted from the 5'-end of the sense strand.

In certain aspects, a hydroxymethyl substituted nucleomonomer in the sense strand is present in positions 19, 20, 21, 22, 23, 24, 25, 26, 27, 28, 29, 30, 31 and/or 32 wherein the positions are counted from the 5'-end of the sense strand. In certain aspects, a hydroxymethyl substituted nucleomonomer in the sense strand is present in positions 1, 2, 3, 4, 5, 6, 7, 8, 9 and/or 10, wherein the positions are counted from the 3'-end of the sense strand.

In one embodiment, both the antisense strand and the passenger strand of an siRNA complex of the disclosure contain one or more hydroxymethyl substituted nucleomonomer(s).

In one aspect, the present disclosure provides an RNA complex capable of mediating nucleic acid modifications of a target nucleic acid. Such RNA complex may e.g. be a siRNA, microRNA or microRNA precursor (pre-microRNA).

The RNA complex of an siRNA complex of the disclosure comprises a core double stranded region comprising an antisense strand and a passenger strand that is hybridized to the antisense strand.

A target nucleic acid as referred to in the present context is a nucleic acid, which has significant complementarity to the antisense strand of the complex. Preferably, complementarity is perfect over a stretch of several nucleotides.

Thus, in one embodiment, complementarity is perfect over a stretch of 25 nucleotides.

In other embodiments, complementarity is perfect over a stretch of 24 nucleotides, 23 nucleotides, 22 nucleotides, 21 nucleotides, 20 nucleotides, 19 nucleotides, 18 nucleotides, 17 nucleotides, 16 nucleotides, 15 nucleotides, 14 nucleotides, 13 nucleotides, 12 nucleotides, 11 nucleotides, 10 nucleotides, 9 nucleotides, 8 nucleotides, 7 nucleotides or 6 nucleotides, respectively.

In one embodiment, the stretch of complementarity comprises 1 mismatch. In other embodiments, the stretch of complementarity comprises 2 mismatches, 3 mismatches or 4 mismatches, respectively. A mismatch of 1 is a region in the stretch of complementarity where a base pair cannot form, e.g. when G is opposite to A. When more mismatches are present they may be adjacent to each other or they may be spaced in different regions of the stretch of complementarity.

The RNA complex of an siRNA complex of the disclosure comprises in a preferred embodiment a core double-stranded region, which is a substantially double-stranded region. Single-stranded regions in the RNA complex are primarily related to overhangs of the complex.

Thus, in one embodiment, the double-stranded region of an siRNA complex of the disclosure comprises 1 mismatch. In other embodiments, the double-stranded region comprises 2 mismatches, 3 mismatches and 4 mismatches, respectively.

As used herein, the term "target nucleic acid" encompasses any RNA/DNA that would be subject to modulation guided by the antisense strand, such as targeted cleavage or steric blockage. The target RNA/DNA could, for example be genomic DNA, genomic viral RNA, mRNA, a pre-mRNA, or a non-coding RNA.

As used herein, the term "linked" encompasses a covalent linkage either directly between two chemical entities (e.g., RNA and an hydroxymethyl substituted nucleomonomer), or indirectly between two chemical entities, for example via a linker.

As used herein, the term "overhang" (e.g., 3'-end overhang or 3' overhang) means an unpaired region of an RNA complex with may contain all nucleotides, non-nucleotides (e.g., hydroxymethyl substituted nucleomonomers), or a combination of nucleotides and non-nucleotides.

As used herein, the term "nucleomonomer" means a moiety comprising (1) a base covalently linked to (2) a second moiety. Nucleomonomers can be linked to form oligomers that bind to target or complementary base sequences in nucleic acids in a sequence specific manner.

As used herein, the terms "hydroxymethyl substituted nucleomonomer", "hydroxymethyl nucleomonomer", "hydroxymethyl monomer", "acyclic nucleomonomer", "acyclic monomer", "acyclic hydroxymethyl substituted nucleomonomer" may be used interchangeably throughout.

As used herein, the terms "RISC length" or "RISC length RNA complex" means a nucleic acid molecule having less than 25 base pairs.

As used herein the terms "Dicer length" or "Dicer length RNA complex" means a nucleic acid molecule have 25 or more base pairs, generally, from 25 to 40 base pairs.

A preferred target nucleic acid of the disclosure is mRNA. Accordingly, in one embodiment the nucleic acid modification mediated by the RNA complex is RNA interference (RNAi). In a preferred embodiment, RNAi mediates degradation of the mRNA. In another preferred embodiment, RNAi mediates translational inhibition of the mRNA. In another embodiment, the RNAi mediates both translational inhibition and degradation of the mRNA.

In other preferred embodiments, the target nucleic acid is a non-coding RNA, e.g. a tRNA, miRNA, snRNA, snoRNA, OSU (unusually small RNAs) or an rRNA.

In still another embodiment, the target nucleic acid is genomic DNA. In such embodiments, preferred nucleic acid modifications include DNA methylation and DNA deletion.

The size of the RNA complex of the disclosure can be varied while still fulfilling one or more objects of the disclosure. This e.g. applies where the particular object is reduced off-target effect.

Thus, the core double-stranded region of an siRNA complex of the disclosure may comprise a number of base pairs selected from the group of 10 base pairs, 11 base pairs, 12 base pairs, 13 base pairs, 14 base pairs, 15 base pairs, 16 base pairs, 17 base pairs, 18 base pairs, 19 base pairs, 20 base pairs, 21 base pairs, 22 base pairs, 23 base pairs, 24 base pairs and 25 base pairs, 26 base pairs, 27 base pairs, 28 base pairs, 29 base pairs, 30 base pairs, 35 base pairs, 40 base pairs, 42 base pairs, 45 base pairs, 50 base pairs, 55 base pairs, 60 base pairs or 62 base pairs.

In one embodiment, the core double stranded region of an siRNA complex of the disclosure comprises from 15 to 40 base pairs.

In another preferred embodiment, the core double stranded region of an siRNA complex of the disclosure comprises 18 to 22 base pairs or 25 to 30 base pairs.

In one embodiment, the core double stranded region of an siRNA complex of the disclosure is even longer than 40 base pairs, although it is known that in some cells, the introduction of longer double stranded RNA complex may induce an interferon dependent non-specific response. In one such embodiment, it is contemplated that the complex is processed to shorter double-stranded RNA complexes before engaging with a RGPC. An RNase III like enzyme such as DICER may execute processing. Dicer also processes double stranded RNA shorter than 40 base pairs and such RNA complexes (referred to as Dicer substrates) have various advantages as compared to siRNA that enters RISC without processing. Hence, in one embodiment, the RNA complexes of the disclosure are Dicer substrates.

In another embodiment, the RNA complex is single stranded and has no double stranded region.

In yet another embodiment, the RNA complex is single stranded but folds such that it contains one or more double stranded regions. Such embodiments are useful e.g. for mimicking microRNAs and their functions.

In yet another embodiment, the core double stranded region of an siRNA complex of the disclosure is shorter than 10 base pairs and thus comprises from one to nine base pairs.

In one embodiment of the disclosure, the core double stranded region of the RNA complex is comprised by more than two RNA strands.

In one embodiment of the disclosure, the core double stranded region of the RNA complex is comprised by three RNA strands.

In another embodiment of the disclosure, the core double stranded region of the RNA complex is comprised by four or more RNA strands.

In a preferred embodiment of the disclosure, the siRNA complex of the disclosure comprises overhangs. An overhang as used in the present context refers to a short single-stranded region following a double-stranded region.

In one embodiment, the antisense strand of an siRNA complex of the disclosure comprises a 3'-overhang.

In another embodiment, the passenger strand of an siRNA complex of the disclosure comprises a 3'-overhang.

In yet another embodiment, the antisense strand of an siRNA complex of the disclosure comprises a 5'-overhang.

In still another embodiment, the passenger strand of an siRNA complex of the disclosure comprises a 5'-overhang.

In a preferred embodiment, both the antisense strand and the passenger strand of an siRNA complex of the disclosure comprise a 3'-overhang.

The overhangs of an siRNA complex of the disclosure can be of varying length, without interfering with the basic function of the complex. Thus, in one embodiment the overhangs are selected from the group of overhangs with a length of 1 nucleotide, 2 nucleotides, 3 nucleotides, 4 nucleotides, 5 nucleotides, 6 nucleotides, 7 nucleotides and 8 nucleotides, and/or 1 hydroxymethyl substituted nucleomonomer, 2 hydroxymethyl substituted nucleomonomers, 3 hydroxymethyl substituted nucleomonomers, 4 hydroxymethyl substituted nucleomonomers, 5 hydroxymethyl substituted nucleomonomers, 6 hydroxymethyl substituted nucleomonomers, 7 hydroxymethyl substituted nucleomonomers and 8 hydroxymethyl substituted nucleomonomers, and combinations thereof.

Most preferred overhangs of an RNA complex of the disclosure are overhangs with a length of 1, 2 and 3 nucleotides or nucleomonomers, respectively.

In one embodiment, the overhang of the antisense strand of an RNA complex of the disclosure has the same length as the overhang of the passenger strand.

In another embodiment, the overhang of the antisense strand of an RNA complex of the disclosure does not have the same length as the overhang of the passenger strand.

In still another embodiment of an RNA complex of the disclosure, the RNA complex comprises at least one blunt end. A "blunt end" refers to an end of a double-stranded nucleic acid, which does not have any protruding nucleotides, i.e. both strands of the double-stranded nucleic acid ends at the same position.

In another embodiment, the RNA complex of the disclosure is blunt ended at both ends.

In certain aspects, the RNA complex has at least one blunt end having one or more a hydroxymethyl substituted nucleomonomer(s) covalently linked to the blunt end. In certain aspects, the dsRNA has two blunt ends each having one or more a hydroxymethyl substituted nucleomonomer(s) covalently linked to each blunt end. In certain aspects, a blunt end has 1, 2, 3, 4, 5, 6, 7, 8 or more hydroxymethyl substituted nucleomonomers covalently linked to the blunt end. In certain aspects, a blunt end has two hydroxymethyl substituted nucleomonomers covalently linked to the blunt end. In certain aspects, one or more hydroxymethyl substituted nucleomonomers are linked to the blunt end of an RNA complex with a phosphorothioate linkage.

In certain aspects, the covalent linkage is a phosphorothioate linkage.

For purposes of clarity, the following structure may be used to understand the relationship between the blunt-end of an RNA complex and the linkage of a hydroxymethyl substituted nucleomonomer (X is any nucleoside; H is a hydroxymethyl substituted nucleomonomer; n is from 13 to 38; and m is independently for each occurrence from 0 to 8). An X of the sense strand forms a base pair with an X of the antisense strand, thus forming a duplex region having a blunt end.

In the RNA complex below, hydroxymethyl substituted nucleomonomer(s) (H) may be linked (e.g., phosphodiester linkage or any other linkage disclosed herein or know to a person of ordinary skill in the art) to the 3'-end of the sense strand, or the 3'-end of the antisense strand, or to both 3'-end of the sense strand and 3'-end of the antisense strand, or the 5'-end of the sense strand, or the 5'-end of the antisense strand, or to both 5'-end of the sense strand and 5'-end of the antisense strand, or to the 3'-end of the sense strand and the 5'-end of the sense strand, or the 3'-end of the sense strand and the 5'-end of the antisense strand, or the 5'-end of the sense strand and the 3'-end of the antisense strand. More detailed embodiments are provided below.

$$5' \ (H)_m\text{-}X\text{-}(X)_n\text{-}X\text{-}(H)_m \ 3' \quad \text{Sense strand}$$
$$3' \ (H)_m\text{-}X\text{-}(X)_n\text{-}X\text{-}(H)_m \ 5' \quad \text{Antisense strand}$$

In certain aspects, the one or more a hydroxymethyl substituted nucleomonomer(s) are covalently linked to the 5'-end of the antisense strand. In certain aspects, 1, 2, 3, 4, 5, 6, 7, or 8 hydroxymethyl substituted nucleomonomer(s) are covalently linked to the 5'-end of the antisense strand.

In certain aspects, the one or more a hydroxymethyl substituted nucleomonomer(s) are covalently linked to the 3'-end of the antisense strand. In certain aspects, 1, 2, 3, 4, 5, 6, 7, or 8 hydroxymethyl substituted nucleomonomer(s) are covalently linked to the 3'-end of the antisense strand.

In certain aspects, the one or more a hydroxymethyl substituted nucleomonomer(s) are covalently linked to the 5'-end and the 3'-end of the antisense strand. In certain aspects, 1, 2, 3, 4, 5, 6, 7, or 8 hydroxymethyl substituted nucleomonomer(s) are covalently linked to the 5'-end and the 3'-end of the antisense strand.

In certain aspects, the one or more a hydroxymethyl substituted nucleomonomer(s) are covalently linked to the 5'-end of the sense strand. In certain aspects, 1, 2, 3, 4, 5, 6, 7, or 8 hydroxymethyl substituted nucleomonomer(s) are covalently linked to the 5'-end of the sense strand.

In certain aspects, the one or more a hydroxymethyl substituted nucleomonomer(s) are covalently linked to the 3'-end of the sense strand. In certain aspects, 1, 2, 3, 4, 5, 6, 7, or 8 hydroxymethyl substituted nucleomonomer(s) are covalently linked to the 3'-end of the sense strand.

In certain aspects, the one or more a hydroxymethyl substituted nucleomonomer(s) are covalently linked to the 5'-end and the 3'-end of the sense strand. In certain aspects, 1, 2, 3, 4, 5, 6, 7, or 8 hydroxymethyl substituted nucleomonomer(s) are covalently linked to the 5'-end and the 3'-end of the sense strand.

In certain aspects, the one or more a hydroxymethyl substituted nucleomonomer(s) are covalently linked to the 3'-end of the sense strand and the 3'-end of the antisense strand. In certain aspects, 1, 2, 3, 4, 5, 6, 7, or 8 hydroxymethyl substituted nucleomonomer(s) are covalently linked to the 3'-end of the sense strand and the 3'-end of the antisense strand.

In certain aspects, the one or more a hydroxymethyl substituted nucleomonomer(s) are covalently linked to the 5'-end of the sense strand and the 5'-end of the antisense strand. In certain aspects, 1, 2, 3, 4, 5, 6, 7, or 8 hydroxymethyl substituted nucleomonomer(s) are covalently linked to the 5'-end of the sense strand and the 5'-end of the antisense strand.

In certain aspects, the one or more a hydroxymethyl substituted nucleomonomer(s) are covalently linked to the 3'-end of the sense strand and the 5'-end of the antisense strand. In certain aspects, 1, 2, 3, 4, 5, 6, 7, or 8 hydroxymethyl substituted nucleomonomer(s) are covalently linked to the 3'-end of the sense strand and the 5'-end of the antisense strand.

In certain aspects, the one or more a hydroxymethyl substituted nucleomonomer(s) are covalently linked to the 5'-end of the sense strand and the 3'-end of the antisense strand. In certain aspects, 1, 2, 3, 4, 5, 6, 7, or 8 hydroxymethyl substituted nucleomonomer(s) are covalently linked to the 5'-end of the sense strand and the 3'-end of the antisense strand.

In certain aspects, blunt-ended dsRNA of this disclosure comprise a sense and antisense strand, wherein the 3'-end of the sense strand and the 3'-end of the antisense strand comprise one or more hydroxymethyl substituted nucleomonomers, and wherein the sense strand comprises an hydroxymethyl substituted nucleomonomer at positions 1, 2, and/or 3 counting from the 5'-end of the sense strand.

In certain aspects, blunt-ended dsRNA of this disclosure comprise a sense and antisense strand, wherein the 3'-end of the sense strand and the 3'-end of the antisense strand comprise one or more acyclic nucleomonomers, and wherein the antisense strand comprises an hydroxymethyl substituted nucleomonomer at positions 5, 6, 7, and/or 8 counting from the 5'-end of the antisense strand.

In certain aspects, blunt-ended dsRNA of this disclosure comprise a sense and antisense strand, wherein the 3'-end of the sense strand and the 3'-end of the antisense strand comprise one or more acyclic nucleomonomers, and wherein the sense strand comprises an hydroxymethyl substituted nucleomonomer at positions 1, 2, and/or 3 counting from the 5'-end of the sense strand, and wherein the antisense strand comprises an hydroxymethyl substituted nucleomonomer at positions 5, 6, 7, and/or 8 counting from the 5'-end of the antisense strand.

In certain aspects, blunt-ended dsRNA of this disclosure comprise a sense and antisense strand, wherein one or more acyclic nucleomonomers are covalently linked to the 3'-end of the sense strand and the 3'-end of the antisense strand, and wherein the sense strand comprises an hydroxymethyl substituted nucleomonomer at positions 1, 2, and/or 3 counting from the 5'-end of the sense strand.

In certain aspects, blunt-ended dsRNA of this disclosure comprise a sense and antisense strand, wherein one or more acyclic nucleomonomers are covalently linked to the 3'-end of the sense strand and the 3'-end of the antisense strand, and wherein the antisense strand comprises an hydroxymethyl substituted nucleomonomer at positions 5, 6, 7, and/or 8 counting from the 5'-end of the antisense strand.

In certain aspects, blunt-ended dsRNA of this disclosure comprise a sense and antisense strand, wherein one or more acyclic nucleomonomers are covalently linked to the 3'-end of the sense strand and the 3'-end of the antisense strand, and wherein the sense strand comprises an hydroxymethyl substituted nucleomonomer at positions 1, 2, and/or 3 counting from the 5'-end of the sense strand, and wherein the antisense strand comprises an hydroxymethyl substituted nucleomonomer at positions 5, 6, 7, and/or 8 counting from the 5'-end of the antisense strand.

In certain aspects, blunt-ended dsRNA of this disclosure comprise a sense and antisense strand, wherein one or more acyclic nucleomonomers are covalently linked to the 3'-end of the sense strand and the 3'-end of the antisense strand, and wherein one or more hydroxymethyl substituted nucleomonomers are covalently linked to the 5'-end of the sense strand, and wherein the sense strand comprises an hydroxymethyl substituted nucleomonomer at positions 1, 2, and/or 3 counting from the 5'-end of the sense strand, and wherein the antisense strand comprises an hydroxymethyl substituted nucleomonomer at positions 5, 6, 7, and/or 8 counting from the 5'-end of the antisense strand.

In certain aspects, blunt-ended dsRNA of this disclosure comprise a sense and antisense strand, wherein at least two acyclic nucleomonomers are covalently linked to the 3'-end of the sense strand and the 3'-end of the antisense strand, and wherein the sense strand comprises an hydroxymethyl substituted nucleomonomer at positions 1, 2, and/or 3 counting from the 5'-end of the sense strand, and wherein the antisense strand comprises an hydroxymethyl substituted nucleomonomer at positions 5, 6, 7, and/or 8 counting from the 5'-end of the antisense strand.

In certain aspects, blunt-ended dsRNA of this disclosure comprise a sense and antisense strand, wherein at least two acyclic nucleomonomers are covalently linked to the 3'-end of the sense strand and the 3'-end of the antisense strand, and wherein one or more hydroxymethyl substituted nucleomonomers are covalently linked to the 5'-end of the sense strand, and wherein the antisense strand comprises an hydroxymethyl substituted nucleomonomer at positions 5, 6, 7, and/or 8 counting from the 5'-end of the antisense strand.

In certain aspects, blunt-ended dsRNA of this disclosure comprise a sense and antisense strand, wherein at least two acyclic nucleomonomers are covalently linked to the 3'-end of the sense strand and the 3'-end of the antisense strand, and wherein 1, 2, and/or 3 hydroxymethyl substituted nucleomonomers are covalently linked to the 5'-end of the sense strand, and wherein the antisense strand comprises an hydroxymethyl substituted nucleomonomer at positions 5, 6, 7, and/or 8 counting from the 5'-end of the antisense strand.

In certain aspects, blunt-ended dsRNA of this disclosure comprise a sense and antisense strand, wherein at least one acyclic nucleomonomers is covalently linked to the 3'-end of the sense strand and the 3'-end of the antisense strand, and wherein one or more hydroxymethyl substituted nucleomonomers are covalently linked to the 5'-end of the sense strand, and wherein the sense strand comprises an hydroxymethyl substituted nucleomonomer at positions 1, 2, and/or 3 counting from the 5'-end of the sense strand, and wherein the antisense strand comprises an hydroxymethyl substituted nucleomonomer at positions 5, 6, 7, and/or 8 counting from the 5'-end of the antisense strand.

In certain aspects, blunt-ended dsRNA of this disclosure comprise a sense and antisense strand, wherein two acyclic nucleomonomers are covalently linked to the 3'-end of the sense strand and the 3'-end of the antisense strand, and wherein 1, 2, 3, and/or 4 hydroxymethyl substituted nucleomonomers are covalently linked to the 5'-end of the sense strand, and wherein the antisense strand comprises an hydroxymethyl substituted nucleomonomer at positions 5, 6, 7, and/or 8 counting from the 5'-end of the antisense strand.

In certain aspects, blunt-ended dsRNAs of this disclosure comprise a sense and antisense strand, wherein two or more acyclic nucleomonomers are covalently linked to the 3'-end of the sense strand and the 3'-end of the antisense strand, and wherein at least one hydroxymethyl substituted nucleomonomers is covalently linked to the 5'-end of the sense strand, and wherein the antisense strand comprises an hydroxymethyl substituted nucleomonomer at positions 5, 6, 7, and/or 8 counting from the 5'-end of the antisense strand.

In certain aspect, blunt-ended dsRNA of this disclosure comprise a sense and antisense strand, wherein an acyclic nucleomonomer is covalently linked to the 3'-end of the sense strand of the dsRNA and an acyclic nucleomonomer is covalently linked to the 3'-end of the antisense strand of the dsRNA, and wherein an hydroxymethyl substituted nucleomonomer is covalently linked to the 5'-end of the sense strand of the dsRNA, and wherein the antisense strand comprises an hydroxymethyl substituted nucleomonomer at positions 5, 6, 7, and/or 8 counting from the 5'-end of the antisense strand.

In certain aspect, blunt-ended dsRNA of this disclosure comprise a sense and antisense strand, wherein an acyclic nucleomonomer is covalently linked to the 3'-end of the sense strand of the dsRNA and an acyclic nucleomonomer is covalently linked to the 3'-end of the antisense strand of the dsRNA, and wherein an hydroxymethyl substituted nucleomonomer is covalently linked to the 5'-end of the sense strand of the dsRNA, and wherein the antisense strand comprises an hydroxymethyl substituted nucleomonomer at positions in the antisense strand the reduce the microRNA activity of the dsRNA compared to the same dsRNA without acyclic nucleomonomers in the antisense strand (i.e., an antisense strand of the dsRNA having no hydroxymethyl substituted nucleomonomer found between nucleotides).

In certain aspects, blunt-ended dsRNA of this disclosure comprise a sense and antisense strand, wherein the sense strand is a discontinuous strand (discontinuous passenger strand) comprising a first discontinuous passenger strand and a second discontinuous passenger strand, wherein an acyclic nucleomonomer is covalently linked to the 3'-end of the second discontinuous passenger strand of the dsRNA and an acyclic nucleomonomer is covalently linked to the 3'-end of the antisense strand of the dsRNA, and wherein an hydroxymethyl substituted nucleomonomer is covalently linked to the 5'-end of the first discontinuous passenger strand of the dsRNA, and wherein the antisense strand comprises an hydroxymethyl substituted nucleomonomer at positions 5, 6, 7, 8, 9, 10, 11, 12, 13, 14, 15, and/or 16 counting from the 5'-end of the antisense strand.

In certain aspects, blunt-ended dsRNA of this disclosure comprise a sense and antisense strand, wherein the sense strand is a discontinuous strand (discontinuous passenger strand) comprising a first discontinuous passenger strand and a second discontinuous passenger strand, wherein an acyclic nucleomonomer is covalently linked to the 3'-end of the first discontinuous passenger strand of the dsRNA and an acyclic nucleomonomer is covalently linked to the 3'-end of the antisense strand of the dsRNA, and wherein an hydroxymethyl substituted nucleomonomer is covalently linked to the 5'-end of the second discontinuous passenger strand of the dsRNA, and wherein the antisense strand comprises an hydroxymethyl substituted nucleomonomer at positions 5, 6, 7, 8, 9, 10, 11, 12, 13, 14, 15, and/or 16 counting from the 5'-end of the antisense strand.

In certain aspects, blunt-ended dsRNA of this disclosure comprise a sense and antisense strand, wherein the sense strand is a discontinuous strand (discontinuous passenger strand) comprising a first discontinuous passenger strand and a second discontinuous passenger strand, wherein an acyclic nucleomonomer is covalently linked to the 3'-end of the first discontinuous passenger strand of the dsRNA and an acyclic nucleomonomer is covalently linked to the 3'-end of the antisense strand of the dsRNA, and wherein an hydroxymethyl substituted nucleomonomer is covalently linked to the 5'-end of the second discontinuous passenger strand of the dsRNA.

In certain aspects, blunt-ended dsRNA of this disclosure comprise a discontinuous sense strand and antisense strand, wherein the discontinuous sense strand (discontinuous passenger strand) comprises a first strand and a second strand, wherein an acyclic nucleomonomer is covalently linked to the 3'-end of the second strand of the dsRNA and an acyclic nucleomonomer is covalently linked to the 3'-end of the antisense strand of the dsRNA, and wherein an hydroxymethyl substituted nucleomonomer is covalently linked to the 5'-end of the first strand of the dsRNA.

In certain aspects, blunt-ended dsRNA of this disclosure comprise a discontinuous sense strand and antisense strand, wherein the discontinuous sense strand (discontinuous passenger strand) comprises a first strand and a second strand, wherein an acyclic nucleomonomer is covalently linked to the 3'-end of the first strand of the dsRNA and an acyclic nucleomonomer is covalently linked to the 3'-end of the antisense strand of the dsRNA, and wherein an hydroxymethyl substituted nucleomonomer is covalently linked to the 5'-end of the second strand of the dsRNA.

In certain aspects, blunt-ended dsRNA of this disclosure comprise a discontinuous sense strand and antisense strand, wherein the discontinuous sense strand (discontinuous passenger strand) comprises a first strand and a second strand, wherein an acyclic nucleomonomer is covalently linked to the 3'-end of the first strand of the dsRNA and an acyclic nucleomonomer is covalently linked to the 3'-end of the antisense strand of the dsRNA, and wherein an hydroxymethyl substituted nucleomonomer is covalently linked to the 5'-end of the first strand of the dsRNA.

In certain aspects, blunt-ended dsRNA of this disclosure comprise a discontinuous sense strand and antisense strand, wherein the discontinuous sense strand (discontinuous passenger strand) comprises a first strand and a second strand, wherein an acyclic nucleomonomer is covalently linked to the 3'-end of the second strand of the dsRNA and an acyclic nucleomonomer is covalently linked to the 3'-end of the antisense strand of the dsRNA, and wherein an hydroxymethyl substituted nucleomonomer is covalently linked to the 5'-end of the second strand of the dsRNA.

In certain aspects, RNA complexes of this disclosure comprise a sense strand and antisense strand, wherein the sense strand comprises from about 25 to about 30 nucleomonomers and the antisense strand comprises from about 25 to about 30 nucleomonomers, wherein the sense strand comprises an hydroxymethyl substituted nucleomonomer at positions 16, 17, 18, 19, 20, 21, 22, 23, 24, 25 and/or 26 counting from the 5'-end of the sense strand.

In certain aspects, RNA complexes of this disclosure comprise a sense strand and antisense strand, wherein the sense strand comprises from about 25 to about 30 nucleomonomers and the antisense strand comprises from about 25 to about 30 nucleomonomers, wherein the antisense strand comprises an hydroxymethyl substituted nucleomonomer at positions 6, 7, 8, 9, 10, 11, and/or 12 counting from the 5'-end of the sense strand.

In certain aspects, RNA complexes of this disclosure comprise a sense strand and antisense strand, wherein the sense strand comprises about 25 nucleomonomers and the antisense strand comprises from about 27 nucleomonomers, wherein the sense strand comprises a hydroxymethyl substituted nucleomonomer at positions 21 and/or 22 counting from the 5'-end of the sense strand.

In certain aspects, RNA complexes of this disclosure comprise a sense strand and antisense strand, wherein the sense strand comprises about 25 nucleomonomers and the antisense strand comprises about 27 nucleomonomers, wherein the antisense strand comprises a hydroxymethyl substituted nucleomonomer at positions 6 and/or 7 counting from the 5'-end of the sense strand.

In any of the aspects disclosed herein, the RNA complex comprises a 2'-O-methyl nucleomonomer. In a related aspect, the RNA complex comprises from zero to twelve 2'-O-methyl nucleomonomer(s) (or 0, 1, 2, 3, 4, 5, 6, 7, 8, 9, 10, 11 or 12 2'-O-methyl nucleomonomer(s)). In a related aspect, the passenger strand of the RNA complex comprises from zero to twelve 2'-O-methyl nucleomonomer(s) (or 0, 1, 2, 3, 4, 5, 6, 7, 8, 9, 10, 11 or 12 2'-O-methyl nucleomonomer(s)). In a related aspect, the guide strand of the RNA complex comprises from zero to six 2'-O-methyl nucleomonomer(s) (or 0, 1, 2, 3, 4, 5 or 6 2'-β-methyl nucleomonomer(s)). In certain aspects, the hydroxymethyl substituted monomer is a 2'-O-methyl nucleomonomer.

In certain aspects, RNA complexes of this disclosure comprise one or more hydroxymethyl substituted nucleomonomers, wherein the RNA complex has less affinity for a Toll-like receptor 3 (TLR3) compared to the same RNA complex without one or more hydroxymethyl substituted nucleomonomers.

In certain aspects, RNA complexes of this disclosure comprise one or more hydroxymethyl substituted nucleomonomers, wherein the affinity of the dsRNA for a Toll-like receptor 3 (TLR3) is reduced compared to the same RNA complex without one or more hydroxymethyl substituted nucleomonomers.

In certain aspects, RNA complexes of this disclosure comprise one or more hydroxymethyl substituted nucleomonomers, wherein the RNA complex has a decreased ability to activate a Toll-like receptor 3 (TLR3) compared to the same RNA complex without one or more hydroxymethyl substituted nucleomonomers.

In certain aspects, this disclosure provides methods for reducing the activation of a Toll-like receptor 3 (TLR3) by dsRNA, the methods comprising identifying a dsRNA that activates TLR3, modifying the dsRNA with one or more hydroxymethyl substituted nucleomonomers and performing an a TLR3 activation and/or gene expression assay to determine whether the modification of the dsRNA with one or more hydroxymethyl substituted nucleomonomers decreases activation of TLR3 compared to the same dsRNA without one or more acyclic nucleomonomers.

In certain aspects, this disclosure provides methods for reducing the activation of a MDA-5 gene by dsRNA, the methods comprising identifying a dsRNA that activates MDA-5, modifying the dsRNA with one or more hydroxymethyl substituted nucleomonomers and performing an a MDA-5 activation and/or gene expression assay to determine whether the modification of the dsRNA with one or more hydroxymethyl substituted nucleomonomers decreases activation of MDA-5 compared to the same dsRNA without one or more acyclic nucleomonomers.

In certain aspects, this disclosure provides methods for reducing the activation of a RIG-I gene by dsRNA, the methods comprising identifying a dsRNA that activates RIG-I, modifying the dsRNA with one or more hydroxymethyl substituted nucleomonomers and performing an a RIG-I activation and/or gene expression assay to determine whether the modification of the dsRNA with one or more hydroxymethyl substituted nucleomonomers decreases activation of RIG-I compared to the same dsRNA without one or more acyclic nucleomonomers.

In certain aspects, this disclosure provides methods for inhibiting or reducing one or more toll-like receptor (TLR) pathways in a cell, including for example TLR1, TLR2, TLR3, TLR4, TLR5, TLR6, TLR7, TLR8, TLR9, TLR10 and TLR11 by contacting the cell with an acyclic nucleomonomer whereby one or more TLR pathways are inhibited or reduced. In certain aspects, the hydroxymethyl substituted nucleomonomers are linked together (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more) or are incorporated into a nucleic acid (e.g., DNA, RNA, DNA/RNA hybrid). In certain aspects, the hydroxymethyl substituted nucleomonomers are a homogenous population (i.e., comprise the purine or pyrimidine) or are a heterogeneous population (i.e., both purines and pyrimidines). In certain aspects, the hydroxymethyl substituted nucleomonomer is a TLR antagonist. In certain aspects, the acyclic nucleomonomer binds to a TLR. In certain aspects, the hydroxymethyl substituted nucleomonomer that inhibits or reduces one or more TLR pathways in a cell, may be monomer C, D, E, F, G, H, I or J. In certain aspects, the hydroxymethyl substituted nucleomonomer that inhibits or reduces one or more TLR pathways in a cell, may be monomer D, F, G, H, I or J. In certain aspects, the hydroxymethyl substituted nucleomonomer that inhibits or reduces one or more TLR pathways in a cell, may be monomer D.

Preferred RNA complexes of the disclosure are similar in overall structure to the products of DICER processing of longer double stranded RNA complexes. In another embodiment, the RNA complexes of the disclosure are Dicer substrates as mentioned above.

Other preferred RNA complexes of the disclosure are complexes wherein the core double-stranded region comprises 18-22 base pairs, and wherein the antisense strand and the passenger strand each comprise a 3'-overhang of 1-3 nucleotides.

The antisense strand of the RNA complex of the disclosure can have varying lengths, without interfering with the function of the complex. Thus, in preferred embodiments, the antisense strand is an 8-mer, 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, a 24-mer, a 25-mer, a 26-mer, a 27-mer, a 28-mer, 29-mer, 30-mer, 31-mer, 32-mer, 33-mer, 34-mer, 35-mer, 36-mer, 37-mer, 38-mer, 39-mer, 40-mer, 41-mer, 42-mer, 43-mer, 44-mer, 45-mer, 46-mer, 47-mer, 48-mer, 49-mer, 50-mer, 51-mer, 52-mer, 53-mer, 54-mer, 55-mer, 56-mer, 57-mer, 58-mer, 59-mer, 60-mer, 61-mer or a 62-mer, respectively. It is to be understood that e.g. a 19-mer is an antisense strand of 19 monomers that may be nucleotides or hydroxymethyl substituted nucleomonomers, or a combination thereof.

In another preferred embodiment, the antisense strand of the RNA complex is selected from the following group of antisense strands: A 15-mer, 16-mer, 17-mer, 18-mer, 19-mer, 20-mer, 21-mer, 22-mer and a 23-mer.

In one embodiment the passenger strand of an siRNA complex of the disclosure is discontinuous. In one embodiment of an siRNA complex of the disclosure, the passenger strand comprises several separate RNA molecules. The number of RNA molecules may be 1, 2, 3, 4, 5 or 6.

In one embodiment, the length of individual RNA molecules of the passenger strand of an siRNA complex of the disclosure is above 4 monomers. In other embodiments, the length of individual RNA molecules of the passenger strand is above 5 monomers, 6 monomers, 7 monomers, 8 monomers, 9 monomers, 10 monomers, 11 monomers and 12 monomers, respectively.

In other embodiments, the length of individual RNA molecules of the passenger strand of an siRNA complex of the disclosure is below 5 monomers, 6 monomers, 7 monomers, 8 monomers, 9 monomers, 10 monomers, 11 monomers and 12 monomers, respectively.

In one embodiment of the disclosure, a discontinuous passenger strand of an siRNA complex of the disclosure comprises a first and a second RNA-molecule, which together forms the discontinuous passenger strand, wherein the first RNA molecule is hybridized to the downstream part of the antisense strand and the second RNA molecule is hybridized to the upstream part of the antisense strand.

In one embodiment, the antisense strand of an siRNA complex of the disclosure is discontinuous. Preferred discontinuities of the antisense strands are the same as the preferred discontinuities of the passenger strand.

A discontinuity of one of the strands of an siRNA complex of the disclosure can be a nick. A nick is to be understood as a discontinuity in one strand of a double-stranded nucleic acid caused by a missing phosphodiester bond, however, without the double-stranded nucleic acid missing a nucleotide. Thus, the bases opposite to the nick will still be hybridized to bases on the nicked strand.

Another discontinuity of one of the strands of an siRNA complex of the disclosure is an alternative nick, which is understood as a discontinuity in one strand of a double-stranded nucleic acid caused by one missing bond, or more than one missing bond in the sugar-phosphate backbone, other than a phosphodiester bond, however, without the double-stranded nucleic acid missing a nucleobase. Thus, the bases opposite to the nick may still be hybridized to bases on the nicked strand.

A gap as used as a nomination when an RNA strand of an RNA complex of the disclosure can be described to have a discontinuity where at least one nucleotide or nucleoside or a nucleobase is missing in the double-stranded nucleic acid.

Preferably, the 5'-ends of the RNA complex is phosphorylated or is available for phosphorylation. Available for phosphorylation means that the 5'-hydroxy group has not been blocked e.g. by direct conjugation or by other conjugation to other groups in the vicinity of the 5'-hydroxy group, which will prevent the 5'-hydroxy group from being phosphorylated.

Hence, in a preferred embodiment of the disclosure, the RNA molecule(s) of the RNA complex comprise(s) a 5'-end phosphate and a 3'-hydroxy group.

In another embodiment, the second RNA molecule of an siRNA complex of the disclosure comprises a 5'-end phosphate and a 3'-hydroxy group.

In yet another embodiment, the antisense strand comprises a 5'-end phosphate and a 3'-hydroxy group.

In some embodiments of the disclosure, it is preferred that the RNA complex comprises nucleotide analogues other than the hydroxymethyl substituted nucleotides. Such nucleotide analogues other than the hydroxymethyl substituted nucleotides are termed below as "alternatively modified nucleotides".

The use of alternatively modified nucleotides may be favoured for several reasons. They may e.g. be used to increase the melting temperature of the core double stranded region of an siRNA complex of the disclosure.

The use of alternatively modified nucleotides may be favoured to increase the melting temperature of the double stranded structure formed between the antisense strand and the target nucleic acid.

Accordingly, in one embodiment, the antisense strand comprises alternatively modified nucleotides. In another embodiment, the passenger strand of an siRNA complex of the disclosure comprises alternatively modified nucleotides. In yet another embodiment, a first and second RNA molecule of the passenger strand of an siRNA complex of the disclosure each contains alternatively modified nucleotides. In one embodiment of the disclosure, the number of alternatively modified nucleotides in the RNA complex is 10. In other embodiments of the disclosure, the number of nucleotide analogues in the RNA complex is 9, 8, 7, 6, 5, 4, 3, 2 or 1, respectively. In one embodiment of the disclosure, the number of alternatively modified nucleotides in the antisense strand is 10. In other embodiments of the disclosure, the number of nucleotide analogues in the antisense strand is 9, 8, 7, 6, 5, 4, 3, 2 or 1, respectively. In another embodiment, all nucleotides of the antisense strand are alternatively modified nucleotides or a combination of alternatively modified nucleotides and hydroxymethyl-substituted nucleotides.

Likewise, in another embodiment of the disclosure, the number of nucleotide analogues in the passenger strand of an siRNA complex of the disclosure is 10. In other embodiments of the disclosure, the number of nucleotide analogues in the passenger strand is 9, 8, 7, 6, 5, 4, 3, 2 or 1, respectively.

In another embodiment, all nucleotides of the passenger strand of an siRNA complex of the disclosure are nucleotide analogues or a combination of alternatively modified nucleotides and hydroxymethyl-substituted nucleotides.

In one embodiment, both the antisense strand and the sense strand of an siRNA complex of the disclosure contain alternatively modified nucleotides.

In one embodiment, the alternatively modified nucleotides of the RNA complex are identical, i.e. they are for example all LNA or all 2'-O-Me-RNA. In another embodiment, various different alternatively modified nucleotides are used in the same RNA complex.

In one embodiment, the RNA complex comprises phosphorothioate linkages.

In another embodiment, the RNA complex comprises a mixture of natural phosphodiester and phosphorothioate linkages.

Preferred nucleotide analogues of the disclosure is nucleotide analogues selected from the group of 2'-O-alkyl-RNA monomers, 2'-amino-DNA monomers, 2'-fluoro-DNA monomers, LNA monomers, HNA monomers, ANA monomers, FANA monomer, DNA monomers, PNA monomers and INA monomers, but other monomers can also be used [Nawrot and Sipa, *Curr. Topics Med. Chem.* 2006, 6, 913-925].

In one embodiment the hydroxymethyl substituent of the hydroxymethyl substituted monomers of the disclosure is functionalized by a conjugating group. A conjugating group is a group known to a person skilled in the art that changes, expands or improves the properties of an RNA complex of the disclosure. Such groups may be useful for modulating cellular distribution, organ distribution, tissue distribution, duplex melting temperatures, target affinity, biostability, signalling of hybridization etc.

In one embodiment the hydroxymethyl substituent of the hydroxymethyl substituted monomers of the disclosure is functionalized by an ether linkage between a conjugated group and the methylene group of the hydroxymethyl substituent. See FIG. 2 (Monomer F).

In one embodiment the hydroxymethyl substituent of the hydroxymethyl substituted monomers of the disclosure is converted into a thioether functionality before incorporation into the RNA complex of the disclosure using methods known to a person skilled in the art. See FIG. 2 (Monomer G).

In another embodiment the hydroxymethyl substituent of the hydroxymethyl substituted monomers of the disclosure is converted into a mercaptomethyl functionality before incorporation into the RNA complex of the disclosure using methods known to a person skilled in the art. See FIG. 2 (Monomer G, R=H). This mercapto functionality is properly protected as e.g. its acetyl derivative during RNA synthesis using methods know to a person skilled in the art.

In one embodiment the hydroxymethyl substituent of the hydroxymethyl substituted monomers of the disclosure is converted into an amine functionality before incorporation into the RNA complex of the disclosure using methods known to a person skilled in the art. See FIG. 2 (Monomer I, R=H). This amine functionality is properly protected as e.g. its trifluoroacetyl or Fmoc derivative during RNA synthesis using methods know to a person skilled in the art.

Figure 2:
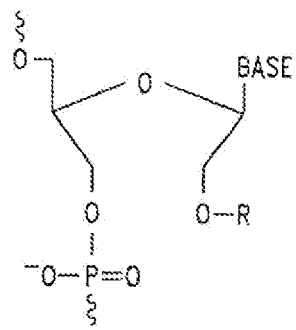
FIG. 2: Derivatized, functionalized and conjugated variants of the hydroxymethyl substituted monomers are shown. As examples are shown derivatized, functionalized and conjugated variants of the hydroxymethyl substituted 2',3'-seco-monomer D (see FIG. 1). Monomer F contains a group R linked via an ether linkage. Monomer G contains a group R linked via a thioether linkage. Monomer H contains a group R linked via an amide linkage. Monomer I contains a group R linked via an amino linkage. Monomer J contains a group R linked via a piperazino unit. By incorporation of one or several of such monomers into the RNA complexes of the disclosure, the properties of the RNA complexes can be modulated. For example can increased biostability, increased RNA targeting capability or specific delivery properties be introduced, and fluorescent groups can be attached for detection purposes.
Figure 2:
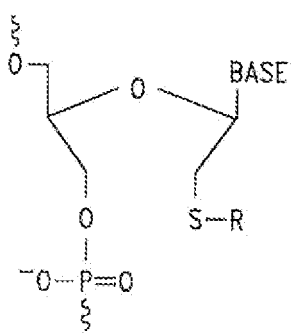
Figure 2:
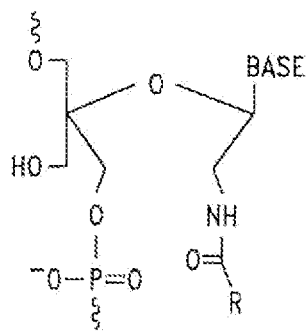
Figure 2:
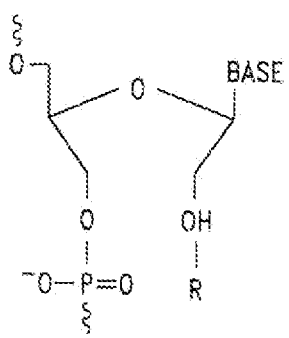
Figure 2:
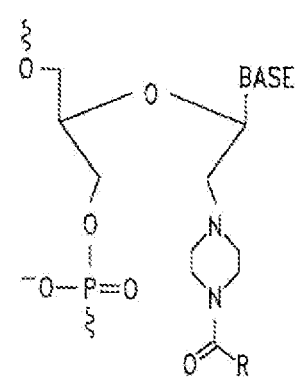
Figure 3:
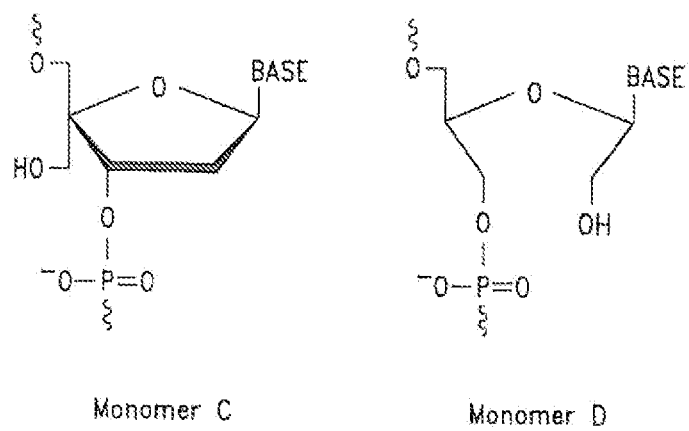
FIG. 3: Structures of two of the hydroxymethyl substituted monomers (Monomer C and Monomer D) that may be a monomer of an oligonucleotide or RNA complex.

In one embodiment the hydroxymethyl substituent of the hydroxymethyl substituted monomers of the disclosure is acting as a handle for attachment of amide-linked conjugating groups. This involves conversion of the hydroxyl unit of the hydroxymethyl substituent into an amine unit, for example as described above, and further derivatization of this amino group by e.g. a conjugating group by amide bond formation using methods known to a person skilled in the art. This may take place before RNA synthesis or after RNA synthesis using methods known to a person skilled in the art (FIG. 2, Monomer H).

In one embodiment the hydroxymethyl substituent of the hydroxymethyl substituted monomers of the disclosure is acting as a handle for attachment of amino-linked conjugating groups. This involves conversion of the hydroxyl unit of the hydroxymethyl substituent into an amine unit, for example as described above, and further derivatization of this amino group by e.g. a conjugating group by amine bond formation using methods known to a person skilled in the art. This may take place before RNA synthesis or after RNA synthesis using methods known to a person skilled in the art (FIG. 2, Monomer I).

In still one embodiment, the amine group used for conjugation is an amino group, a piperazino group or a diamino alkyl group. Such monomers are called amine-derivatized monomers. Each of these groups may be further derivatized or conjugated (FIG. 2, Monomer J).

In one embodiment, the RNA complex of the disclosure has reduced off target effects as compared to native RNA complexes.

In one preferred embodiment, the RNA complex has at least one hydroxymethyl-substituted monomer of the disclosure in the antisense strand.

In another preferred embodiment, the RNA complex has at least one hydroxymethyl-substituted monomer of the disclosure incorporated in or around the so-called seed region of the antisense strand, i.e. in at least one of positions no. 1-12 from the 5'-end of the antisense strand. In yet another preferred embodiment, the RNA complex has at least one hydroxymethyl-substituted monomer of the disclosure incorporated in at least one of positions no. 2-10 from the 5'-end of the antisense strand. In yet another preferred embodiment, the RNA complex has one hydroxymethyl-substituted monomer of the disclosure incorporated in one of positions no. 3-8 from the 5'-end of the antisense strand. In yet another preferred embodiment, the RNA complex has one hydroxymethyl-substituted monomer of the disclosure incorporated in one of positions no. 7 or 8 from the 5'-end of the antisense strand. In yet another preferred embodiment, the RNA complex has one hydroxymethyl-substituted monomer of the disclosure incorporated in position no. 7 from the 5'-end of the antisense strand. In yet another preferred embodiment, the RNA complex has one hydroxymethyl-substituted monomer of the disclosure incorporated in positions no. 9-16 from the 5'-end of the antisense strand. In yet another preferred embodiment, the RNA complex has one hydroxymethyl-substituted monomer of the disclosure incorporated in positions no. 9-11 from the 5'-end of the antisense strand. In yet another preferred embodiment, the RNA complex has one hydroxymethyl-substituted monomer of the disclosure incorporated in positions no. 9-10 from the 5'-end of the antisense strand. In another embodiment, the RNA complex of the disclosure produces a reduced immune response as compared to native RNA complexes.

In still another embodiment, the RNA complexes of the disclosure have a prolonged effect as compared to native RNA complexes.

In yet another embodiment, the RNA complexes of the disclosure have an increased effect as compared to native RNA complexes. Accordingly, in a preferred embodiment, the RNA complex mediate RNAi more effectively than the native RNA complex, e.g. by more efficient degradation of target mRNA or by more efficient translational inhibition of target mRNA.

In still another embodiment, the RNA complexes of the disclosure are delivered efficiently to specific organs or tissues of a human or an animal.

In yet still another embodiment, the RNA complexes of the disclosure are able to penetrate the cell membrane efficiently. In yet still another embodiment, the RNA complexes of the disclosure are able to penetrate the cell membrane more efficiently that natural RNA complexes. In one embodiment, the RNA complexes of the disclosure are able to bind to plasma proteins which increase the retention of the RNA complexes in the human body.

In one embodiment, the RNA complex may be a blunt ended double-stranded RNA (dsRNA) that downregulates the expression of a target nucleic acid, the dsRNA comprising a sense strand and an antisense strand, a double-stranded region of from 19 to 24 base pairs, and one or more hydroxymethyl substituted nucleomonomers linked to at least one blunt end of the dsRNA. In a related embodiment, the sense strand and the antisense strand independently have from 19 nucleomonomers. In another related embodiment, the sense strand comprises one or more hydroxymethyl substituted nucleomonomers. In yet another embodiment, one or more hydroxymethyl substituted nucleomonomers are in position 1, 2, 3, 4, and/or 5 from the 5'-end of the sense strand. In a related embodiment, the antisense strand comprises one or more hydroxymethyl substituted nucleomonomers. In a related embodiment, one or more hydroxymethyl substituted nucleomonomers are in position 4, 5, 6, 7, 8, 9 and/or 10 from the 5'-end of the antisense strand.

In another embodiment, the RNA complex may be a blunt ended double-stranded RNA (dsRNA) that downregulates the expression of a target nucleic acid, the dsRNA comprising a sense strand and an antisense strand, a double-stranded region of from 25 to 30 base pairs, and one 3'-end overhang comprising hydroxymethyl substituted nucleomonomers. In a related embodiment, the sense strand and the antisense strand independently have from 25 to 35 nucleomonomers. In yet another embodiment, the sense strand has 25 nucleomonomers and the antisense strand has 27 nucleomonomers. In yet another embodiment, the sense strand comprises one or more hydroxymethyl substituted nucleomonomers. In another embodiment, one or more hydroxymethyl substituted nucleomonomers reduce or prevent cleavage of the dsRNA by the Dicer enzyme. In a related embodiment, the one or more hydroxymethyl substituted nucleomonomers flank the Dicer cleavage site of the dsRNA. In another embodiment, the one or more hydroxymethyl substituted nucleomonomers are in position 19, 20, 21, 22, 23, 24, 25, 26, 27, 28, 29, 30, 31, and/or 32 from the 5'-end of the sense strand. In a related embodiment, the antisense strand comprises one or more hydroxymethyl substituted nucleomonomers. In a related embodiment, the one or more hydroxymethyl substituted nucleomonomers are in position 5, 6, 7, 8, 9, 10, 11, 12, 13, 14, 15, 16, and/or 17 from the 5'-end of the antisense strand.

In a related embodiment, the hydroxymethyl substituted nucleomonomer is a 2'-3'-seco-nucleomonomer.

As used herein the term "bifunctional RNA complex" or "bifunctional dsRNA" means an RNA complex having a sense strand and antisense strand, wherein the sense strand and the antisense strand are each complementary to different regions of the same target RNA (i.e., a first region and a second region), or are each complementary to a region of at least two different target RNAs.

In one embodiment, the RNA complex may be a bifunctional RNA complex having two blunt-ends and an hydroxymethyl substituted nucleomonomer at position(s) 5, 6, 7, and/or 8 from the 5'-end of each of the guide strand and passenger strand.

In one embodiment, the bifunctional RNA complex comprise two blunt-ends, a sense strand and a antisense strand, wherein the sense strand comprises an hydroxymethyl substituted nucleomonomer at position(s) 5, 6, 7, and/or 8 from the 5'-end of the sense strand, and the antisense strand comprises an hydroxymethyl substituted nucleomonomer at position(s) 5, 6, 7, and/or 8 from the 5'-end of antisense strand, and wherein the sense strand is complementary to a first region of a target RNA and the antisense region is complementary to a second region of the target RNA, wherein the first region and the second region are non-overlapping regions of the target RNA. In a related embodiment, the first and second regions of the target RNA partially overlap.

In one embodiment, the bifunctional RNA complex comprise two blunt-ends, a sense strand and a antisense strand, wherein the sense strand comprises an hydroxymethyl substituted nucleomonomer at position(s) 5, 6, 7, and/or 8 from the 5'-end of the sense strand, and the antisense strand comprises an hydroxymethyl substituted nucleomonomer at position(s) 5, 6, 7, and/or 8 from the 5'-end of antisense strand, and wherein the sense strand is complementary to a first region of a first target RNA and the antisense region is complementary to a second region of a second target RNA, wherein the first target RNA and the second target RNA are different target RNAs, or have less than 95% homology, or 90% homology, or 85% homology, or 80% homology, or 75% homology, or 70% homology, or 65% homology, or 60% homology, or 55% homology or 50% homology. In a related embodiment, the first and second target RNAs are in the same cellular pathway.

Methods of Preparing an RNA Complex

Another aspect of the disclosure is a method of preparing a two stranded RNA complex of the disclosure comprising incubating the antisense strand with the passenger strand under conditions wherein a RNA complex comprising a core double stranded region is formed, said RNA complex being capable of mediating RNA interference of a corresponding cellular RNA.

In another aspect of the disclosure a method of preparing an RNA complex comprising one or more hydroxymethyl substituted nucleomonomers that regulates the expression of a target mRNA, comprising the steps of synthesizing at least two nucleic acid strands each having from 15 to 40 nucleomonomers; combining the synthesized nucleic acid strands under conditions suitable for form a blunt-ended RNA complex having a double-stranded region; and wherein the 3'-end of each strand comprises one or more hydroxymethyl substituted nucleomonomers.

In another aspect of the disclosure a method of preparing an RNA complex comprising one or more hydroxymethyl substituted nucleomonomers that regulates the expression of a target mRNA, comprising the steps of synthesizing at least two nucleic acid strands each having from 18 to 30 nucleomonomers; combining the synthesized nucleic acid strands under conditions suitable for a blunt-ended RNA complex having a double-stranded region; and wherein the 3'-end of each strand comprises one or more hydroxymethyl substituted nucleomonomers.

In alternative embodiments of this aspect, the RNA complex is substituted by an RNA duplex of the disclosure (tenth aspect).

Still another aspect of the disclosure is a method of mediating nucleic acid modification of a target nucleic acid in a cell or an organism comprising the steps of contacting a cell or organism with the RNA complex of the disclosure under conditions wherein modification of a target nucleic acid can occur, and thereby mediating modification of a target nucleic acid.

In preferred embodiments, the method of mediating nucleic acid modification of a target nucleic acid is performed in vitro. In preferred embodiments, the method of mediating nucleic acid modification of a target nucleic acid is performed in vivo, i.e. in animals, in humans or in non-human animals. In preferred embodiments, the method of mediating nucleic acid modification of a target nucleic acid is performed in cell cultures. In yet another embodiment, the method is performed on an isolated cell.

In a preferred embodiment, the nucleic acid modification of the method is RNA interference, preferable degradation of target mRNA or translational inhibition of target mRNA or inhibition of regulatory non-coding RNA (e.g., microRNA).

In another embodiment, the nucleic acid modification is DNA methylation.

In alternative embodiments of this aspect, the RNA complex is substituted by either an oligonucleotide of the disclosure (ninth aspect) or an RNA duplex of the disclosure (tenth aspect).

A fourth aspect of this disclosure includes a method of examining gene function. Another aspect of the disclosure is a method of examining the function of a gene in a cell or organism, the method comprising the steps of introducing an RNA complex of the disclosure corresponding to the gene into a cell or an organism, thereby producing a test cell or test organism, maintaining the test cell or test organism under conditions under which modification of a target nucleic acid can occur, and observing the phenotype of the test cell or organism produced in step b and optionally comparing the observed phenotype with the phenotype of an appropriate control cell or control organism, thereby providing information about the function of the gene. The RNA complex of the disclosure can be introduced into cells e.g. using transfection, as outlined in the appended examples. The phenotype of the organism or cell may be observed e.g. using proteomics to assess protein levels or using microarrays to assess RNA levels. Also a more defined phenotype may be used, e.g. the expression of one particular gene. The information obtained about the function of a gene may be used to determine whether a gene product is a suitable target for therapeutic intervention in relation to a particular disease. Thus, if it is demonstrated that a certain gene product act in a certain biochemical pathway known to be affected in e.g. a specific subtype of cancer, the gene product might be a suitable target for therapeutic intervention for treatment of the aforementioned subtype of cancer.

In a preferred embodiment of the method of examining the function of a gene in a cell or organism, the nucleic acid modifications of the method are RNA interference, preferable degradation of target mRNA or translational inhibition of target RNA.

In another embodiment, the nucleic acid modification is DNA methylation.

In preferred embodiments of the method of examining the function of a gene in a cell or organism, the method is performed in cell cultures, in vitro or in vivo.

In yet another embodiment, the method is performed on an isolated cell.

In alternative embodiments of this aspect, the RNA complex is substituted by either an oligonucleotide of the disclosure (ninth aspect) or an RNA duplex of the disclosure (tenth aspect).

In a fifth aspect of this disclosure, a method of evaluating agent is provided. Another aspect of the disclosure is a method of assessing whether an agent acts on a gene product comprising the steps of introducing the RNA complex of the disclosure corresponding to said gene into a cell or organism, thereby producing a test cell or test organism maintaining the test cell or test organism under conditions under which modification of a target nucleic acid occurs, introducing the agent into the test cell or test organism, observing the phenotype of the test cell or organism, and optionally comparing the observed phenotype with the phenotype of an appropriate control cell or control organism, thereby providing information about whether the agent acts on the gene product.

In a preferred embodiment of the method of assessing whether an agent acts on a gene or gene product, the nucleic acid modifications of the method are RNA interference, preferable degradation of target RNA or translational inhibition of target RNA. In another embodiment, modification of nucleic acid modifications is DNA methylation.

In preferred embodiments of the method of assessing whether an agent acts on a gene product, the method is performed in cell cultures, in vitro or in vivo. In yet another embodiment, the method is performed on an isolated cell. In alternative embodiments of this aspect, the RNA complex is substituted by either an oligonucleotide of the disclosure (ninth aspect) or an RNA duplex of the disclosure (tenth aspect).

In a sixth aspect of the disclosure, a pharmaceutical composition is provided. Still another aspect of the disclosure is the RNA complex and a pharmaceutically acceptable diluent, carrier or adjuvant. It will be apparent to the skilled person that the RNA complexes of the disclosure can be designed to target specific genes and gene products. It is to be understood that the RNA complexes will target a DNA sequence or a RNA sequence, and not a protein. However, the level of a gene product such as a protein may be affected indirectly, if it's mRNA or a non-coding RNA is modified e.g. by RNA degradation or translational inhibition. Also the expression of the gene encoding the protein may be affected, e.g. because of DNA methylation.

In alternative embodiments of this aspect, the RNA complex is substituted by either an oligonucleotide of the disclosure (ninth aspect) or an RNA duplex of the disclosure (tenth aspect).

In a seventh aspect of this disclosure, a use of a medicament is provided. Thus, another aspect is the RNA complex of the disclosure for use as a medicament. Once a therapeutic target has been validated, the skilled person can design RNA complexes that affect the level and the activity of the target, because the specificity of the RNA complexes lies exclusively within the sequence of the antisense strand. For native RNA complexes with a continuous passenger strand, there remains a problem with off-target effects due to the passenger strand acting as a guide sequence.

In alternative embodiments of this aspect, the RNA complex is substituted by either an oligonucleotide of the disclosure (ninth aspect) or an RNA duplex of the disclosure (tenth aspect).

In an eighth aspect of this disclosure, monomers are provided. An aspect of the disclosure is monomers suitable for incorporation of the hydroxymethyl substituted monomers of the disclosure and methods for their preparation from readily available starting materials. Thymin-1-yl derivatives of hydroxymethyl substituted monomers of the disclosure have been incorporated into DNA strands, and procedures for preparation of their phosphoramidite building blocks for automated DNA/RNA synthesis have been reported [K. D. Nielsen et al., *Bioorg. Med. Chem.* 1995, 3, 1493; H. Thrane et al., *Tetrahedron* 1995, 51, 10389; P. Nielsen et al., *Bioorg. Med. Chem.* 1995, 3, 19].

Most often, the RNA complexes of the disclosure will be prepared by automated oligonucleotide synthesis as known to a person skilled in the art. The incorporation of the hydroxymethyl substituted monomers of the disclosure into the RNA complexes of the disclosure follows standard methods for a) RNA synthesis on an automated RNA synthesizer, b) RNA work-up, c) RNA purification and d) RNA isolation [F. Eckstein, Oligonucleotides and Analogues, IRL Press, Oxford University Press, 1991]. The hydroxymethyl substituted RNA oligonucleotides (=RNA strands) and RNA complexes can be synthesised using phosphoramidite derivatives using the standard techniques for RNA synthesis.

In a preferred embodiment, methods of preparation of the phosphoramidite derivatives of the hydroxymethyl substituted monomers of the disclosure begins from a ribonucleoside, for example a O5'-DMT protected derivative of a ribonucleoside that for the bases adenine, guanine, cytosine and 5-methylcytosine contains base protecting groups like for example, benzoyl, isobutyryl, acetyl, phenoxyacetyl, tert-butylphenoxyacetyl or other standard base protecting groups known to a person skilled in the art.

In a preferred embodiment, the disclosure comprises methods to prepare monomeric building blocks suitable for incorporation of the Monomers D and E having a 2',3'-cleaved carbon-carbon bond (ribonucleoside nomenclature).

In other preferred embodiments, the disclosure comprises methods to prepare monomeric building blocks suitable for incorporation of the Monomers like F-J having a 2',3'-cleaved carbon-carbon bond and in addition carrying a functionality or group at for example its 2'-carbon atom (ribonucleoside nomenclature) other than a hydroxy group.

In a preferred embodiment of the disclosure, the method of preparation of the phosphoramidite derivatives of Monomer D comprises among the key steps 2',3'-glycol cleavage, reduction of the resulting intermediate, selective O2'-protection and O3'-phosphitylation.

In a preferred embodiment the 2',3'-glycol cleavage is undertaken using oxidative cleavage with for example sodium periodate as reagent.

In another preferred embodiment the reduction of the intermediate after sodium periodate cleavage is reduced to the corresponding diol affected by for example sodium borohydride.

For incorporation of Monomer D into the RNA complexes of the disclosure it is necessary to protect the 2'-hydroxy group (ribonucleoside nomenclature). In a preferred embodiment of the disclosure this is done by benzoylation. It may be beneficial to use only slightly more than one equivalent of benzoylation reagent (benzoyl chloride or e.g. benzoyl anhydride) in order to optimize the selectivity of the protection, i.e. the amount of O2'-benzoylation relative to O3'-benzoylation. In one preferred embodiment the benzoylation is performed below room temperature. In another useful embodiment the benzoylation is performed below 0° C. or even below −50° C.

In another preferred embodiment the O2'-protection is done by acetylation or by performing acylation using an acylation reagent known to a person skilled in the art of organic synthesis.

In another preferred embodiment the O2'-protection is done by silylation using a silylation reagent and method known to a Person skilled in the art of organic synthesis. A preferred silylation protecting group is tert-butyldimethylsilyl or triisopropyloxymethyl.

The subsequent phosphitylation reaction is in a preferred embodiment performed using either the so-called "PCl" reagent [PCl(OCH$_2$CH$_2$CN)(N(iPr)$_2$)] or the so-called "bis-amidite" reagent [P(OCH$_2$CH$_2$CN)(N(iPr)$_2$)$_2$].

In a preferred embodiment of the methods of preparation of the phosphoramidite derivatives of Monomer D, the starting material is a ribonucleoside, for example a O5'-DMT protected derivative of a ribonucleoside that for the bases adenine, guanine, cytosine and 5-methylcytosine contains base protecting groups like for example, benzoyl, isobutyryl, acetyl, phenoxyacetyl, tert-butylphenoxyacetyl or other standard base protecting groups known to a Person skilled in the art.

In a preferred embodiment of the disclosure, the method of preparation of the phosphoramidite derivatives of Monomer E comprises among the key steps 2',3'-glycol cleavage, reduction of the resulting intermediate, selective O3'-protection and O2'-phosphitylation. The O3'-protection can for example be performed by silylation or acylation, or by a combination like first O2'-benzoylation, then O3'-silylation, and then O2'-debenzoylation. Other protecting groups may also be applied as would be clear for a Person skilled in the art.

In another preferred embodiments, the method to prepare monomeric building blocks suitable for incorporation of the Monomers like F-J, having a 2',3'-cleaved carbon-carbon bond and in addition carrying a functionality at its 2'-carbon atom (ribonucleoside nomenclature) other than a hydroxy group, comprises among the key steps starting from a ribonucleoside (for example a O5'-DMT protected ribonucleoside) 2',3'-glycol cleavage, reduction of the resulting intermediate, selective O3'-protection, conversion of the 2'-hydroxy group, O3'-deprotection and O3'-phosphitylation. The O3'-protection can for example be performed by silylation or acylation, or a combination of the both like first O2'-benzoylation, then O3'-silylation, and then O2'-debenzoylation. Other protecting groups may also be applied as would be clear for a person skilled in the art. The conversion of the 2'-hydroxy group into another group like amino, acylated amino, alkylated amino, dialkylated amino, carbamoylated amino, piperazino, acylated piperazino, alkylated piperazino, carbamoylated piperazino, mercapto, acylated mercapto, alkylated mercapto, disulfide, acylated hydroxy, alkylated hydroxy, carbamoylated hydroxy, etc., or by substituted and/or protected derivatives of these groups, can be performed using methods and procedures known to a person skilled in the art of organic synthesis. Such methods and procedures include substitution reactions on an activated derivative of the 2'-hydroxy group or acylation or carbamoylation reactions. Such methods and procedures also include O2'-alkylation reactions and alkylation reactions after inclusion of other C2' attached groups like amino or mercapto. Yet another possibility is oxidation of the 2'-hydroxy group to give an aldehyde functionality, which may be further modified by e.g. reaction with nucleophiles, or to give a carboxy functionality, which may be further modified by e.g. reaction with nucleophiles after conversion of the carboxy functionality into an antivated derivative like an active ester.

In another embodiment of the disclosure, the method to prepare monomeric building blocks suitable for incorporation of the Monomers like F-J, but "inversed" (like Monomers D and E can be considered "inversed") such that the O2' atom is phosphitylated and it is the 3'-hydroxy group that is converted into another group such that the C3' atom is linked to a functionality other that a hydroxy group, comprises among the key steps starting from a ribonucleoside (for example a O5'-DMT protected ribonucleoside) 2',3'-glycol cleavage, reduction of the resulting intermediate, selective O2'-protection, conversion of the 3'-hydroxy group, O2'-deprotection and O2'-phosphitylation. The O2'-protection can for example be performed by silylation or acylation, or a combination of the both. Other protecting groups may also be applied as would be clear for a person skilled in the art. The conversion of the 3'-hydroxy group into another group like amino, acylated amino, alkylated amino, dialkylated amino, carbamoylated amino, piperazino, acylated piperazino, alkylated piperazino, carbamoylated piperazino, mercapto, acylated mercapto, alkylated mercapto, disulfide, acylated hydroxy, alkylated hydroxy, carbamoylated hydroxy, etc., or by substituted and/or protected derivatives of these groups, can be performed using methods and procedures known to a person skilled in the art of organic synthesis. Such methods and procedures include substitution reactions on an activated derivative of the 3'-hydroxy group or acylation or carbamoylation reactions. Such methods and procedures also include O3'-alkylation reactions and alkylation reactions after inclusion of other C3' attached groups like amino or mercapto. Yet another possibility is oxidation of the 3'-hydroxy group to give an aldehyde functionality, which may be further modified by e.g. reaction with nucleophiles, or to give a carboxy functionality, which may be further modified by e.g. reaction with nucleophiles after conversion of the carboxy functionality into an antivated derivative like an active ester.

In one embodiment, a 2'-C-piperazino derivative is prepared by converting the 2'-hydroxy group into a leaving group (e.g. mesylate derivative) followed by reaction with a large excess of piperazine. This for example can be performed as a step toward synthesis of a phosphoramidite of structure Amidite J (see figure below).

In yet another embodiment, the disclosure comprises methods to prepare monomeric building blocks suitable for incorporation of the hydroxymethyl substituted monomers of the disclosure carrying groups or functionalities at the C1' atom (ribonucleoside nomenclature) that is different from a natural nucleobase. Such groups or functionalities, that may contain protecting groups, include e.g. pyrene, perylene, fluorophores, hydrogen, alkyl, reactive groups and heterocycles other than the natural nucleobases.

In yet another embodiment, the disclosure comprises methods to prepare monomeric building blocks suitable for incorporation of the hydroxymethyl substituted monomers of the disclosure that are constituted as H-phosphonate derivatives instead of phosphoramidite derivatives.

Below are shown examples of structures of some preferred embodiments of the disclosure with respect to phosphoramidite (=amidite) building blocks (DMT=4,4'-dimethoxytrityl; Base=natural nucleobase; CEtO=cyanoethoxy):

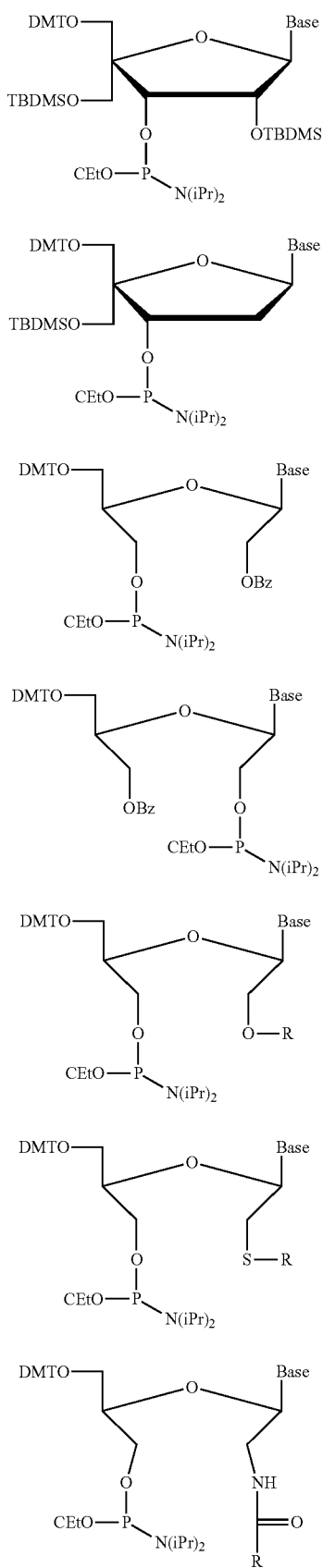

Amidite B

Amidite C

Amidite D

Amidite E

Amidite F

Amidite G

Amidite H

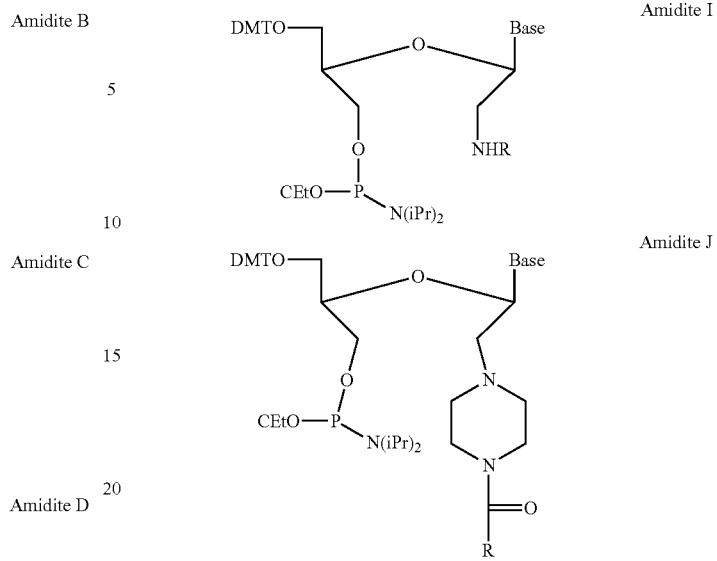

Amidite I

Amidite J

R = alkyl, cholesteryl derivatives, fluorophores, polyamines, fatty acids, amino acids, saccharides or polypeptides, etc.

In a ninth aspect of this disclosure, an oligonucleotide comprising acyclic oligonucleotides is provided. A ninth aspect of the disclosure is an oligonucleotide comprising a hydroxymethyl substituted nucleomonomer. As will be apparent from the description and the examples section such oligonucleotide has various uses and advantages.

In a preferred embodiment, the hydroxymethyl substituted nucleomonomer is a 2'-3'-seco-nucleomonomer. Oligonucleotides of the disclosure comprising hydroxymethyl substituted nucleomonomers have surprisingly been found to be substrates cellular enzymes of the RNAi machinery and in some instances, these oligonucleotides are even better substrates than an identical oligonucleotide without hydroxymethyl substituted nucleomonomers.

Preferably, the hydroxymethyl substituted nucleomonomer is selected from the group consisting of monomer E, F, G, H, I or J (see FIG. 1). As will be clear to a person of ordinary skill in the art, G, F, H, I and J can all be made from synthetic precursors of monomer D. As indicated in FIG. 2, the acyclic monomers may be transformed into derivatives carrying conjugating groups such cholesterol derivatives, alkyl, fluorophores, polyamines, amino acids, saccharides, oligonucoeotides and/or polypeptides. Such conjugating groups may e.g. be useful for better biostability and/or biodistribution when the oligonucleotide is used for modulating the activity of target mRNAs in cells, organs or organisms.

The length of the oligonucleotide is preferably from 10 to 40 nucleomonomers. Even more preferred is a length from 18 to 30 nucleomonomers.

In a preferred embodiment, the oligonucleotide of the disclosure comprises less than 5 hydroxymethyl substituted nucleomonomers. In another preferred embodiment, the oligonucleotide comprises no more than 1 hydroxymethyl substituted nucleomonomer per 5 nucleomonomers other than hydroxymethyl substituted nucleomonomers. Even more preferred is no more than 1 acyclic monomer per 8 nucleomonomers other than hydroxymethyl substituted nucleomonomers. If the number of hydroxymethyl substituted nucleomonomer gets too high, the binding affinity of the oligonucleotide of the disclosure to a complementary nucleic acid is compromised. In another embodiment, the oligonucleotide comprises from 1 to 5 hydroxymethyl substituted nucleomonomers.

In a preferred embodiment, hydroxymethyl substituted nucleomonomers are present in position 1, 2, 3, 4, 5, 6, 7, and/or 8, and more preferably in positions 2, 3, 4, 5, 6, and/or 7 of the oligonucleotide. The positions are counted from the 5' end of the oligonucleotide. Hydroxymethyl substituted nucleomonomers in these regions will reduce or prevent the oligonucleotide from acting as a microRNA, as these positions correspond to the so-called seed region of a microRNA. This is relevant e.g. where the oligonucleotide is intended to function as the guide strand of an siRNA.

In a preferred embodiment, all hydroxymethyl substituted nucleomonomers in the antisense strand are present in positions 9, 10, 11, 12, 13, 14, 15, and/or 16, wherein the positions are counted from the 5'-end of the antisense strand. Even more preferably, the hydroxymethyl substituted nucleomonomers in the antisense strand is present in position 9, 10, and/or 11. Thus, presence of hydroxymethyl substituted nucleomonomers in the aforementioned regions will induce the antisense strand to act as a microRNA, i.e. ensure that the siRNA effect will be minimal and the microRNA effect much higher.

In a preferred embodiment, the oligonucleotide does not comprise DNA sequences of more than 8 consecutive DNA monomers. Even more preferred is no more than 6 consecutive DNA monomers and most preferably in no more than 4 consecutive DNA monomers. Consecutive DNA monomers typically will enable the oligonucleotide to activate RNase H when bound to a complementary RNA, which leads to degradation of the RNA. In some embodiments of the disclosure, this is not desirable. Thus, in a further embodiment, the oligonucleotide does not contain any DNA monomers at all.

In other embodiments, RNase H activation is desirable and it is preferred that the oligonucleotide comprises more than 4 consecutive DNA monomers, more preferably more 6 DNA monomers and most preferably more than 8 DNA monomers.

In yet another embodiment, the oligonucleotide comprises more than 50% RNA monomers. A high degree of RNA monomers will facilitate interaction with RNA-interacting proteins, e.g. by functioning as a substrate or guide (or co-factor) for a cellular enzyme such as RISC.

In another embodiment, it is preferred that more than 80% of the monomers of the oligonucleotide are RNA monomers. In yet another embodiment, it is preferred that more than 90% of the monomers of the oligonucleotide are RNA monomers.

The oligonucleotide may also comprise nucleomonomer analogues. In one such embodiment, hydroxymethyl substituted nucleomonomers and RNA monomers make up more than 80% of all nucleomonomers. In another embodiment, acyclic monomers and RNA monomers make up more than 90% of all nucleomonomers.

When the oligonucleotide comprises nucleomonomer analogues, it is preferred that they are selected from the group consisting of 2'-O-alkyl-RNA monomers, 2'-amino-DNA monomers, 2'-fluoro-DNA monomers, LNA monomers, PNA monomers, HNA monomers, ANA monomers, FANA monomers, CeNA monomers, ENA monomers, DNA monomers and INA monomers. Nucleotide analogues are typically used to modulate binding affinity, increase biostability and in general give the oligonucleotide more drug-like properties.

In one embodiment, the oligonucleotide comprises at least 2 LNA nucleotide analogues. Hydroxymethyl substituted nucleomonomers typically decrease the melting temperature (i.e. binding affinity) of the oligonucleotide of the disclosure base paired to a complementary nucleic acid and LNA nucleomonomers may be used to counteract this decrease in melting temperature. I.e. in one embodiment, the number of hydroxymethyl substituted nucleomonomers is identical to the number of LNA nucleomonomers.

In a preferred embodiment, the oligonucleotide comprises only acyclic monomers and RNA monomers.

In another preferred embodiment, the oligonucleotide comprises only hydroxymethyl substituted nucleomonomers, RNA monomers, and LNA nucleotide analogues.

In a preferred embodiment, the oligonucleotide of the disclosure comprises one or more linkage(s) selected from the group consisting of phosphorothioate linkage, boranophosphate linkage, ethylphosphonate linkage, phosphoramidate linkage and phosphortriester linkage. Most preferred are a phosphorothioate linkage and/or a boranophosphate linkage. These linkages improve the biostability of the oligonucleotide and have also been shown to have a positive effect on the biodistribution of the oligonucleotide. In a preferred embodiment, the oligonucleotide comprises more than 50% of the aforementioned internucleotide linkages and even more preferably more than 75%. In one embodiment, all internucleotide linkages are of the aforementioned types.

In a preferred embodiment, the oligonucleotide of the disclosure is not base paired to a complementary oligonucleotide, i.e. the oligonucleotide of the disclosure is single stranded.

In yet another embodiment, the oligonucleotide is capable of mediating RISC dependent translational repression or degradation of target mRNAs complementary to the oligonucleotide. The skilled person will recognize RISC as the RNA Induced Silencing Complex and understand that in this embodiment, the oligonucleotide will act as a guide sequence for RISC and thereby guide RISC to RNA oligonucleotides, typically mRNAs that harbor partial or full complementarity to the oligonucleotide of the disclosure. When the oligonucleotide guides RISC to mRNA targets of partial complementarity, the oligonucleotide may be seen as a microRNA mimic and when the oligonucleotide guides RISC to mRNA targets of full complementarity; it may be seen as a single or double stranded siRNA.

RISC dependence may be assessed in cell lines by knocking out components of RISC using siRNA against the mRNAs encoding the RISC components and evaluate the activity of the oligonucleotide in the knock-out cell line. Such experiments are well known to those skilled in the art.

In a tenth aspect of this disclosure, an RNA duplex comprising oligonucleotide of disclosure is provided. A tenth aspect of the disclosure is an RNA duplex comprising a first oligonucleotide according to the disclosure and a second oligonucleotide. In a preferred embodiment, the second oligonucleotide of the RNA duplex is also an oligonucleotide of the disclosure. Embodiments described with relation to the RNA complexes of the disclosure in the first aspect, are also applicable to RNA duplexes of the tenth aspect.

Preferably, the RNA duplex of the disclosure comprises a number of base pairs from 15 to 40 and in a preferred embodiment, comprises a number of base pairs selected from the group of 18 base pairs, 19 base pairs, 20 base pairs, 21 base pairs, 22 base pairs and 23 base pairs.

In yet another embodiment, the RNA duplex comprises a number of base pairs from 25 to 30, more preferably from 26 to 28 and most preferably 27 base pairs. Such RNA duplexes may be referred to as dicer substrate RNAs.

In a preferred embodiment, the RNA duplex of the disclosure comprises an overhang. In another embodiment, the RNA duplex comprises two overhangs. In still another embodiment, the first oligonucleotide comprises a 3'-overhang. In still another embodiment, the second oligonucleotide comprises a 3'-overhang. Preferably, the length of the overhang is from 1 to 8 nucleotides and even more preferably, the length of the overhang is selected from the group consisting of overhangs with a length of 1 nucleotide, 2 nucleotides and 3 nucleotides.

In another embodiment, the RNA duplex comprises at least one blunt end. In another embodiment, the RNA duplex is blunt ended in both ends.

In a preferred embodiment, the RNA duplex comprises a double-stranded region of 18-22 base pairs, wherein the first oligonucleotide and the second oligonucleotide each comprise a 3'-overhang of 1-3 nucleotides. Such RNA duplex will be recognized as a canonical siRNA (short interfering RNA).

In one embodiment, one strand of the RNA duplex is discontinuous as described in detail in the first aspect.

In one embodiment, the RNA duplex is capable of mediating translational repression or degradation of target mRNA complementary to the first or the second oligonucleotide of the RNA duplex, i.e. the RNA duplex will function as e.g. an siRNA, microRNA or pre-microRNA.

In one embodiment, the RNA duplex is capable of mediating translational repression or degradation of target mRNA while inducing reduced off-target effects as compared to an identical RNA duplex with RNA monomers instead of acyclic monomers.

In another embodiment, the RNA duplex is capable of mediating translational repression or degradation of target mRNA while inducing reduced off-target effects when specifically an acyclic monomer is positioned in position 5-10 in the guide (antisense) strand of an siRNA duplex, wherein the position is counted from the 5' end of the oligonucleotide.

In another embodiment, the RNA duplex is capable of mediating translational repression or degradation of target mRNA while inducing reduced off-target effects when specifically an acyclic monomer is positioned in position 6-8 in the guide (antisense) strand of an siRNA duplex. In another embodiment, the RNA duplex comprising one or more hydroxymethyl substituted nucleomonomers in the guide strand has a reduced capability of the guide strand to induce microRNA-type effects.

In one embodiment, the RNA duplex is capable of mediating RNA targeting, e.g. gene silencing or RNA interference, with increased potency as compared to an identical RNA duplex with RNA monomers instead of acyclic monomers.

In one embodiment, the RNA duplex is capable of mediating translational repression or degradation of target mRNA with prolonged potency as compared to an identical RNA duplex with RNA monomers instead of acyclic monomers.

In one embodiment, the RNA duplex is capable of mediating translational repression or degradation of target mRNA wherein the RNA duplex has improved biostability as compared to an identical RNA duplex with RNA monomers instead of acyclic monomers.

In yet another embodiment, the RNA duplex is capable of mediating translational repression or degradation of target mRNA wherein the RNA duplex has reduced immune stimulation as compared to an identical RNA duplex with RNA monomers instead of acyclic monomers.

The RNA complexes of this disclosure may be targeted to various genes. Examples of human genes suitable as targets include TNF, FLT1, the VEGF family, the ERBB family, the PDGFR family, BCR-ABL, and the MAPK family, among others. Examples of human genes suitable as targets and nucleic acid sequences thereto include those disclosed in PCT/US08/55333, PCT/US08/55339, PCT/US08/55340, PCT/US08/55341, PCT/US08/55350, PCT/US08/55353, PCT/US08/55356, PCT/US08/55357, PCT/US08/55360, PCT/US08/55362, PCT/US08/55365, PCT/US08/55366, PCT/US08/55369, PCT/US08/55370, PCT/US08/55371, PCT/US08/55372, PCT/US08/55373, PCT/US08/55374, PCT/US08/55375, PCT/US08/55376, PCT/US08/55377, PCT/US08/55378, PCT/US08/55380, PCT/US08/55381, PCT/US08/55382, PCT/US08/55383, PCT/US08/55385, PCT/US08/55386, PCT/US08/55505, PCT/US08/55511, PCT/US08/55515, PCT/US08/55516, PCT/US08/55519, PCT/US08/55524, PCT/US08/55526, PCT/US08/55527, PCT/US08/55532, PCT/US08/55533, PCT/US08/55542, PCT/US08/55548, PCT/US08/55550, PCT/US08/55551, PCT/US08/55554, PCT/US08/55556, PCT/US08/55560, PCT/US08/55563, PCT/US08/55597, PCT/US08/55599, PCT/US08/55601, PCT/US08/55603, PCT/US08/55604, PCT/US08/55606, PCT/US08/55608, PCT/US08/55611, PCT/US08/55612, PCT/US08/55615, PCT/US08/55618, PCT/US08/55622, PCT/US08/55625, PCT/US08/55627, PCT/US08/55631, PCT/US08/55635, PCT/US08/55644, PCT/US08/55649, PCT/US08/55651, PCT/US08/55662, PCT/US08/55672, PCT/US08/55676, PCT/US08/55678, PCT/US08/55695, PCT/US08/55697, PCT/US08/55698, PCT/US08/55701, PCT/US08/55704, PCT/US08/55708, PCT/US08/55709, and PCT/US08/55711, all hereby incorporated by reference.

EXAMPLES

Example 1

Synthesis of the RNA Complexes of this Disclosure

Procedures for preparation of the phosphoramidite building blocks for automated DNA/RNA synthesis of the hydroxymethyl substituted monomers of the RNA complexes of the disclosure have been reported [thymine derivatives; K. D. Nielsen et al., *Bioorg. Med. Chem.* 1995, 3, 1493; H. Thrane et al., *Tetrahedron* 1995, 51, 10389; P. Nielsen et al., *Bioorg. Med. Chem.* 1995, 3, 19].

The incorporation of these hydroxymethyl substituted monomers into the RNA complexes of the disclosure follows standard methods for a) RNA synthesis on an automated RNA synthesizer, b) RNA work-up, c) RNA purification and d) RNA isolation [F. Eckstein, Oligonucleotides and Analogues, IRL Press, Oxford University Press, 1991]. This demonstrates that hydroxymethyl substituted RNA oligonucleotides (=RNA strands) and RNA complexes can be synthesised using known phosphoramidite derivatives using the standard techniques for RNA synthesis.

LNA is an oligonucleotide containing one or more 2'-O,4'-C-methylene-linked ribonucleotides (LNA nucleotides) [M. Petersen and J. Wengel, *Trends Biotechnol.* 2003, 21, 74-81]. LNA-modified siRNA is an siRNA construct containing one or more LNA monomers. Known methods have been used to incorporate LNA nucleotides into the RNA complexes to the disclosure by use of the commercially available LNA phosphoramidites [Pfundheller, Sørensen, Lomholt, Johansen, Koch and Wengel, J. "Locked Nucleic Acid Synthesis", *Methods Mol. Biol.* 2004, vol. 288 (Oligonucleotide Synthesis), 127-145, P. Herdewijn, Ed., Humana Press Inc.]

Hydroxymethyl substituted siRNA ("hydroxymethyl substituted small interfering RNA) is an siRNA construct containing one or more hydroxymethyl substituted nucleomonomer (see FIG. 1 for structures of the hydroxymethyl substituted nucleomonomer). The monomers exemplified are shown below:

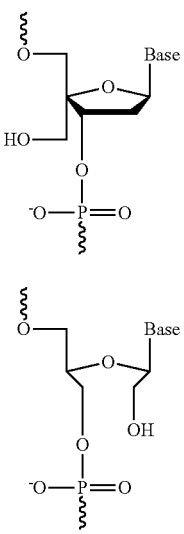

Monomer C (C,T)

Monomer D (X)

The following examples illustrate the design of hydroxymethyl subsitituted RNA complexes, and is not limiting to the design of other RNA constructs not expressly disclosed herein. Thus are, for example, blunt ended siRNA duplexes, shorter or longer siRNA duplexes than the ones exemplified herein, single stranded antisense RNA molecules (RNA complexes) and RNA complexes comprising an antisense strand and a discontinued passenger strand (the "passenger strand" can also be called the "sense strand").

Procedures for preparation of example phosphoramidite derivatives of adenine, guanine, cytosine and uracil are disclosed in patent application serial number PCT/US2008/064417, example 11, the contents of which is hereby incorporated by reference in its entirety.

Example 2

Hydroxymethyl Nucleomonomer Substitution Patterns in RNA Complexes

Incorporation of hydroxymethyl nucleomonomers (e.g., monomer D) in specific positions in an RNA complex affects the gene silencing activity, cytokine induction, strand activity, "off-target" effects, thermal stability of the RNA complex, and in the case of Dicer substrate RNA complexes, Dicer processing of the RNA complex.

Example substitution patterns of hydroxymethyl nucleomonomers in a RISC RNA complex and Dicer RNA complex are provided below. The number of nucleomonomers of each strand of an RNA complex (double-stranded RNA) is represented (i.e., sequence independent) by a string of X's or H's. Each "X" independently and for each occurrence may be any nucleoside (e.g., adenine, guanine, cytosine, uracil, thymine, or any analog or derivative thereof), while each "H" independently and for each occurrence may be a non-nucleotide hydroxymethyl nucleomonomer (e.g., monomer D with any nucleobase). In each case, the sense strand and antisense strand anneal to form a double stranded region due to base pairing between each strand. The purpose of these diagrams is to show the substitution patterns of RNA complexes with hydroxymethyl nucleomonomers independent of sequence.

Hydroxymethyl Nucleomonomer Substitution Patterns of a RISC RNA Complex

For each RNA complexes below, the sense and antisense strand are each 21 nucleomonomers in length (except for Motif # P-1 and P-1/G7 where the sense strand is 22 nucleomonomers in length) comprising either nucleosides or non-nucleotide hydroxymethyl nucleomonomers (e.g., monomer D). Each complex is identified with a "Motif #" and the position of the hydroxymethyl nucleomonomer(s) or "H" is provided. The position of each "H" in each strand is determined by counting from the 5'-end of the strand in which the hydroxymethyl nucleomonomer(s) is located. For any RNA complex disclosed herein, position −1 (minus 1) or position 1 indicates that the hydroxymethyl nucleomonomer is the 3'-most nucleomonomer of that strand (or the last nucleomonomer at the 3'-end of that strand). For the RISC length RNA complexes below, positions 21 and 22 of either the sense or antisense strand indicates that the nucleomonomers occupy the last two positions of that strand counting from the 5'-end of the strand.

| Motif # | | RNA Complex | | Strand | Position(s) |
|---|---|---|---|---|---|
| 22 | 5' | XXXXXXXXXXXXXXXXXHXXX | 3' | SENSE | 18 |
|  | 3' | XXXXXXXXXXXXXXXXXXXXX | 5' | ANTISENSE | |
| 24 | 5' | XHXXXXXXXXXXXXXXXXXXX | 3' | SENSE | 2 |
|  | 3' | XXXXXXXXXXXXXXXXXXXXX | 5' | ANTISENSE | |
| 26 | 5' | XXXXXXXXHHXXXXXXXXXXX | 3' | SENSE | 9, 10 |
|  | 3' | XXXXXXXXXXXXXXXXXXXXX | 5' | ANTISENSE | |
| 27 | 5' | XXXXXXXXXXXXXXXXXXXXX | 3' | SENSE | |
|  | 3' | XXXXXXXXXXXXXXXXXXXHX | 5' | ANTISENSE | 2 |
| 31 | 5' | XXXXXXXXXXXXXXXXXXXHH | 3' | SENSE | 20, 21 |
|  | 3' | HHXXXXXXXXXXXXXXXXXXX | 5' | ANTISENSE | 20, 21 |
| 32 | 5' | XXXXXXXXXXXXXHXXXHXXX | 3' | SENSE | 14, 18 |
|  | 3' | XXXXXXXXXXXXXXXXXXXXX | 5' | ANTISENSE | |
| 33 | 5' | XHXXXHXXXXXXXXXXXXXXX | 3' | SENSE | 2, 6 |
|  | 3' | XXXXXXXXXXXXXXXXXXXXX | 5' | ANTISENSE | |
| 34 | 5' | XXXXXXXXXXXXXXXXXXXXX | 3' | SENSE | |
|  | 3' | XXXXXXXXXXXXXXHXXXHX | 5' | ANTISENSE | 2, 6 |

-continued

| Motif # | RNA Complex | | | Strand | Position(s) |
|---|---|---|---|---|---|
| 35 | 5' XXXXXXXXXXXXXXXXXXXXXXXXX | 3' | | SENSE | |
| | 3' XXXXXXXXXXXXXXXHXXXXX | 5' | | ANTISENSE | 6 |
| 36 | 5' XXXXXXXXXXXXXXXXXXXXXXXXX | 3' | | SENSE | |
| | 3' XXXXXXXXXXXXXXXXHXXXXXX | 5' | | ANTISENSE | 7 |
| 37 | 5' XXXXXXXXXXXXXHXXXXXXX | 3' | | SENSE | 14 |
| | 3' XXXXXXXXXXXXXXXXXXXXXXXXX | 5' | | ANTISENSE | |
| 38 | 5' XXXHXXXXXXXXXHXXXXXXX | 3' | | SENSE | 4, 14 |
| | 3' XXXXXXXXXXXXXXXXXXXXXXXXX | 5' | | ANTISENSE | |
| 39 | 5' XXXXXXXXXXXXXXXXXXXXXXXXX | 3' | | SENSE | |
| | 3' XXXXXXXXXXXXXXXXXXHXXX | 5' | | ANTISENSE | 4 |
| 40 | 5' XXXXXXXXXXXXXXXXXXXXXXXXX | 3' | | SENSE | |
| | 3' XXXXXXXHXXXXXXXXXHXXX | 5' | | ANTISENSE | 4, 14 |
| G1 | 5' XXXXXXXXXXXXXXXXXXXXXHH | 3' | | SENSE | 20, 21 |
| | 3' HXXXXXXXXXXXXXXXXXXXXH | 5' | | ANTISENSE | 1, 20, 21 |
| G2 | 5' XXXXXXXXXXXXXXXXXXXXXHH | 3' | | SENSE | 20, 21 |
| | 3' HXXXXXXXXXXXXXXXXXXXHX | 5' | | ANTISENSE | 2, 20, 21 |
| G3 | 5' XXXXXXXXXXXXXXXXXXXXXHH | 3' | | SENSE | 20, 21 |
| | 3' HXXXXXXXXXXXXXXXXXHXX | 5' | | ANTISENSE | 3, 20, 21 |
| G5 | 5' XXXXXXXXXXXXXXXXXXXXXHH | 3' | | SENSE | 20, 21 |
| | 3' HXXXXXXXXXXXXXXXHXXXXX | 5' | | ANTISENSE | 5, 20, 21 |
| G6 | 5' XXXXXXXXXXXXXXXXXXXXXHH | 3' | | SENSE | 20, 21 |
| | 3' HXXXXXXXXXXXXXXHXXXXX | 5' | | ANTISENSE | 6, 20, 21 |
| G7 | 5' XXXXXXXXXXXXXXXXXXXXXHH | 3' | | SENSE | 20, 21 |
| | 3' HXXXXXXXXXXXXXHXXXXXX | 5' | | ANTISENSE | 7, 20, 21 |
| G8 | 5' XXXXXXXXXXXXXXXXXXXXXHH | 3' | | SENSE | 20, 21 |
| | 3' HXXXXXXXXXXXXHXXXXXXX | 5' | | ANTISENSE | 8, 20, 21 |
| G10 | 5' XXXXXXXXXXXXXXXXXXXXXHH | 3' | | SENSE | 20, 21 |
| | 3' HXXXXXXXXXXHXXXXXXXXX | 5' | | ANTISENSE | 10, 20, 21 |
| G15 | 5' XXXXXXXXXXXXXXXXXXXXXHH | 3' | | SENSE | 20, 21 |
| | 3' HHXXXXXHXXXXXXXXXXXXX | 5' | | ANTISENSE | 15,20,21 |
| P-1 | 5' HXXXXXXXXXXXXXXXXXXXXHH | 3' | | SENSE | -1, 20, 21 |
| | 3' HHXXXXXXXXXXXXXXXXXXX | 5' | | ANTISENSE | 20, 21 |
| P1 | 5' HXXXXXXXXXXXXXXXXXXXXHH | 3' | | SENSE | 1, 20, 21 |
| | 3' HHXXXXXXXXXXXXXXXXXXX | 5' | | ANTISENSE | 20, 21 |
| P2 | 5' XHXXXXXXXXXXXXXXXXXXXHH | 3' | | SENSE | 2, 20, 21 |
| | 3' HHXXXXXXXXXXXXXXXXXXX | 5' | | ANTISENSE | 20, 21 |
| P3 | 5' XXHXXXXXXXXXXXXXXXXXXHH | 3' | | SENSE | 3, 20, 21 |
| | 3' HHXXXXXXXXXXXXXXXXXXX | 5' | | ANTISENSE | 20, 21 |
| P2/G2 | 5' XHXXXXXXXXXXXXXXXXXXXHH | 3' | | SENSE | 2, 20, 21 |
| | 3' HHXXXXXXXXXXXXXXXXXHX | 5' | | ANTISENSE | 2, 20, 21 |
| P-1/G7 | 5' HXXXXXXXXXXXXXXXXXXXXHH | 3' | | SENSE | -1, 20, 21 |
| | 3' HHXXXXXXXXXXXXHXXXXXX | 5' | | ANTISENSE | 7, 20, 21 |

Hydroxymethyl Nucleomonomer Substitution Patterns of a Dicer RNA Complex

For each RNA complex below, the sense is 25 nucleomonomers in length and the antisense strand is 27 nucleomonomer is length (25/27-mer) comprising either nucleosides or non-nucleotide hydroxymethyl nucleomonomers (e.g., monomer D). Each complex is identified with a "Motif #" and the position of the hydroxymethyl nucleomonomer(s) or "H" is provided. The position of each "H" in each strand is determined by counting from the 5'-end of the strand in which the hydroxymethyl nucleomonomer(s) is located.

RNA complexes having motif 10 have one blunt-ended and a 25 base pair duplex region with two non-nucleotide hydroxymethyl nucleomonomers attached to 5'-end of the antisense strand (or at positions 26 and 27 in the antisense strand counting from the 5'-end of the antisense strand; the hydroxymethyl nucleomonomers occupy the last two positions of that strand counting from the 5'-end of the strand), and one non-nucleotide hydroxymethyl nucleomonomer attached to 3'-end of the sense strand (or at position 25 in the sense strand counting from the 5'-end of the sense strand; the hydroxymethyl nucleomonomer occupies the last position of that strand counting from the 5'-end of the strand).

| Motif # | | RNA Complex | | Strand | Position(s) |
|---|---|---|---|---|---|
| 2 | 5' | XXXXXXXXXXXXXXXXXXXXHHXXX | 3' | SENSE | 21, 22 |
| | 3' | XXXXXXXXXXXXXXXXXXXXHHXXXXX | 5' | ANTISENSE | 6, 7 |
| 3 | 5' | XXXXXXXXXXXXXXXXXXXXHHXXX | 3' | SENSE | 21, 22 |
| | 3' | XXXXXXXXXXXXXXXXXXXXXXXXXXX | 5' | ANTISENSE | |
| 4 | 5' | XXXXXXXXXXXXXXXXXXXXXXXXX | 3' | SENSE | |
| | 3' | XXXXXXXXXXXXXXXXXXXXHHXXXXX | 5' | ANTISENSE | 6, 7 |
| 7 | 5' | XHXXXHXXXXXXXXXXXXXXXXXXX | 3' | SENSE | 2, 6 |
| | 3' | XXXXXXXXXXXXXXXXXXXXXXXXXXX | 5' | ANTISENSE | |
| 8 | 5' | XXXXXXXXXXXXXXXXXXXXXXXXX | 3' | SENSE | |
| | 3' | XXXXXXXXXXXXXXXHXXXHXXXXXXX | 5' | ANTISENSE | 8, 12 |
| 9 | 5' | XXXXXXXXXXXXXXXXXXXXXXXXX | 3' | SENSE | |
| | 3' | XXXXXXXXXXXXXXXHXXXXXXXXXXX | 5' | ANTISENSE | 12 |
| 10 | 5' | XXXXXXXXXXXXXXXXXXXXXXXXH | 3' | SENSE | 25 |
| | 3' | HHXXXXXXXXXXXXXXXXXXXXXXXXX | 5' | ANTISENSE | 26, 27 |

Example 3

Position Specific Effects of Hydroxymethyl Nucleomonomer Substitution in RISC Length RNA Complexes The substitution patterns (motifs) represented in the example above were applied to different sequence specific RISC length RNA complexes. These RNA complexes are provided in tables 1-7 below. Hydroxymethyl substituted monomer(s) in the sequences of the table below are identified as "unaH" where H is the one letter code for the nucleobase (e.g., "unaC" indicates that the cytosine comprises a hydroxymethyl substituted monomer).

TABLE 1

RISC Length RNA Complexes that Target Influenza PB2 Gene

| RNA Complex Identifier (Motif#) | Sense Sequence 5' to 3' orientation | Antisense Sequence 5' to 3' orientation |
|---|---|---|
| G3789 unmodified | CGGGACUCUAGCAUACUUATT (SEQ ID NO: 1) | UAAGUAUGCUAGAGUCCCGTT (SEQ ID NO: 12) |
| G3789 (22) | CGGGACUCUAGCAUACUunaUATT (SEQ ID NO: 2) | UAAGUAUGCUAGAGUCCCGTT (SEQ ID NO: 13) |
| G3789 (24) | CunaGGGACUCUAGCAUACUUATT (SEQ ID NO: 3) | UAAGUAUGCUAGAGUCCCGTT (SEQ ID NO: 14) |
| G3789 (26) | CGGGACUCunaUunaAGCAUACUUATT (SEQ ID NO: 4) | UAAGUAUGCUAGAGUCCCGTT (SEQ ID NO: 15) |
| G3789 (27) | CGGGACUCUAGCAUACUUATT (SEQ ID NO: 5) | UunaAAGUAUGCUAGAGUCCCGTT (SEQ ID NO: 16) |
| G3789 (31) | CGGGACUCUAGCAUACUUAunaUunaU (SEQ ID NO: 6) | UAAGUAUGCUAGAGUCCCGunaUunaU (SEQ ID NO: 17) |
| G3789 (32) | CGGGACUCUAGCAunaUACUunaUATT (SEQ ID NO: 7) | UAAGUAUGCUAGAGUCCCGTT (SEQ ID NO: 18) |
| G3789 (33) | CunaGGGAunaCUCUAGCAUACUUATT (SEQ ID NO: 8) | UAAGUAUGCUAGAGUCCCGTT (SEQ ID NO: 19) |
| G3789 (34) | CGGGACUCUAGCAUACUUATT (SEQ ID NO: 9) | UunaAAGUunaAUGCUAGAGUCCCGTT (SEQ ID NO: 20) |
| G3789 (35) | CGGGACUCUAGCAUACUUATT (SEQ ID NO: 10) | UAAGUunaAUGCUAGAGUCCCGTT (SEQ ID NO: 21) |
| G3789(36) | CGGGACUCUAGCAUACUUATT (SEQ ID NO: 11) | UAAGUAunaUGCUAGAGUCCCGTT (SEQ ID NO: 22) |

TABLE 2

RISC Length RNA Complexes that Target Influenza PA Gene

| RNA Complex Identifier (Motif #) | Sense Sequence 5' to 3' orientation | Antisense Sequence 5' to 3' orientation |
|---|---|---|
| G8282 unmodified | GCAAUUGAGGAGUGCCUGATT (SEQ ID NO: 23) | UCAGGCACUCCUCAAUUGCTT (SEQ ID NO: 34) |
| G8282 (22) | GCAAUUGAGGAGUGCCUunaGATT (SEQ ID NO: 24) | UCAGGCACUCCUCAAUUGCTT (SEQ ID NO: 35) |
| G8282 (24) | GunaCAAUUGAGGAGUGCCUGATT (SEQ ID NO: 25) | UCAGGCACUCCUCAAUUGCTT (SEQ ID NO: 36) |
| G8282 (26) | GCAAUUGAunaGunaGAGUGCCUGATT (SEQ ID NO: 26) | UCAGGCACUCCUCAAUUGCTT (SEQ ID NO: 37) |
| G8282 (27) | GCAAUUGAGGAGUGCCUGATT (SEQ ID NO: 27) | UunaCAGGCACUCCUCAAUUGCTT (SEQ ID NO: 38) |
| G8282 (31) | GCAAUUGAGGAGUGCCUGAunaUunaU (SEQ ID NO: 28) | UCAGGCACUCCUCAAUUGCunaUunaU (SEQ ID NO: 39) |
| G8282 (3) | GCAAUUGAGGAGUunaGCCUunaGATT (SEQ ID NO: 29) | UCAGGCACUCCUCAAUUGCTT (SEQ ID NO: 40) |
| G8282 (33) | GunaCAAUunaUGAGGAGUGCCUGATT (SEQ ID NO: 30) | UCAGGCACUCCUCAAUUGCTT (SEQ ID NO: 41) |
| G8282 (34) | GCAAUUGAGGAGUGCCUGATT (SEQ ID NO: 31) | UunaCAGGunaCACUCCUCAAUUGCTT (SEQ ID NO: 42) |
| G8282 (35) | GCAAUUGAGGAGUGCCUGATT (SEQ ID NO: 32) | UCAGGunaCACUCCUCAAUUGCTT (SEQ ID NO: 43) |
| G8282 (36) | GCAAUUGAGGAGUGCCUGATT (SEQ ID NO: 33) | UCAGGCunaACUCCUCAAUUGCTT (SEQ ID NO: 44) |

TABLE 3

RISC Length RNA Complexes that Target Influenza NP Gene

| RNA Complex Identifier (Motif #) | Sense Sequence 5' to 3' orientation | Antisense Sequence 5' to 3' orientation |
|---|---|---|
| G1498 unmodified | GGAUCUUAUUUCUUCGGAGTT (SEQ ID NO: 45) | CUCCGAAGAAAUAAGAUCCTT (SEQ ID NO: 56) |
| G1498 (22) | GGAUCUUAUUUCUUCGGunaAGTT (SEQ ID NO: 46) | CUCCGAAGAAAUAAGAUCCTT (SEQ ID NO: 57) |
| G1498 (24) | GunaGAUCUUAUUUCUUCGGAGTT (SEQ ID NO: 47) | CUCCGAAGAAAUAAGAUCCTT (SEQ ID NO: 58) |
| G1498 (26) | GGAUCUUAunaUunaUUCUUCGGAGTT (SEQ ID NO: 48) | CUCCGAAGAAAUAAGAUCCTT (SEQ ID NO: 59) |
| G1498 (27) | GGAUCUUAUUUCUUCGGAGTT (SEQ ID NO: 49) | CunaUCCGAAGAAAUAAGAUCCTT (SEQ ID NO: 60) |
| G1498 (31) | GGAUCUUAUUUCUUCGGAGunaUunaU (SEQ ID NO: 50) | CUCCGAAGAAAUAAGAUCCunaUunaU (SEQ ID NO: 61) |
| G1498 (32) | GGAUCUUAUUUCUunaUCGGunaAGTT (SEQ ID NO: 51) | CUCCGAAGAAAUAAGAUCCTT (SEQ ID NO: 62) |
| G1498 (33) | GunaGAUCunaUUAUUUCUUCGGAGTT (SEQ ID NO: 52) | CUCCGAAGAAAUAAGAUCCTT (SEQ ID NO: 63) |
| G1498 (34) | GGAUCUUAUUUCUUCGGAGTT (SEQ ID NO: 53) | CunaUCCGunaAAGAAAUAAGAUCCTT (SEQ ID NO: 64) |
| G1498 (35) | GGAUCUUAUUUCUUCGGAGTT (SEQ ID NO: 54) | CUCCGunaAAGAAAUAAGAUCCTT (SEQ ID NO: 65) |

TABLE 3-continued

RISC Length RNA Complexes that Target Influenza NP Gene

| RNA Complex Identifier (Motif #) | Sense Sequence 5' to 3' orientation | Antisense Sequence 5' to 3' orientation |
|---|---|---|
| G1498 (36) | GGAUCUUAUUCUUCGGAGTT (SEQ ID NO: 55) | CUCCGAunaAGAAAUAAGAUCCTT (SEQ ID NO: 66) |

TABLE 4

RISC Length RNA Complexes that Target the SOS1 Gene

| RNA Complex Identifier (Motif #) | Sense Sequence 5' to 3' orientation | Antisense Sequence 5' to 3' orientation |
|---|---|---|
| SOS1:364 unmodified | AUUGACCACCAGGUUUCUGTT (SEQ ID NO: 67) | CAGAAACCUGGUGGUCAAUTT (SEQ ID NO: 78) |
| SOS1:364 (22) | AUUGACCACCAGGUUUCunaUGTT (SEQ ID NO: 68) | CAGAAACCUGGUGGUCAAUTT (SEQ ID NO: 79) |
| SOS1:364 (24) | AunaUUGACCACCAGGUUUCUGTT (SEQ ID NO: 69) | CAGAAACCUGGUGGUCAAUTT (SEQ ID NO: 80) |
| SOS1:364 (26) | AUUGACCAunaCunaCAGGUUUCUGTT (SEQ ID NO: 70) | CAGAAACCUGGUGGUCAAUTT (SEQ ID NO: 81) |
| SOS1:364 (27) | AUUGACCACCAGGUUUCUGTT (SEQ ID NO: 71) | CunaAGAAACCUGGUGGUCAAUTT (SEQ ID NO: 82) |
| SOS1:364 (31) | AUUGACCACCAGGUUUCUGunaUunaU (SEQ ID NO: 72) | CAGAAACCUGGUGGUCAAUunaUunaU (SEQ ID NO: 83) |
| SOS1:364 (32) | AUUGACCACCAGGunaUUUCunaUGTT (SEQ ID NO: 73) | CAGAAACCUGGUGGUCAAUTT (SEQ ID NO: 84) |
| SOS1:364 (33) | AunaUUGAunaCCACCAGGUUUCUGTT (SEQ ID NO: 74) | CAGAAACCUGGUGGUCAAUTT (SEQ ID NO: 85) |
| SOS1:364 (34) | AUUGACCACCAGGUUUCUGTT (SEQ ID NO: 75) | CunaAGAAunaACCUGGUGGUCAAUTT (SEQ ID NO: 86) |
| SOS1:364 (35) | AUUGACCACCAGGUUUCUGTT (SEQ ID NO: 76) | CAGAAunaACCUGGUGGUCAAUTT (SEQ ID NO: 87) |
| SOS1:364 (36) | AUUGACCACCAGGUUUCUGTT (SEQ ID NO: 77) | CAGAAAunaCCUGGUGGUCAAUTT (SEQ ID NO: 88) |

TABLE 5

RISC Length RNA Complexes that Target the ApoB Gene

| RNA Complex Identifier (Motif #) | Sense Sequence 5' to 3' orientation | Antisense Sequence 5' to 3' orientation |
|---|---|---|
| ApoB:10169 unmodified | CAUCACACUGAAUACCAAUTT (SEQ ID NO: 89) | AUUGGUAUUCAGUGUGAUGTT (SEQ ID NO: 100) |
| ApoB:10169 (22) | CAUCACACUGAAUACCAunaAUTT (SEQ ID NO: 90) | AUUGGUAUUCAGUGUGAUGTT (SEQ ID NO: 101) |
| ApoB:10169 (24) | CunaAUCACACUGAAUACCAAUTT (SEQ ID NO: 91) | AUUGGUAUUCAGUGUGAUGTT (SEQ ID NO: 102) |
| ApoB:10169 (26) | CAUCACunaUunaGAAUACCAAUTT (SEQ ID NO: 92) | AUUGGUAUUCAGUGUGAUGTT (SEQ ID NO: 103) |
| ApoB:10169 (27) | CAUCACACUGAAUACCAAUTT (SEQ ID NO: 93) | AunaUUGGUAUUCAGUGUGAUGTT (SEQ ID NO: 104) |
| ApoB:10169 (31) | CAUCACACUGAAUACCAAUunaUunaU (SEQ ID NO: 94) | AUUGGUAUUCAGUGUGAUGunaUunaU (SEQ ID NO: 105) |

TABLE 5-continued

RISC Length RNA Complexes that Target the ApoB Gene

| RNA Complex Identifier (Motif #) | Sense Sequence 5' to 3' orientation | Antisense Sequence 5' to 3' orientation |
| --- | --- | --- |
| ApoB:10169 (32) | CAUCACACUGAAUunaACCAunaAUTT (SEQ ID NO: 95) | AUUGGUAUUCAGUGUGAUGTT (SEQ ID NO: 106) |
| ApoB:10169 (33) | CunaAUCAunaCACUGAAUACCAAUTT (SEQ ID NO: 96) | AUUGGUAUUCAGUGUGAUGTT (SEQ ID NO: 107) |
| ApoB:10169 (34) | CAUCACACUGAAUACCAAUTT (SEQ ID NO: 97) | AunaUUGGunaUAUUCAGUGUGAUGTT (SEQ ID NO: 108) |
| ApoB:10169 (35) | CAUCACACUGAAUACCAAUTT (SEQ ID NO: 98) | AUUGGunaUAUUCAGUGUGAUGTT (SEQ ID NO: 109) |
| ApoB:10169 (36) | CAUCACACUGAAUACCAAUTT (SEQ ID NO: 99) | AUUGGUunaAUUCAGUGUGAUGTT (SEQ ID NO: 110) |

TABLE 6

RISC Length RNA Complexes that Target the ApoB Gene

| RNA Complex Identifier (Motif #) | Sense Sequence 5' to 3' orientation | Antisense Sequence 5' to 3' orientation |
| --- | --- | --- |
| ApoB:3410 unmodified | GGACAUUCAGAACAAGAAATT (SEQ ID NO: 111) | UUUCUUGUUCUGAAUGUCCTT (SEQ ID NO: 124) |
| ApoB:3410 (31) | GGACAUUCAGAACAAGAAAunaUunaU (SEQ ID NO: 112) | UUUCUUGUUCUGAAUGUCCunaUunaU (SEQ ID NO: 125) |
| ApoB:3410 (G1) | GGACAUUCAGAACAAGAAAunaUunaU (SEQ ID NO: 113) | unaUUUCUUGUUCUGAAUGUCCunaUunaU (SEQ ID NO: 126) |
| ApoB:3410 (G2) | GGACAUUCAGAACAAGAAAunaUunaU (SEQ ID NO: 114) | UunaUUCUUGUUCUGAAUGUCCunaUunaU (SEQ ID NO: 127) |
| ApoB:3410 (G3) | GGACAUUCAGAACAAGAAAunaUunaU (SEQ ID NO: 115) | UUunaUCUUGUUCUGAAUGUCCunaUunaU (SEQ ID NO: 128) |
| ApoB:3410 (G5) | GGACAUUCAGAACAAGAAAunaUunaU (SEQ ID NO: 116) | UUUCunaUUGUUCUGAAUGUCCunaUunaU (SEQ ID NO: 129) |
| ApoB:3410 (G6) | GGACAUUCAGAACAAGAAAunaUunaU (SEQ ID NO: 117) | UUUCUunaUGUUCUGAAUGUCCunaUunaU (SEQ ID NO: 130) |
| ApoB:3410 (G7) | GGACAUUCAGAACAAGAAAunaUunaU (SEQ ID NO: 118) | UUUCUUunaGUUCUGAAUGUCCunaUunaU (SEQ ID NO: 131) |
| ApoB:3410 (G8) | GGACAUUCAGAACAAGAAAunaUunaU (SEQ ID NO: 119) | UUUCUUGunaUUCUGAAUGUCCunaUunaU (SEQ ID NO: 132) |
| ApoB:3410 (G10) | GGACAUUCAGAACAAGAAAunaUunaU (SEQ ID NO: 120) | UUUCUUGUUunaCUGAAUGUCCunaUunaU (SEQ ID NO: 133) |
| ApoB:3410 (G15) | GGACAUUCAGAACAAGAAAunaUunaU (SEQ ID NO: 121) | UUUCUUGUUCUGAAunaUGUCCunaUunaU (SEQ ID NO: 134) |
| ApoB:3410 (P-1) | unaUGGACAUUCAGAACAAGAAAunaUunaU (SEQ ID NO: 122) | UUUCUUGUUCUGAAUGUCCunaUunaU (SEQ ID NO: 135) |
| ApoB:3410 (P-1/G7) | unaUGGACAUUCAGAACAAGAAAunaUunaU (SEQ ID NO: 123) | UUUCUUunaGUUCUGAAUGUCCunaUunaU (SEQ ID NO: 136) |

TABLE 7

RISC Length RNA Complexes that Target the ICAM-1 Gene

| RNA Complex Identifier (Motif #) | Sense Sequence 5' to 3' orientation | Antisense Sequence 5' to 3' orientation |
|---|---|---|
| ICAM1:1383 unmodified | AGCUCCUGCUGAAGGCCACUU (SEQ ID NO: 137) | GUGGCCUUCAGCAGGAGCUUU (SEQ ID NO: 147) |
| ICAM1:1383 (31) | AGCUCCUGCUGAAGGCCACunaUunaU (SEQ ID NO: 138) | GUGGCCUUCAGCAGGAGCUunaUunaU (SEQ ID NO: 148) |
| ICAM1:1383 (P-1) | unaUAGCUCCUGCUGAAGGCCACunaUunaU (SEQ ID NO: 139) | GUGGCCUUCAGCAGGAGCUunaUunaU (SEQ ID NO: 149) |
| ICAM1:1383 (P1) | unaAGCUCCUGCUGAAGGCCACunaUunaU (SEQ ID NO: 140) | GUGGCCUUCAGCAGGAGCUunaUunaU (SEQ ID NO: 150) |
| ICAM1:1383 (P2) | AunaGCUCCUGCUGAAGGCCACunaUunaU (SEQ ID NO: 141) | GUGGCCUUCAGCAGGAGCUunaUunaU (SEQ ID NO: 151) |
| ICAM1:1383 (P3) | AGunaCUCCUGCUGAAGGCCACunaUunaU (SEQ ID NO: 142) | GUGGCCUUCAGCAGGAGCUunaUunaU (SEQ ID NO: 152) |
| ICAM1:1383 (G2) | AGCUCCUGCUGAAGGCCACunaUunaU (SEQ ID NO: 143) | GunaUGGCCUUCAGCAGGAGCUunaUunaU (SEQ ID NO: 153) |
| ICAM1:1383 (G7) | AGCUCCUGCUGAAGGCCACunaUunaU (SEQ ID NO: 144) | GUGGCCunaUUCAGCAGGAGCUunaUunaU (SEQ ID NO: 154) |
| ICAM1:1383 (P2, G2) | AunaGCUCCUGCUGAAGGCCACunaUunaU (SEQ ID NO: 145) | GunaUGGCCUUCAGCAGGAGCUunaUunaU (SEQ ID NO: 155) |
| ICAM1:1383 (P2, G7) | AunaGCUCCUGCUGAAGGCCACunaUunaU (SEQ ID NO: 146) | GUGGCCunaUCAGCAGGAGCUunaUunaU (SEQ ID NO: 156) |

Gene Silencing Activity of RISC Length RNA Complexes

The gene silencing activity (or "knockdown activity") of RISC length RNA complexes containing hydroxymethyl monomers (e.g., monomer D) was examined.

Briefly, for transfection in HeLa cells, multiwell plates were seeded with about 5,000 HeLa cells/well in DMEM having 10% fetal bovine serum, and incubated overnight at 37° C./5% $CO_2$. The HeLa cell medium was changed to serum-free DMEM just prior to transfection. The psiCHECK™-2 vector containing about a 1,000 base pair insert of a target gene, and an RNA complex (25 nM, 2.5 nM, and 0.25 nM for all RNA complexes identified above, except, MAPK14 RNA complexes were assayed at 2.5 nM), diluted in serum-free DMEM was mixed with diluted Lipofectamine 2000™ (LF2K) transfection reagent according to the manufacturer's instructions and then incubated at room temperature for 20 minutes. An example transfection mixture preparation includes 93 µL of Opti-MEM, 3 µL of an RNA complex, 4 µL of the psiCHECK™-2 plasmid containing the target, and 100 µL of the diluted LF2K (i.e., 1.4 µL of LF2K with 98.6 µL Opti-MEM). The LF2K/psiCHECK™-2-[target gene insert] with RNA complex solution was added to the HeLa cells and then incubated at 37° C., 5% $CO_2$ for 4.5 hours. After the co-transfection transfection (approximately 22 hours), cells were trypsinized and suspended in antibiotic-free DMEM containing 10% FBS at a concentration of $10^5$ cells per mL.

The HeLa cells transfected with RNA complexes and the psiCHECK™-2 vector were assayed for firefly and *Renilla* luciferase reporter activity by first adding Dual-Glo™ Luciferase Reagent (Promega, Madison, Wis.) for 10 minutes with shaking, and then quantifying the luminescent signal on a VICTOR³™ 1420 Multilabel Counter (PERKINELMER). After measuring the firefly luminescence, Stop & Glo® Reagent (PROMEGA, Madison, Wis.) was added for 10 minutes with shaking to simultaneously quench the firefly reaction and initiate the *Renilla luciferase* reaction, which was then quantified on a VICTOR³™ 1420 Multilabel Counter (PerkinElmer). The gene silencing activity for each RISC length RNA complex is shown in the tables below. All samples were normalized to the respective dsRNA QNeg (QIAGEN) negative control samples run in the same experiment. That is, Qneg values were set as 100% active (i.e., no knockdown), with 95% confidence intervals (CI).

Briefly, for transfection in HepG2 cells (ApoB3410 RNA complexes), multiwell plates were seeded with about 15,000 cells/well in DMEM having 10% fetal bovine serum. Transfection mixture included RNA complexes (ApoB3410 RNA complexes) combined with RNAiMAX in OptiMEM (0.05 nM, 0.5 nM or 5 nM RNA concentrations). Transfection mixture was incubated with plated HepG2 cells (total volume of 75 µL) for 24 hours. RNA was harvested from the transfected cells and qRT-PCR was performed to determine the levels of expression for ApoB and the negative control GAPDH RNA. The tables below summarize the percent knockdown of ApoB message in transfected HepG2 cells relative to the Qneg negative control siRNA.

For tables 8-14 below, a lower percentage indicates greater knockdown of the target RNA (100% indicates no knockdown). For table 14 below (ApoB3410 RNA complexes), a higher percentage indicates a greater knockdown (0% indicates no knockdown).

TABLE 8

RISC Length RNA Complexes that Target Influenza PB2 Gene

| RNA Complex Identifier | Normalized Gene Silencing Activity (rLuc/fLuc) | | |
|---|---|---|---|
| (Motif #) | 25 nM RNA | 2.5 nM RNA | 0.25 nM RNA |
| Qneg (neg. control) | 100% | 100% | 100% |
| G3789 unmodified | 12.5% | 11.2% | 12.6% |
| G3789 (22) | 9.4% | 10.9% | 12.2% |
| G3789 (24) | 11.7% | 12.8% | 16.9% |
| G3789 (26) | 26.7% | 19.7% | 22.3% |
| G3789 (27) | 57.2% | 90.6% | 109.2% |
| G3789 (31) | 13.4% | 11.1% | 17.5% |
| G3789 (32) | 12% | 14.8% | 28.7% |
| G3789 (33) | 10.3% | 14% | 30.3% |
| G3789 (34) | 86.9% | 126.4% | 124.9% |
| G3789 (35) | 11.6% | 14.4% | 18.4% |
| G3789 (36) | 17.2% | 17.5% | 17.7% |

TABLE 9

RISC Length RNA Complexes that Target Influenza PA Gene

| RNA Complex Identifier | Normalized Gene Silencing Activity (rLuc/fLuc) | | |
|---|---|---|---|
| (Motif #) | 25 nM RNA | 2.5 nM RNA | 0.25 nM RNA |
| Qneg (neg. control) | 100% | 100% | 100% |
| G8282 unmodified | 19.1% | 17.8% | 21% |
| G8282 (22) | 19.2% | 15.9% | 20.7% |
| G8282 (24) | 16.1% | 21% | 23.8% |
| G8282 (26) | 26.7% | 22.4% | 23.6% |
| G8282 (27) | 99.8% | 98.2% | 95.4% |
| G8282 (31) | 15.9% | 16.3% | 19.2% |
| G8282 (32) | 16.5% | 21.1% | 25.6% |
| G8282 (33) | 28.4% | 72.6% | 89% |
| G8282 (34) | 77.9% | 98.7% | 137.8% |
| G8282 (35) | 14.8% | 18.5% | 31.6% |
| G8282 (36) | 20.6% | 16.6% | 18.8% |

TABLE 10

RISC Length RNA Complexes that Target Influenza NP Gene

| RNA Complex Identifier | Normalized Gene Silencing Activity (rLuc/fLuc) | | |
|---|---|---|---|
| (Motif #) | 25 nM RNA | 2.5 nM RNA | 0.25 nM RNA |
| Qneg (neg. control) | 100% | 100% | 100% |
| G1498 unmodified | 16% | 16.4% | 32.4% |
| G1498 (22) | 14% | 13.4% | 15.8% |
| G1498 (24) | 19% | 27.2% | 58.5% |
| G1498 (26) | 29.9% | 43.9% | 70.1% |
| G1498 (27) | 56.8% | 74.5% | 81.4% |
| G1498 (31) | 14.9% | 17.2% | 24.9% |
| G1498 (32) | 15.2% | 16.1% | 27.1% |
| G1498 (33) | 66% | 86.3% | 83% |
| G1498 (34) | 108.8% | 104.5% | 76.5% |
| G1498 (35) | 21.1% | 21.1% | 30.5% |
| G1498 (36) | 19.6% | 19.3% | 29.2% |

TABLE 11

RISC Length RNA Complexes that Target the SOS1 Gene

| RNA Complex Identifier | Normalized Gene Silencing Activity (rLuc/fLuc) | | |
|---|---|---|---|
| (Motif #) | 25 nM RNA | 2.5 nM RNA | 0.25 nM RNA |
| Qneg (neg. control) | 100% | 100% | 100% |
| SOS1: 364 unmodified | 74.3% | 59.1% | 60.5% |
| SOS1: 364 (22) | 11.5% | 10.5% | 30.9% |
| SOS1: 364 (24) | 25.7% | 27% | 68.9% |
| SOS1: 364 (26) | 100.3% | 63.4% | 87.9% |
| SOS1: 364 (27) | 106.8% | 86.5% | 127.8% |
| SOS1: 364 (31) | 76.1% | 41.3% | 91.1% |
| SOS1: 364 (32) | 14.6% | 36.8% | 81.5% |
| SOS1: 364 (33) | 55.7% | 76.9% | 101% |
| SOS1: 364 (34) | 124.9% | 80.7% | 84% |
| SOS1: 364 (35) | 79.1% | 58.6% | 90.8% |
| SOS1: 364 (36) | 100.8% | 103% | 100.3% |

TABLE 12

RISC Length RNA Complexes that Target the ApoB Gene

| RNA Complex Identifier | Normalized Gene Silencing Activity (rLuc/fLuc) | | |
|---|---|---|---|
| (Motif #) | 25 nM RNA | 2.5 nM RNA | 0.25 nM RNA |
| Qneg (neg. control) | 100% | 100% | 100% |
| ApoB: 10169 unmodified | 6.7% | 5.4% | 7.6% |
| ApoB: 10169 (22) | 5.3% | 5.8% | 8.8% |
| ApoB: 10169 (24) | 6.9% | 7% | 10.9% |
| ApoB: 10169 (26) | 5.8% | 6.6% | 8.9% |
| ApoB: 10169 (27) | 14.1% | 31% | 84.9% |
| ApoB: 10169 (31) | 6.1% | 5.4% | 8.6% |
| ApoB: 10169 (32) | 6.1% | 6.4% | 8.7% |
| ApoB: 10169 (33) | 11.9% | 26.8% | 86.8% |
| ApoB: 10169 (34) | 6.7% | 5.4% | 7.6% |
| ApoB: 10169 (35) | 24.4% | 50.4% | 93.6% |
| ApoB: 10169 (36) | 13% | 14.4% | 36% |

TABLE 13

RISC Length RNA Complexes that Target the ICAM-1 Gene

| RNA Complex Identifier | Normalized Gene Silencing Activity (rLuc/fLuc) | | |
|---|---|---|---|
| (Motif #) | 25 nM RNA | 2.5 nM RNA | 0.25 nM RNA |
| Qneg (neg. control) | 100% | 100% | 100% |
| ICAM1: 1383 unmodified | 87% | 76% | 67% |
| ICAM1: 1383 (31) | 73% | 71% | 74% |
| ICAM1: 1383 (P-1) | 53% | 65% | 74% |
| ICAM1: 1383 (P1) | 55% | 57% | 64% |
| ICAM1: 1383 (P2) | 60% | 54% | 73% |
| ICAM1: 1383 (P3) | 81% | 87% | 80% |
| ICAM1: 1383 (G2) | 105% | 81% | 91% |
| ICAM1: 1383 (G7) | 87% | 61% | 75% |
| ICAM1: 1383 (P2, G2) | 73% | 68% | 72% |
| ICAM1: 1383 (P2, G7) | 79% | 74% | 89% |

TABLE 14

RISC Length RNA Complexes that Target the ApoB Gene

| RNA Complex Identifier | Percent ApoB Knockdown relative to Qneg | | |
|---|---|---|---|
| (Motif #) | 5 nM RNA | 0.5 nM RNA | 0.05 nM RNA |
| ApoB: 3410 unmodified | 80% | 57% | 0% |
| ApoB: 3410 (31) | 76% | 64% | 34% |

TABLE 14-continued

RISC Length RNA Complexes that Target the ApoB Gene

| RNA Complex Identifier | Percent ApoB Knockdown relative to Qneg | | |
|---|---|---|---|
| (Motif #) | 5 nM RNA | 0.5 nM RNA | 0.05 nM RNA |
| ApoB: 3410 (G1) | 35% | 14% | 0% |
| ApoB: 3410 (G2) | 0% | 0% | 0% |
| ApoB: 3410 (G3) | 47% | 0% | 0% |
| ApoB: 3410 (G5) | 38% | 18% | 0% |
| ApoB: 3410 (G6) | 56% | 30% | 0% |
| ApoB: 3410 (G7) | 77% | 65% | 24% |
| ApoB: 3410 (G10) | 16% | 0% | 6% |

The gene silencing activity shown in tables 8-14 above for RISC length RNA complexes indicates that hydroxymethyl nucleomonomer substitution patterns of motifs 22, 31, 32, and G7 applied to multiple siRNAs having different sequences and gene targets generally maintained and/or improved gene silencing activity of that RNA complex relative to the RNA complex having the same sequence but without a hydroxymethyl nucleomonomer monomer. Further, hydroxymethyl nucleomonomer substitution patterns of motifs P-1, P1, P2, and P3 in the RNA complex directed to ICAM-1 gene generally maintained and/or improved gene silencing activity of that RNA complex relative to the RNA complex having the same sequence but without a hydroxymethyl nucleomonomer monomer.

Strand Specific Activity of RISC Length RNA Complexes

The strand specific silencing activity (or "knockdown activity") of RISC length RNA complexes containing hydroxymethyl monomers (e.g., monomer D) was examined.

SOS1, and ICAM-1 specific RISC length RNA complexes were examined against their corresponding "reverse" psiCHECK™-2 vector plasmid (i.e., the plasmid expressed RNA this is complementary to the sense strand instead of the antisense strand, and thus the roles of each strand of the RNA complex are reversed). In the case of the "reverse" plasmid, the "sense" strand acts as the guide strand for RISC based gene silencing activity and the "antisense" strand acts as the passenger strand. For purposes of clarity, for the "forward" psiCHECK™-2 vector plasmid, the antisense strand acts as the guide strand for RISC based gene silencing activity and the sense strand acts as the passenger strand. By comparing the silencing activity of an RNA complex against both the "forward" and "reverse" vector plasmids, the silencing activity of the antisense and sense strands of an RNA complex can be determined.

For this example, the silencing activity of the guide strand (antisense strand of an RNA complex) of the ICAM-1 RNA complex against the "forward" plasmid is shown in table 13, and was compared to the silencing activity of the passenger strand (sense strand of an RNA complex) of the ICAM-1 RNA complex against the "reverse" plasmid (see table 15). For the SOS1 specific RISC length RNA complex, the silencing activity of the guide strand against the "forward" plasmid is shown in table 11, and was compared to the silencing activity of the passenger strand ("reverse plasmid"), shown in table 16.

TABLE 15

RISC Length RNA Complexes that Target the ICAM-1 Gene (Reverse Plasmid)

| RNA Complex Identifier | Normalized Gene Silencing Activity (rLuc/fLuc) | | |
|---|---|---|---|
| (Motif #) | 25 nM RNA | 2.5 nM RNA | 0.25 nM RNA |
| Qneg (neg. control) | 100% | 100% | 100% |
| ICAM1: 1383 unmodified | 57% | 49% | 62% |
| ICAM1: 1383 (31) | 57% | 46% | 50% |
| ICAM1: 1383 (P-1) | 79% | 81% | 86% |
| ICAM1: 1383 (P1) | 86% | 76% | 81% |
| ICAM1: 1383 (P2) | 99% | 71% | 81% |
| ICAM1: 1383 (P3) | 91% | 83% | 77% |
| ICAM1: 1383 (G2) | 61% | 60% | 69% |
| ICAM1: 1383 (G7) | 84% | 75% | 78% |
| ICAM1: 1383 (P2, G2) | 101% | 75% | 93% |
| ICAM1: 1383 (P2, G7) | 95% | 85% | 101% |

By comparing the results of the table 13 (ICAM-1 RNA complex against "forward" plasmid) and table 15 (ICAM-1 RNA complex against "reverse" plasmid), the position specific effect of hydroxymethyl nucleomonomers on strand specific RNAi activity is observed. For example, compare the relative silencing activity of motifs (P-1), (P1), (P2) and (P3) of RISC length ICAM1:1383 RNA complexes versus ICAM1:1383-unmodified (at 25 nM RNA) in the reverse plasmid experiment (table 15; 79%, 86%, 99%, and 91% versus 57% gene silencing activity, respectively) to the same motifs in the forward plasmid experiment (table 13; 53%, 55%, 60%, and 81% versus 87% gene silencing activity; respectively). Also, compare the relative silencing activity of motif (G2) of RISC length ICAM1:1383 RNA complexes versus ICAM1:1383-unmodified (at 25 nM RNA) in the forward plasmid experiment (table 13; 105% versus 87%, respectively) to the same motifs in the reverse plasmid experiment (table 15; 61% versus 57% gene silencing activity; respectively). In each instance, the strand of the RNA complex that serves as the guide strand has reduced or no RNAi activity against the target upon incorporation of a hydroxymethyl substituted nucleomonomer at positions −1, 2, 2 and 3 from the 5' end of that strand.

TABLE 16

RISC Length RNA Complexes that Target the SOS1 Gene (Reverse Plasmid)

| RNA Complex Identifier | Normalized Gene Silencing Activity (rLuc/fLuc) | | |
|---|---|---|---|
| (Motif #) | 25 nM RNA | 2.5 nM RNA | 0.25 nM RNA |
| Qneg (neg. control) | 100% | 100% | 100% |
| SOS1: 364 unmodified | 5.4% | 5.5% | 8.9% |
| SOS1: 364 (24) | 17.5% | 45.8% | 76.5% |
| SOS1: 364 (27) | 7.6% | 10.5% | 13.2% |
| SOS1: 364 (36) | 12.8% | 13.1% | 17.1% |

By comparing the results of the table 11 (SOS1:364 RNA complex against "forward" plasmid) and table 16 (SOS1:364 RNA complex against "reverse" plasmid), the position specific effect of hydroxymethyl nucleomonomers on strand specific RNAi activity is observed. For example, compare the relative silencing activity of motifs (24) and (27) of RISC length SOS1:364 RNA complexes versus SOS1:364-unmodified (at 2.5 nM RNA) in the reverse plasmid experiment (table 16; 45.8% and 10.5% versus 5.5% gene silencing activity, respectively) to the same motifs (24 and 27 versus unmodified) in the forward plasmid experiment (table 11; 27% and 86.5% versus 59.1% gene silencing activity; respectively). In each instance, the strand of the RNA complex that serves as the guide strand has reduced or no RNAi activity against the target upon incorporation of a hydroxymethyl substituted nucleomonomer at position 2 from the 5' end of that strand.

Therefore, placing a hydroxymethyl substituted nucleomonomer at or around positions.

−1, 1, 2, and/or 3 (particularly position 2) of a strand, counting from the 5'-end of the strand containing the hydroxymethyl nucleomonomer (e.g., sense or passenger strand) reduces or ablates the silencing activity of that strand in an RNA complex (i.e., reduce or ablate any potential "off-target" effects that may occur due to unwanted RNAi activity of the passenger strand or non-targeting strand).

Further, the results show that while introducing one or more hydroxymethyl nucleomonomers at one or more of positions −1, 1, 2, and/or 3 of in one strand of the RNA complex reduces or ablates RNAi activity of that strand, the other strand remains highly active for RNAi activity.

"Off-Target" Effects of RISC Length RNA Complexes

RNAi is a powerful technique used to disrupt the expression of a target gene, but an undesired consequence of this method is that it may also affect the expression of non-target genes (the so called "off-target" effect).

The degree of "off-target" effect of RNA complexes with and without hydroxymethyl nucleomonomers was examined. In this study, the ApoB:3410 RNA complex was used to determine the "off-target" activity of the passenger strand. The unmodified ApoB:3410 RISC length RNA complex was compared to the same sequence with motif (P-1/G7).

Briefly, HepG2 cells were cultured according to the protocol and methods described earlier in this disclosure. Microarray analysis was performed with GENECHIP Human Genome U133 Plus 2.0 microarray (AFFYMETRIX) according to manufacturer's protocol. An "off-target" gene effect was counted when a 2-fold change or greater (up or down) in gene expression levels was observed.

The results show a greater than 10-fold reduction in "off-target" effect. For the unmodified ApoB:3410 RISC length RNA complex, 389 genes had altered expression levels of 2-fold or greater, while for the ApoB:3410 RISC length RNA complex with motif (P-1/G7), only 35 genes had altered expression levels of 2-folder or greater. In both cases, the ApoB target message was reduced by about 95%.

In Vivo Gene Silencing of RISC Length RNA Complexes

The gene silencing activity of RNA complexes with and without hydroxymethyl nucleomonomers was examined in vivo. In this study, ApoB was the target. RNA complexes were administered intravenously to Balb/C mice in a formulation containing a DILA2 amino acid compound (or (E)-amino((4-(hexadecylamino)-3-(octadec-9-enamido)-4-oxobutyl) amino)methaniminium), CHEMS (cholesterol hemisuccinate), and DMPE-PEG2K (1,2-Dimyristoyl-sn-glycero-3-phosphoethanolamine with a 2 kDa PEG) at a mol % ratio of 50:28:20:2, respectively, at 0.5 mg/kg (30 nmol/kg per day), 1 mg/kg (or 60 nmol/kg per day), and 2 mg/kg (or 120 nmol/kg per day). There were five mice per group; each group was dosed at a volume of 200 μL/dose.

RNA complexes ApoB:10169 and ApoB:10169 (31) described previously, and the RNA complexes below were administered in this study. The "m" preceding a nucleotide in the sequences below indicates the presence of a 2'-O-methyl modification to that nucleoside.

DX4227 (ApoB):

```
                                        (SEQ ID NO: 157)
5'- GGAAUCmUmUAmUAmUmUmUGAUCmCAsA -3'
21-mer sense strand
```

```
                                        (SEQ ID NO: 158)
5'- mUmUGGAUmCAAAmUAmUAAGAmUUCmCsmCsU -3'
21-mer antisense strand
```

DX3838 (G1498; negative control RNA complex):

```
                                        (SEQ ID NO: 159)
5'- mGmGAUCUUAUUUCUUCGGAGACAAdTdG
25-mer sense strand
```

```
                                        (SEQ ID NO: 160)
5'- mCmAUUGUCUCCGAAGAAAUAAGAUCCUU
27-mer antisense strand
```

The percent reduction of the ApoB mRNA and corresponding percent reduction in serum cholesterol levels for each group of mice (each RNA complex Identifier row in table 16 below represents the average percent reduction in ApoB mRNA levels and serum cholesterol levels for a group of five mice) is shown in the table below. Percent reduction in ApoB mRNA is relative to the PBS alone control.

TABLE 17

Reduction in ApoB mRNA and Serum Cholesterol Levels in Mice

| RNA Complex Identifier | RNA Complex Dose | % Reduction in ApoB mRNA Levels | % Reduction in Serum Cholest. Levels |
|---|---|---|---|
| DX4227 | 1.7 mg/kg | 53% | 12% |
| DX3838 Modified Neg. Control | 2.0 mg/kg | 24% | 2% |
| ApoB: 10169 (31) | 2.0 mg/kg | 95% | 63% |
| ApoB: 10169 | 2.0 mg/kg | 80% | 45% |
| PBS Alone | — | 0% | 0% |

The data in table 16 show that a RISC length RNA complex with hydroxymethyl substituted nucleomonomers (monomer D) at positions 20 and 21 of each of the sense and antisense strand counting from the 5'-end of the strand in which the hydroxymethyl substituted nucleomonomer is located (or blunt-ended construct having a 19 base pair duplex region and two non-nucleotide hydroxymethyl nucleomonomers attached to each 3'-end of the sense strand and the antisense strand) reduced ApoB mRNA levels in vivo by 95% compared to PBS alone. The same RNA complex with 3'-end overhangs comprising TT instead reduced ApoB mRNA levels by 80%. Further, the mice showed no significant change in body weight and no appreciable toxicity was observed, indicating that RNA complexes comprising hydroxymethyl substituted nucleomonomers (monomer D) may be used as a safe and effective therapeutic. In summary, the results indicate that incorporation of acyclic hydroxymethyl substituted nucleomonomers in an RNA complex enhanced the gene silencing activity of an RNA complex in vivo.

Example 4

Position Specific Effects of Hydroxymethyl Nucleomonomer Substitution in Dicer Length RNA Complexes The substitution patterns (motifs) represented in example 2 above were applied to different sequence specific Dicer length RNA complexes. These RNA complexes are provided in tables 18-22 below. Hydroxymethyl substituted monomer(s) in the sequences of the table below are identified as "unaH" where H is the one letter code for the nucleobase (e.g., "unaC" indicates that the cytosine comprises a hydroxymethyl substituted monomer).

TABLE 18

Dicer Length RNA Complexes that Target Influenza PB2 Gene

| RNA Complex Identifier (Motif #) | Sense Sequence 5' to 3' orientation | Antisense Sequence 5' to 3' orientation |
|---|---|---|
| FluA1:2242 25/27 (G3789) | CGGGACUCUAGCAUACUUACUGAdCdA (SEQ ID NO: 161) | UGUCAGUAAGUAUGCUAGAGUCCCGUU (SEQ ID NO: 169) |
| FluA1:2242 25/27-(2) | CGGGACUCUAGCAUACUUACunaUunaGAdCdA (SEQ ID NO: 162) | UGUCAunaGunaUAAGUAUGCUAGAGUCCCGUU (SEQ ID NO: 170) |
| FluA1:2242 25/27-(3) | CGGGACUCUAGCAUACUUACunaUunaGAdCdA (SEQ ID NO: 163) | UGUCAGUAAGUAUGCUAGAGUCCCGUU (SEQ ID NO: 171) |
| FluA1:2242 25/27-(4) | CGGGACUCUAGCAUACUUACUGAdCdA (SEQ ID NO: 164) | UGUCAunaGunaUAAGUAUGCUAGAGUCCCGUU (SEQ ID NO: 172) |
| FluA1:2242 25/27-(7) | CunaGGGAunaCUCUAGCAUACUUACUGAdCdA (SEQ ID NO: 165) | UGUCAGUAAGUAUGCUAGAGUCCCGUU (SEQ ID NO: 173) |
| FluA1:2242 25/27-(8) | CGGGACUCUAGCAUACUUACUGAdCdA (SEQ ID NO: 166) | UGUCAGUunaAAGUunaAUGCUAGAGUCCCGUU (SEQ ID NO: 174) |
| FluA1:2242 25/27-(9) | CGGGACUCUAGCAUACUUACUGAdCdA (SEQ ID NO: 167) | UGUCAGUAAGUunaAUGCUAGAGUCCCGUU (SEQ ID NO: 175) |
| FluA1:2242 25/27-(10) | CGGGACUCUAGCAUACUUACUGAdCunaA (SEQ ID NO: 168) | UGUCAGUAAGUAUGCUAGAGUCCCGunaUunaU (SEQ ID NO: 176) |

TABLE 19

Dicer Length RNA Complexes that Target Influenza PA Gene

| RNA Complex Identifier (Motif #) | Sense Sequence 5' to 3' orientation | Antisense Sequence 5' to 3' orientation |
|---|---|---|
| FluA3:2089 25/27 (G8282) | GCAAUUGAGGAGUGCCUGAUUAATdG (SEQ ID NO: 177) | CAUUAAUCAGGCACUCCUCAAUUGCUU (SEQ ID NO: 185) |
| FluA3:2089 25/27-(2) | GCAAUUGAGGAGUGCCUGAUunaUunaAATdG (SEQ ID NO: 178) | CAUUAunaAunaUCAGGCACUCCUCAAUUGCUU (SEQ ID NO: 186) |
| FluA3:2089 25/27-(3) | GCAAUUGAGGAGUGCCUGAUunaUunaAATdG (SEQ ID NO: 179) | CAUUAAUCAGGCACUCCUCAAUUGCUU (SEQ ID NO: 187) |
| FluA3:2089 25/27-(4) | GCAAUUGAGGAGUGCCUGAUUAATdG (SEQ ID NO: 180) | CAUUAunaAunaUCAGGCACUCCUCAAUUGCUU (SEQ ID NO: 188) |
| FluA3:2089 25/27-(7) | GunaCAAUunaUGAGGAGUGCCUGAUUAATdG (SEQ ID NO: 181) | CAUUAAUCAGGCACUCCUCAAUUGCUU (SEQ ID NO: 189) |
| FluA3:2089 25/27-(8) | GCAAUUGAGGAGUGCCUGAUUAATdG (SEQ ID NO: 182) | CAUUAAUunaCAGGunaCACUCCUCAAUUGCUU (SEQ ID NO: 190) |
| FluA3:2089 25/27-(9) | GCAAUUGAGGAGUGCCUGAUUAATdG (SEQ ID NO: 183) | CAUUAAUCAGGunaCACUCCUCAAUUGCUU (SEQ ID NO: 191) |
| FluA3:2089 25/27-(10) | GCAAUUGAGGAGUGCCUGAUUAAdUunaG (SEQ ID NO: 184) | CAUUAAUCAGGCACUCCUCAAUUGCunaUunaU (SEQ ID NO: 192) |

TABLE 20

Dicer Length RNA Complexes that Target Influenza NP Gene

| RNA Complex Identifier | Sense Sequence 5' to 3' orientation | Antisense Sequence 5' to 3' orientation |
|---|---|---|
| G1498 DS (DX3030) | GGAUCUUAUUUCUUCGGAGACAAdTdG (SEQ ID NO: 193) | CAUUGUCUCCGAAGAAAUAAGAUCCUU (SEQ ID NO: 201) |
| FluA5:1498 25/27-(2) | GGAUCUUAUUUCUUCGGAGAunaCunaAAdTdG (SEQ ID NO: 194) | CAUUGunaUunaCUCCGAAGAAAUAAGAUCCUU (SEQ ID NO: 202) |

TABLE 20-continued

Dicer Length RNA Complexes that Target Influenza NP Gene

| RNA Complex Identifier | Sense Sequence 5' to 3' orientation | Antisense Sequence 5' to 3' orientation |
|---|---|---|
| FluA5:1498 25/27-(3) | GGAUCUUAUUUCUUCGGAGAunaCunaAAdTdG (SEQ ID NO: 195) | CAUUGUCUCCGAAGAAAUAAGAUCCUU (SEQ ID NO: 203) |
| FluA5:1498 25/27-(4) | GGAUCUUAUUUCUUCGGAGACAAdTdG (SEQ ID NO: 196) | CAUUGunaUunaCUCCGAAGAAAUAAGAUCCUU (SEQ ID NO: 204) |
| FluA5:1498 25/27-(7) | GunaGAUCunaUUAUUUCUUCGGAGACAAdTdG (SEQ ID NO: 197) | CAUUGUCUCCGAAGAAAUAAGAUCCUU (SEQ ID NO: 205) |
| FluA5:1498 25/27-(8) | GGAUCUUAUUUCUUCGGAGACAAdTdG (SEQ ID NO: 198) | CAUUGUCunaUCCGunaAAGAAAUAAGAUCCUU (SEQ ID NO: 206) |
| FluA5:1498 25/27-(9) | GGAUCUUAUUUCUUCGGAGACAAdTdG (SEQ ID NO: 199) | CAUUGUCUCCGunaAAGAAAUAAGAUCCUU (SEQ ID NO: 207) |
| FluA5:1498 25/27-(10) | GGAUCUUAUUUCUUCGGAGACAAdUunaG (SEQ ID NO: 200) | CAUUGUCUCCGAAGAAAUAAGAUCCunaUunaU (SEQ ID NO: 208) |

TABLE 21

Dicer Length RNA Complexes that Target the SOS1 Gene

| RNA Complex Identifier (Motif #) | Sense Sequence 5' to 3' orientation | Antisense Sequence 5' to 3' orientation |
|---|---|---|
| SOS1:364 25/27 | AUUGACCACCAGGUUUCUGUUUAdCdA (SEQ ID NO: 209) | UGUAAACAGAAACCUGGUGGUCAAUUU (SEQ ID NO: 217) |
| SOS1:364 25/27-(2) | AUUGACCACCAGGUUUCUGUunaUunaUAdCdA (SEQ ID NO: 210) | UGUAAunaAunaCAGAAACCUGGUGGUCAAUUU (SEQ ID NO: 218) |
| SOS1:364 25/27-(3) | AUUGACCACCAGGUUUCUGUunaUunaUAdCdA (SEQ ID NO: 211) | UGUAAACAGAAACCUGGUGGUCAAUUU (SEQ ID NO: 219) |
| SOS1:364 25/27-(4) | AUUGACCACCAGGUUUCUGUUUAdCdA (SEQ ID NO: 212) | UGUAAunaAunaCAGAAACCUGGUGGUCAAUUU (SEQ ID NO: 220) |
| SOS1:364 25/27-(7) | AunaUUGAunaCCACCAGGUUUCUGUUUAdCdA (SEQ ID NO: 213) | UGUAAACAGAAACCUGGUGGUCAAUUU (SEQ ID NO: 221) |
| SOS1:364 25/27-(8) | AUUGACCACCAGGUUUCUGUUUAdCdA (SEQ ID NO: 214) | UGUAAACunaAGAAunaACCUGGUGGUCAAUUU (SEQ ID NO: 222) |
| SOS1:364 25/27-(9) | AUUGACCACCAGGUUUCUGUUUAdCdA (SEQ ID NO: 215) | UGUAAACAGAAunaACCUGGUGGUCAAUUU (SEQ ID NO: 223) |
| SOS1:364 25/27-(10) | AUUGACCACCAGGUUUCUGUUUAdCunaA (SEQ ID NO: 216) | UGUAAACAGAAACCUGGUGGUCAAUunaUunaU (SEQ ID NO: 224) |

TABLE 22

Dicer Length RNA Complexes that Target the ApoB Gene

| RNA Complex Identifier (Motif #) | Sense Sequence 5' to 3' orientation | Antisense Sequence 5' to 3' orientation |
|---|---|---|
| DX3951:ApoB 25/27 | GUCAUCACACUGAAUACCAAUGCTdG (SEQ ID NO: 225) | CAGCAUUGGUAUUCAGUGUGAUGACAC (SEQ ID NO: 233) |
| ApoB:10167 25/27-(2) | GUCAUCACACUGAAUACCAAunaUunaGCTdG (SEQ ID NO: 226) | CAGCAunaUunaUGGUAUUCAGUGUGAUGACAC (SEQ ID NO: 234) |
| ApoB:10167 25/27-(3) | GUCAUCACACUGAAUACCAAunaUunaGCTdG (SEQ ID NO: 227) | CAGCAUUGGUAUUCAGUGUGAUGACAC (SEQ ID NO: 235) |
| ApoB:10167 25/27-(4) | GUCAUCACACUGAAUACCAAUGCTdG (SEQ ID NO: 228) | CAGCAunaUunaUGGUAUUCAGUGUGAUGACAC (SEQ ID NO: 236) |

TABLE 22-continued

Dicer Length RNA Complexes that Target the ApoB Gene

| RNA Complex Identifier (Motif #) | Sense Sequence 5' to 3' orientation | Antisense Sequence 5' to 3' orientation |
|---|---|---|
| ApoB:10167 25/27-(7) | GunaUCAUunaCACACUGAAUACCAAUGCTdG (SEQ ID NO: 229) | CAGCAUUGGUAUUCAGUGUGAUGACAC (SEQ ID NO: 237) |
| ApoB:10167 25/27-(8) | GUCAUCACACUGAAUACCAAUGCTdG (SEQ ID NO: 230) | CAGCAUUunaGGUAunaUUCAGUGUGAUGACAC (SEQ ID NO: 238) |
| ApoB:10167 25/27-(9) | GUCAUCACACUGAAUACCAAUGCTdG (SEQ ID NO: 231) | CAGCAUUGGUAunaUUCAGUGUGAUGACAC (SEQ ID NO: 239) |
| ApoB:10167 25/27-(10) | GUCAUCACACUGAAUACCAAUGCdUunaG (SEQ ID NO: 232) | CAGCAUUGGUAUUCAGUGUGAUGACunaAunaC (SEQ ID NO: 240) |

Gene Silencing Activity of Dicer Length RNA Complexes

The gene silencing activity (or "knockdown activity") of Dicer length RNA complexes containing hydroxymethyl monomers (e.g., monomer D) was examined.

Transfections were performed in HeLa cells as described previously in this disclosure, and dual-luciferase reporter activity was used to determine gene silencing activity for each of the Dicer length RNA complex, as described previously in this disclosure. The gene silencing activity for Dicer length RNA complex is shown in tables 22-25 below. All samples were normalized to the respective dsRNA Qneg (QIAGEN) negative control samples run in the same experiment. That is, Qneg values were set as 100% active (i.e., no knockdown), with 95% confidence intervals (CI).

TABLE 23

Dicer Length RNA Complexes that Target Influenza PB2 Gene

| RNA Complex Identifier (Motif #) | Normalized Gene Silencing Activity (rLuc/fLuc) | | |
|---|---|---|---|
| | 25 nM RNA | 2.5 nM RNA | 0.25 nM RNA |
| Qneg (neg. control) | 100% | 100% | 100% |
| FluA1: 2242 25/27 (G3789) | 13.5% | 14.7% | 17.5% |
| FluA1: 2242 25/27-(2) | 20.1% | 25.9% | 54.4% |
| FluA1: 2242 25/27-(3) | 15.7% | 10.6% | 15.7% |
| FluA1: 2242 25/27-(4) | 28.3% | 30.2% | 53.6% |
| FluA1: 2242 25/27-(7) | 17% | 22.9% | 26.3% |
| FluA1: 2242 25/27-(8) | 35.6% | 38.3% | 66.2% |
| FluA1: 2242 25/27-(9) | 18.3% | 22.5% | 28.8% |
| FluA1: 2242 25/27-(10) | 15.1% | 24.7% | 42.3% |

TABLE 24

Dicer Length RNA Complexes that Target Influenza PA Gene

| RNA Complex Identifier (Motif #) | Normalized Gene Silencing Activity (rLuc/fLuc) | | |
|---|---|---|---|
| | 25 nM RNA | 2.5 nM RNA | 0.25 nM RNA |
| Qneg (neg. control) | 100% | 100% | 100% |
| FluA3: 2089 25/27 (G8282) | 24.1% | 20.8% | 32.6% |
| FluA3: 2089 25/27-(2) | 60.4% | 58.8% | 81.3% |
| FluA3: 2089 25/27-(3) | 18.4% | 22.1% | 36.1% |
| FluA3: 2089 25/27-(4) | 67.8% | 86.1% | 103.3% |
| FluA3: 2089 25/27-(7) | 25% | 27.2% | 40% |
| FluA3: 2089 25/27-(8) | 43.6% | 63.7% | 96.7% |

TABLE 24-continued

Dicer Length RNA Complexes that Target Influenza PA Gene

| RNA Complex Identifier (Motif #) | Normalized Gene Silencing Activity (rLuc/fLuc) | | |
|---|---|---|---|
| | 25 nM RNA | 2.5 nM RNA | 0.25 nM RNA |
| FluA3: 2089 25/27-(9) | 37.3% | 40.5% | 66% |
| FluA3: 2089 25/27-(10) | 23.7% | 27.1% | 61.2% |

TABLE 25

Dicer Length RNA Complexes that Target Influenza NP Gene

| RNA Complex Identifier (Motif #) | Normalized Gene Silencing Activity (rLuc/fLuc) | | |
|---|---|---|---|
| | 25 nM RNA | 2.5 nM RNA | 0.25 nM RNA |
| Qneg (neg. control) | 100% | 100% | 100% |
| G1498 DS (DX3030) | 23.4% | 19% | 19.8% |
| FluA5: 1498 25/27-(2) | 54.4% | 86.1% | 88.9% |
| FluA5: 1498 25/27-(3) | 19.3% | 23.4% | 36.3% |
| FluA5: 1498 25/27-(4) | 61% | 79.7% | 74.6% |
| FluA5: 1498 25/27-(7) | 26.2% | 28% | 40.6% |
| FluA5: 1498 25/27-(8) | 24.9% | 25.5% | 45.7% |
| FluA5: 1498 25/27-(9) | 27.7% | 29.9% | 38.6% |
| FluA5: 1498 25/27-(10) | 20.8% | 23.1% | 33.4% |

TABLE 26

Dicer Length RNA Complexes that Target the SOS1 Gene

| RNA Complex Identifier (Motif #) | Normalized Gene Silencing Activity (rLuc/fLuc) | | |
|---|---|---|---|
| | 25 nM RNA | 2.5 nM RNA | 0.25 nM RNA |
| Qneg (neg. control) | 100% | 100% | 100% |
| SOS1: 364 25/27 | 23.4% | 16.7% | 37% |
| SOS1: 364 25/27-(2) | 123.8% | 86.5% | 104.1% |
| SOS1: 364 25/27-(3) | 22.9% | 28.8% | 51.1% |
| SOS1: 364 25/27-(4) | 107.3% | 84.4% | 119.1% |
| SOS1: 364 25/27-(7) | 19.3% | 13.7% | 30.8% |
| SOS1: 364 25/27-(8) | 38.6% | 34.8% | 57.6% |
| SOS1: 364 25/27-(9) | 35.6% | 36.6% | 64% |
| SOS1: 364 25/27-(10) | 16% | 20.3% | 55% |

TABLE 27

Dicer Length RNA Complexes that Target the ApoB Gene

| RNA Complex Identifier (Motif #) | Normalized Gene Silencing Activity (rLuc/fLuc) | | |
|---|---|---|---|
| | 25 nM RNA | 2.5 nM RNA | 0.25 nM RNA |
| Qneg (neg. control) | 100% | 100% | 100% |
| DX3951: ApoB dicer | 8.5% | 7% | 11.9% |
| ApoB: 10167 25/27-(2) | 6.8% | 6.1% | 10.8% |
| ApoB: 10167 25/27-(3) | 40.6% | 48.2% | 90.6% |
| ApoB: 10167 25/27-(4) | 7.7% | 7.3% | 15.3% |
| ApoB: 10167 25/27-(7) | 32.8% | 37.8% | 69.9% |
| ApoB: 10167 25/27-(8) | 8.2% | 7.4% | 17.9% |
| ApoB: 10167 25/27-(9) | 10.9% | 9.4% | 20.1% |
| ApoB: 10167 25/27-(10) | 9.1% | 6.4% | 21.5% |

The gene silencing activity shown in tables 22-25 above for Dicer length RNA complexes indicates that hydroxymethyl nucleomonomer substitution patterns of motifs 3, 7, 9 and 10 applied to multiple siRNAs having different sequences and gene targets generally maintained and/or improved gene silencing activity of that RNA complex relative to the RNA complex having the same sequence but without a hydroxymethyl nucleomonomer monomer.

Cytokine Induction of Dicer Length RNA Complexes

Cytokine induction of Dicer length RNA complexes containing hydroxymethyl monomers (e.g., monomer D) was examined.

Briefly, human peripheral blood mononuclear cells (PBMCs) were isolated by Ficoll gradient from pooled human blood. Cells were cultured in IMDM media with 10% FBS, 1×NEAA, and 1× Glutamax. PBMCs were plated at 320,000 cells per well in 100 µL growth media. PBMCs were transfected for 4 hours with a mixture of 100 nM of one of the RNA complexes in the table above and 0.25 µL RNAiMAX (final transfection media was about 120 µL) in OptiMEM. Each transfection was performed in triplicate. After four hours of transfection, growth media was added to each well to a final volume of 250 µL. Transfected cells were cultured for 24 hours before supernatant was collected. Cell and cell debris were removed by centrifugation and the clarified supernatants were frozen at −20° C. until assayed for cytokine induction. Levels of human IFN-α in the collected supernatant were measured by ELISA (PBL Biomedical human IFN alpha kit; Cat. #4100-2; manufactures protocol was followed). Levels of human IFN-α were used to indicate a general immune response. Human IFN-α in levels human PBMC's transfected with the Dicer length RNA complexes is shown in tables 28 and 29 below.

TABLE 28

Average IFN-α Levels in Human PBMC Cells

| RNA Complex Identifier (Motif #) | Ave. Levels of IFN-α (pg/mL) |
|---|---|
| Cells Alone (no RNA complex) | 0 |
| RNAiMAX (no RNA complex) | 3.2 |
| FluA1: 2242 25/27 (G3789) | 229.3 |
| FluA1: 2242 25/27-2 | 0 |
| FluA1: 2242 25/27-3 | 0 |
| FluA1: 2242 25/27-4 | 0 |
| FluA1: 2242 25/27-7 | 180.7 |
| FluA1: 2242 25/27-8 | 0 |
| FluA1: 2242 25/27-9 | 241.5 |
| FluA1: 2242 25/27-10 | 2.6 |
| FluA3: 2089 25/27 (G8282) | 53.5 |
| FluA3: 2089 25/27-2 | 0 |
| FluA3: 2089 25/27-3 | 0 |
| FluA3: 2089 25/27-4 | 0 |
| FluA3: 2089 25/27-7 | 0 |
| FluA3: 2089 25/27-8 | 0 |
| FluA3: 2089 25/27-9 | 24.2 |
| FluA3: 2089 25/27-10 | 0 |
| G1498 DS (DX3030) | 311.7 |
| FluA5: 1498 25/27-2 | 0 |
| FluA5: 1498 25/27-3 | 19.6 |
| FluA5: 1498 25/27-4 | 25.5 |
| FluA5: 1498 25/27-7 | 21 |
| FluA5: 1498 25/27-8 | 28.4 |
| FluA5: 1498 25/27-9 | 148.2 |
| FluA5: 1498 25/27-10 | 63.6 |

TABLE 29

Average IFN-α Levels in Human PBMC Cells

| RNA Complex Identifier (Motif #) | Ave. Levels of IFN-α (pg/mL) |
|---|---|
| Cells Alone (no RNA complex) | 3.2 |
| RNAiMAX (no RNA complex) | 8.5 |
| SOS1: 364 25/27 | 252.7 |
| SOS1: 364 25/27-2 | 0 |
| SOS1: 364 25/27-3 | 0 |
| SOS1: 364 25/27-4 | 0 |
| SOS1: 364 25/27-7 | 197 |
| SOS1: 364 25/27-8 | 0 |
| SOS1: 364 25/27-9 | 92.1 |
| SOS1: 364 25/27-10 | 6 |
| DX3951: ApoB dicer | 39.4 |
| ApoB: 10167 25/27-2 | 1 |
| ApoB: 10167 25/27-3 | 21.5 |
| ApoB: 10167 25/27-4 | 4 |
| ApoB: 10167 25/27-7 | 59.6 |
| ApoB: 10167 25/27-8 | 2.6 |
| ApoB: 10167 25/27-9 | 4.5 |
| ApoB: 10167 25/27-10 | 20.5 |

Motifs 2, 3, 4, 8, and 10 applied to five different Dicer length RNA complexes targeting five different genes reduced and/or ablated cytokine induction relative to the same RNA complex without a hydroxymethyl substituted monomers.

The results of the ELISA assay show that hydroxymethyl substituted monomers flanking both dicer cleavage sites (e.g., Modification motif 2) of any of the Dicer length RNA complexes does not induce human IFN-α production in human PBMCs (compare to the unmodified form of the RNA complex). Introduction of a hydroxymethyl substituted monomers at positions 21 and 22 of the sense strand, positions 2 and 6 of the sense strand of a Dicer length RNA complex (counting from the 5'-end of the sense strand) eliminates or reduces human IFN-α expression compared to the same RNA complex without a hydroxymethyl substituted monomer. Introduction of a hydroxymethyl substituted monomer at positions 6 and 7 of the antisense strand or position 8 of the antisense strand of a Dicer length RNA complex eliminates or reduces human IFN-α expression compared to the same RNA complex without a hydroxymethyl substituted monomer. Introduction of a hydroxymethyl substituted monomer at position 25 of the sense strand and positions 26 and 27 of the antisense strand of a Dicer length RNA complex eliminates or reduces human IFN-α expression compared to the same RNA complex without a hydroxymethyl substituted monomer. Also, introduction of a hydroxymethyl substituted monomer at positions 21 and 22 of the sense strand and positions 6 and 7 of the antisense strand of a Dicer length RNA complex eliminates or reduces human IFN-α expression compared to the same RNA complex without a hydroxymethyl substituted monomer.

To further investigate the cytokine response and the ability to the hydroxymethyl substituted nucleomonomer to "mask" an RNA complex, or eliminate or reduce cytokine induction, TLR3 (Toll-like receptor 3), MDA5 (IFIH1), and RIG-I (retinoic acid-inducible gene 1) activation were examined.

TLR3 is a member of the Toll-like receptor family of pattern recognition receptors of the innate immune system. It recognizes double-stranded RNAs, for example from RNA viruses. TLR3 recognizes dsRNA and activates NF-κB to increase production of type I interferon (cytokine), which then subsequently signals to other cells to increase their antiviral defenses.

MDA-5 and RIG-I also recognize double-stranded RNA and function as a "sensor" for viral infections, for example RNA viruses.

Briefly, human umbilical endothelial cells (HUVEC's) were plated at 45,000 cells per well in a 48 well plate in EGM-2 growth media with 2% serum and growth supplements (EGM-2 BULLETKIT; Cambrex Bio Science). After incubating the cells for about 24 hours, HUVEC's were transfected for 4 hours with a mixture of 50 nM of one of the RNA complexes (FluA1:2242 25/27, G3789 D-siRNA or FluA1:2242 25/27-10) and RNAiMAX, the positive control Poly I:C or RNAiMAX alone (no RNA). Each transfection was performed in triplicate. After 4 hours of transfection, 200 µL EGM-2 growth media was added to each well. Transfected cells were cultured for 24 hours before lysis and supernatant collection. Levels of TLR3, MDA-5 and RIG-I were measured by QUANTIGENE assay according the manufactures protocol (AFFYMETRIX). The levels of TLR3, MDA-5 and RIG-I expression are shown in table 30 below. All levels are normalized to PPIA expression levels.

TABLE 30

Fold Change in mRNA Expression Levels for TLR3, MDA-5 and RIG-I

| Treatment | Fold Change in mRNA Levels Normalized to PPIA Expression Levels | | |
|---|---|---|---|
| | TLR3 | MDA-5 | RIG-I |
| RNAiMAX | 1 | 1 | 1 |
| Poly I: C | 128 | 149 | 35 |
| FluA1: 2242 25/27, G3789 unmodified | 116 | 141 | 34 |
| FluA1: 2242 25/27- (10) | 2 | 3 | 2 |

The expression levels shown in table 30 above indicate that the Dicer length RNA complex (FluA1:2242 25/27, G3789 unmodified) without hydroxymethyl substituted nucleomonomers induces TLR3, MDA-5 and RIG-I expression levels above that of RNAiMAX alone and comparable to the positive control Poly I:C. In contrast, the same Dicer length RNA complex with hydroxymethyl substituted nucleomonomers (motif 10) does not induce TLR3, MDA-5 or RIG-I expression levels. Thus, strategic positioning of hydroxymethyl substituted nucleomonomers can "mask" a Dicer length RNA complex from cell receptors that support activation of an immune response to double-stranded RNA.

Processing of Dicer Length RNA Complexes by Dicer Enzyme

Processing of Dicer length RNA complexes comprising hydroxymethyl substituted monomers by Dicer enzyme was examined.

Dicer length RNA complexes G3789, G8282, G1498, SOS1 and ApoB, unmodified, or containing the modification motif 2, 3, or 4 (see Example 2 for modification motif description) were incubated with Dicer enzyme in vitro and purified by HPLC and analyzed by LC-MS to determine the amount of processing by the Dicer enzyme.

Briefly, unmodified and modified RNA complexes were prepared at 40 μM by mixing appropriate ratios of the sense and antisense strands in buffer and heated to 95° C. for one minute and then allowed to cool slowly back to room temperature. RNA complexes were subject to Dicer enzyme for 24 hours at 37° C. After a 24 hour incubation period, samples were desalted with floating dialysis membranes with 600 mL of water for one hour. Samples were then loaded in HPLC vials and injected onto the LC-MS. The HPLC parameters were as follows: flow rate of 0.2 mL/minute, XTerra® column MS $C_{18}$ 2.5 μm, 2.1×50 mm, column temperature 65° C., mobile phase A: 100 mM HFIP, 7 mM TEA, pH 8.1; mobile phase B: 100% methanol, gradient 2-14% over 40 minutes without any precolumn volume, and injection volume was 15 μL. The LC-MS parameters were as follows: negative ion mode, capillary 3.0 kV, cone 40 V, desolv. temperature 300° C., desolv. Flow rate ($N_2$) 600 L/hour, source temperature 90° C., acquisitions 300-1950 m/z over 1.5 seconds. The mass spectra data was deconvulated using MaxEnt® (maximum entropy) software written by Micromass® (Waters®).

Motifs 2, 3 and 4 applied to five different Dicer length RNA complexes targeting five different genes prevent processing by Dicer enzyme.

The data show that Dicer enzyme did not process Dicer length RNA complexes having hydroxymethyl substituted monomers flanking the Dicer cut site regardless whether the hydroxymethyl substituted monomers were in both the sense and antisense strands or in one strand (sense or antisense strand). Unmodified RNA complexes were cleaved by Dicer enzyme. All modified Dicer length RNA complexes examined having hydroxymethyl substituted monomers retained gene silencing activity (see above) indicating that even though the RNA complex is not processed by Dicer enzyme, these RNA complexes are still active for RNAi activity and reduce target gene expression.

Thus, a Dicer length RNA complex having hydroxymethyl substituted monomers at positions 21 and 22 (motif 3) of the sense strand counting from the 5'-end of the sense strand are not processed by the Dicer enzyme. Further, an RNA complex comprising hydroxymethyl substituted monomers at positions 6 and 7 of the antisense strand counting from the 5'-end of the antisense strand (motif 4) are not processed by the Dicer enzyme. An RNA complex comprising hydroxymethyl substituted monomers at positions 21 and 22 of the sense strand counting from the 5'-end of the sense strand and hydroxymethyl substituted monomers at positions 6 and 7 of the antisense strand counting from the 5'-end of the antisense strand are not processed by the Dicer enzyme (motif 2).

The invention claimed is:

1. An oligomeric compound comprising one or more acyclic 2'-3'-seco-monomers and one or more ribonucleic acid monomers, the oligomeric compound comprising a sense strand and an antisense strand that together form only one double-stranded region of 15 to 24 base pairs, wherein the 5'-terminal monomer of the sense strand is a terminus of the double-stranded region, wherein any one or more of the two positions at the 5'-end of the sense strand is occupied by the same or different acyclic 2'-3'-seco-monomer, wherein the oligomeric compound has at least one 3'-overhang, and wherein the oligomeric compound is active in RNA interference to modulate expression of a targeted mRNA.

2. The oligomer of claim 1, further comprising that one or both of the last two positions of the 3'-end of the antisense strand is occupied by the same or different acyclic 2'-3'-seco-monomer.

3. The oligomeric compound of claim 1, wherein the double-stranded region has 19 or 20 base pairs.

4. The oligomeric compound of claim 1, wherein the sense strand and the antisense strand are each 21 or 22 nucleomonomers in length.

5. The oligomeric compound of claim 1, wherein the oligomeric compound has a blunt end.

6. The oligomeric compound of claim 1, wherein the antisense strand has a region of at least 15 contiguous nucleomonomers corresponding to any 15 contiguous nucleomonomers of SEQ ID NOs: 12, 34, 56, 78, 100, 124, or 147.

7. The oligomeric compound of claim 1, wherein the acyclic 2'-3'-seco-monomer is selected from the group of monomers D, F, G, H, I, and J:

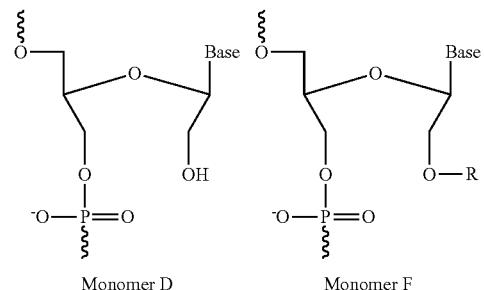

Monomer D        Monomer F

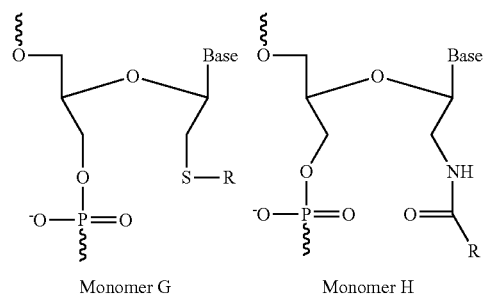

Monomer G        Monomer H

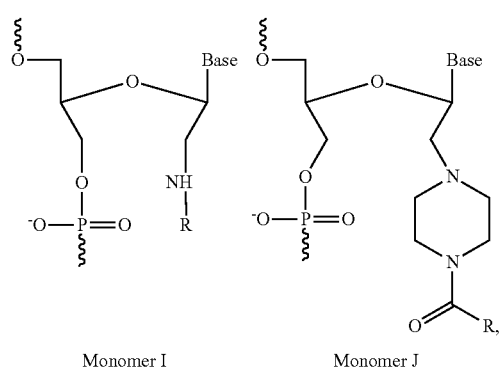

Monomer I        Monomer J wherein R is selected from the group consisting of a hydrogen, an alkyl group, a cholesterol derivative, a fluorophore, a polyamine, a fatty acid, an amino acid, a saccharide and a polypeptide wherein Base is any purine, pyrimidine, or derivative or analogue thereof.

8. The oligomeric compound of claim 1, further comprising a nucleotide analogue selected from the group consisting of 2'-O-alkyl-RNA monomers, 2'-amino-DNA monomers, 2'-fluoro-DNA monomers, PNA monomers, HNA monomers, ANA monomers, FANA monomers, CeNA monomers, ENA monomers, DNA monomers, and INA monomers.

9. A method for reducing expression of a gene in a cell comprising preparing an oligomeric compound of claim 1 and treating the cell with the oligomeric compound.

\* \* \* \* \*